United States Patent
Wranik et al.

(10) Patent No.: US 9,688,758 B2
(45) Date of Patent: Jun. 27, 2017

(54) SINGLE-CHAIN ANTIBODIES AND OTHER HETEROMULTIMERS

(71) Applicant: Genentech, Inc., South San Francisco, CA (US)

(72) Inventors: Bernd Wranik, South San Francisco, CA (US); Dan L. Eaton, South San Francisco, CA (US); Erin H. Christensen, South San Francisco, CA (US); Jiansheng Wu, South San Francisco, CA (US)

(73) Assignee: GENENTECH, INC., South San Francisco, CA (US)

( * ) Notice: Subject to any disclaimer, the term of this patent is extended or adjusted under 35 U.S.C. 154(b) by 0 days.

(21) Appl. No.: 14/455,189

(22) Filed: Aug. 8, 2014

(65) Prior Publication Data

US 2015/0133638 A1 May 14, 2015

Related U.S. Application Data

(63) Continuation of application No. PCT/US2013/025365, filed on Feb. 8, 2013.

(60) Provisional application No. 61/597,486, filed on Feb. 10, 2012.

(51) Int. Cl.
*A61K 39/395* (2006.01)
*C07K 16/00* (2006.01)
*C07K 16/28* (2006.01)
*C07K 16/18* (2006.01)
*C07K 16/22* (2006.01)
*C07K 16/24* (2006.01)
*C07K 16/26* (2006.01)

(52) U.S. Cl.
CPC ............. *C07K 16/28* (2013.01); *C07K 16/00* (2013.01); *C07K 16/18* (2013.01); *C07K 16/22* (2013.01); *C07K 16/24* (2013.01); *C07K 16/26* (2013.01); *C07K 2317/31* (2013.01); *C07K 2317/515* (2013.01); *C07K 2317/53* (2013.01); *C07K 2317/622* (2013.01); *C07K 2317/64* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 3,896,111 A | 7/1975 | Kupchan et al. |
| 4,120,469 A | 10/1978 | Westermeier |
| 4,120,649 A | 10/1978 | Schechter |
| 4,137,230 A | 1/1979 | Hashimoto et al. |
| 4,150,149 A | 4/1979 | Wolfsen et al. |
| 4,151,042 A | 4/1979 | Higashide et al. |
| 4,248,870 A | 2/1981 | Miyashita et al. |
| 4,256,746 A | 3/1981 | Miyashita et al. |
| 4,260,608 A | 4/1981 | Miyashita et al. |
| 4,265,814 A | 5/1981 | Hashimoto et al. |
| 4,294,757 A | 10/1981 | Asai |
| 4,307,016 A | 12/1981 | Asai et al. |
| 4,308,268 A | 12/1981 | Miyashita et al. |
| 4,308,269 A | 12/1981 | Miyashita et al. |
| 4,309,428 A | 1/1982 | Miyashita et al. |
| 4,313,946 A | 2/1982 | Powell et al. |
| 4,315,929 A | 2/1982 | Freedman et al. |
| 4,317,821 A | 3/1982 | Miyashita et al. |
| 4,322,348 A | 3/1982 | Asai et al. |
| 4,331,598 A | 5/1982 | Hasegawa et al. |
| RE30,985 E | 6/1982 | Cartaya |
| 4,361,544 A | 11/1982 | Goldberg |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,419,446 A | 12/1983 | Howely et al. |
| 4,424,219 A | 1/1984 | Hashimoto et al. |
| 4,444,744 A | 4/1984 | Goldenberg |
| 4,450,254 A | 5/1984 | Isley et al. |
| 4,560,655 A | 12/1985 | Baker |
| 4,601,978 A | 7/1986 | Karin |
| 4,657,866 A | 4/1987 | Kumar |
| 4,665,077 A | 5/1987 | Stringfellow et al. |
| 4,737,456 A | 4/1988 | Weng et al. |
| 4,767,704 A | 8/1988 | Cleveland |
| 4,816,567 A | 3/1989 | Cabilly et al. |
| 4,927,762 A | 5/1990 | Darfler |
| 4,948,882 A | 8/1990 | Ruth |
| 4,965,199 A | 10/1990 | Capon |
| 4,975,278 A | 12/1990 | Senter et al. |
| 5,053,394 A | 10/1991 | Ellestad et al. |
| 5,114,721 A | 5/1992 | Cohen et al. |

(Continued)

FOREIGN PATENT DOCUMENTS

| | | |
|---|---|---|
| CN | 1173878 A | 2/1998 |
| CN | 1176659 A | 3/1998 |

(Continued)

OTHER PUBLICATIONS

Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
Raag et al. (FASEB, 1995, 9:73-80).*
Yamaguchi et al. (Journal of Immunological Methods, 1995, 259-267).*
Liu et al. (Journal of Pharmaceutical Sciences, 2007, 97:2426-2447).*
Remacle et al. (Journal of Biological Chemistry, 2008, 283:20897-20906).*
Arie et al. (2001). "Chaperone Function of FkpA, a Heat Shock Prolyl Isomerase, in the Periplasm of *Escherichia coli*," *Mol. Microbiol.* 39(1):199-210.

(Continued)

*Primary Examiner* — Julie Wu
(74) *Attorney, Agent, or Firm* — Morrison & Foerster LLP

(57) ABSTRACT

The invention provides engineered heteromultimeric protein complexes constructed using one, two, or three tethers and methods for making, using, and purifying such complexes, such as antibodies with different binding properties.

53 Claims, 12 Drawing Sheets

(56) References Cited

U.S. PATENT DOCUMENTS

| | | |
|---|---|---|
| 5,122,469 A | 6/1992 | Mather et al. |
| 5,143,844 A | 9/1992 | Abrahmsen et al. |
| 5,202,238 A | 4/1993 | Fell, Jr. et al. |
| 5,204,244 A | 4/1993 | Fell et al. |
| 5,208,020 A | 5/1993 | Chari et al. |
| 5,264,365 A | 11/1993 | Georgiou et al. |
| 5,362,852 A | 11/1994 | Geoghegan |
| 5,416,064 A | 5/1995 | Chari et al. |
| 5,451,463 A | 9/1995 | Nelson et al. |
| 5,500,362 A | 3/1996 | Robinson et al. |
| 5,508,192 A | 4/1996 | Georgiou et al. |
| 5,519,142 A | 5/1996 | Hoess et al. |
| 5,532,142 A | 7/1996 | Johnston et al. |
| 5,541,313 A | 7/1996 | Ruth |
| 5,571,894 A | 11/1996 | Wels et al. |
| 5,574,141 A | 11/1996 | Seliger et al. |
| 5,585,481 A | 12/1996 | Arnold, Jr. et al. |
| 5,587,458 A | 12/1996 | King et al. |
| 5,591,828 A | 1/1997 | Bosslet et al. |
| 5,624,821 A | 4/1997 | Winter et al. |
| 5,635,483 A | 6/1997 | Pettit et al. |
| 5,639,635 A | 6/1997 | Joly et al. |
| 5,641,870 A | 6/1997 | Rinderknecht et al. |
| 5,648,237 A | 7/1997 | Carter et al. |
| 5,648,260 A | 7/1997 | Winter et al. |
| 5,663,149 A | 9/1997 | Pettit et al. |
| 5,712,374 A | 1/1998 | Kuntsmann et al. |
| 5,714,586 A | 2/1998 | Kunstmann et al. |
| 5,731,168 A | 3/1998 | Carter et al. |
| 5,739,113 A | 4/1998 | Lee |
| 5,739,116 A | 4/1998 | Hamann et al. |
| 5,747,654 A | 5/1998 | Pastan et al. |
| 5,767,285 A | 6/1998 | Hamann et al. |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,789,199 A | 8/1998 | Joly et al. |
| 5,798,229 A | 8/1998 | Strittmatter et al. |
| 5,817,786 A | 10/1998 | Ruth |
| 5,821,333 A | 10/1998 | Carter et al. |
| 5,821,337 A | 10/1998 | Carter et al. |
| 5,824,483 A | 10/1998 | Houston |
| 5,840,523 A | 11/1998 | Simmons et al. |
| 5,849,879 A | 12/1998 | Nguyen et al. |
| 5,869,046 A | 2/1999 | Presta et al. |
| 5,877,296 A | 3/1999 | Hamann et al. |
| 5,885,793 A | 3/1999 | Griffiths et al. |
| 5,932,448 A | 8/1999 | Tso et al. |
| 5,959,083 A | 9/1999 | Bosslet et al. |
| 5,959,177 A | 9/1999 | Hein et al. |
| 6,027,888 A | 2/2000 | Georgiou et al. |
| 6,040,498 A | 3/2000 | Stomp et al. |
| 6,083,715 A | 7/2000 | Georgiou et al. |
| 6,136,564 A | 10/2000 | Kopetzki |
| 6,153,190 A | 11/2000 | Young et al. |
| 6,166,185 A | 12/2000 | Davis et al. |
| 6,171,586 B1 | 1/2001 | Lam et al. |
| 6,194,551 B1 | 2/2001 | Idusogie et al. |
| 6,239,259 B1 | 5/2001 | Davis et al. |
| 6,248,516 B1 | 6/2001 | Winter et al. |
| 6,267,958 B1 | 7/2001 | Andya et al. |
| 6,350,860 B1 | 2/2002 | Buyse et al. |
| 6,417,429 B1 | 7/2002 | Hein et al. |
| 6,420,548 B1 | 7/2002 | Vezina et al. |
| 6,511,663 B1 | 1/2003 | King et al. |
| 6,531,581 B1 | 3/2003 | Nardone et al. |
| 6,534,628 B1 | 3/2003 | Nilsson et al. |
| 6,558,672 B1 | 5/2003 | Pastan et al. |
| 6,586,207 B2 | 7/2003 | Tirrell et al. |
| 6,602,684 B1 | 8/2003 | Umana et al. |
| 6,630,579 B2 | 10/2003 | Chari et al. |
| 6,660,843 B1 | 12/2003 | Feige et al. |
| 6,833,441 B2 | 12/2004 | Wang et al. |
| 6,835,809 B1 | 12/2004 | Liu et al. |
| 6,897,044 B1 | 5/2005 | Braslawsky et al. |
| 6,919,426 B2 | 7/2005 | Boone et al. |
| 6,946,292 B2 | 9/2005 | Kanda et al. |
| 6,982,321 B2 | 1/2006 | Winter |
| 7,125,978 B1 | 10/2006 | Vezina et al. |
| 7,129,330 B1 | 10/2006 | Little et al. |
| 7,355,008 B2 | 4/2008 | Stavenhagen et al. |
| 7,381,408 B2 | 6/2008 | Mezo et al. |
| 7,498,298 B2 | 3/2009 | Doronina et al. |
| 7,507,796 B2 | 3/2009 | Little et al. |
| 7,642,228 B2 | 1/2010 | Carter et al. |
| 7,651,688 B2 | 1/2010 | Hanai et al. |
| 7,666,622 B2 | 2/2010 | Sharma et al. |
| 7,695,936 B2 | 4/2010 | Carter et al. |
| 7,919,257 B2 | 4/2011 | Hoogenboom et al. |
| 7,942,042 B2 | 5/2011 | Kawakita et al. |
| 8,216,805 B2 | 7/2012 | Carter et al. |
| 8,227,577 B2 | 7/2012 | Klein et al. |
| 8,242,247 B2 | 8/2012 | Klein et al. |
| 8,268,314 B2 | 9/2012 | Baehner et al. |
| 8,304,713 B2 | 11/2012 | Pradel |
| 8,309,300 B2 | 11/2012 | Jununtula et al. |
| 8,796,424 B2 | 8/2014 | Croasdale et al. |
| 8,871,912 B2 | 10/2014 | Davis et al. |
| 2002/0051986 A1 | 5/2002 | Baez et al. |
| 2002/0155537 A1 | 10/2002 | Carter et al. |
| 2003/0027751 A1 | 2/2003 | Kovesdi et al. |
| 2003/0124129 A1 | 7/2003 | Oliner |
| 2003/0152987 A1 | 8/2003 | Cohen et al. |
| 2003/0170230 A1 | 9/2003 | Caterer et al. |
| 2003/0176352 A1 | 9/2003 | Min et al. |
| 2003/0195156 A1 | 10/2003 | Min et al. |
| 2003/0219817 A1 | 11/2003 | Zhu et al. |
| 2003/0229023 A1 | 12/2003 | Oliner et al. |
| 2003/0236193 A1 | 12/2003 | Oliner et al. |
| 2004/0018557 A1 | 1/2004 | Qu et al. |
| 2004/0033561 A1 | 2/2004 | O'Keefe et al. |
| 2004/0038339 A1 | 2/2004 | Kufer et al. |
| 2004/0214988 A1 | 10/2004 | Tirrell et al. |
| 2004/0220388 A1 | 11/2004 | Metens et al. |
| 2004/0224372 A1 | 11/2004 | Li et al. |
| 2005/0054048 A1 | 3/2005 | Grasso et al. |
| 2005/0064509 A1 | 3/2005 | Bradbury et al. |
| 2005/0079170 A1 | 4/2005 | Le Gall et al. |
| 2005/0100543 A1 | 5/2005 | Hansen et al. |
| 2005/0152894 A1 | 7/2005 | Krummen et al. |
| 2005/0163782 A1 | 7/2005 | Glaser et al. |
| 2005/0169933 A1 | 8/2005 | Steeves et al. |
| 2005/0186208 A1 | 8/2005 | Fyfe et al. |
| 2005/0214833 A1 | 9/2005 | Carter et al. |
| 2005/0238649 A1 | 10/2005 | Doronina et al. |
| 2005/0249722 A1 | 11/2005 | Beliard et al. |
| 2005/0260186 A1 | 11/2005 | Bookbinder et al. |
| 2006/0008845 A1 | 1/2006 | Kondejewski et al. |
| 2006/0063921 A1 | 3/2006 | Moulder et al. |
| 2006/0104968 A1 | 5/2006 | Bookbinder et al. |
| 2006/0122370 A1 | 6/2006 | Oliner et al. |
| 2006/0134709 A1 | 6/2006 | Stavenhagen et al. |
| 2006/0160184 A1 | 7/2006 | Mattheus Hoogenboom et al. |
| 2006/0280747 A1 | 12/2006 | Fuh et al. |
| 2007/0014794 A1 | 1/2007 | Carter et al. |
| 2007/0071675 A1 | 3/2007 | Wu et al. |
| 2007/0071742 A1 | 3/2007 | Fang et al. |
| 2007/0141065 A1 | 6/2007 | Fuh et al. |
| 2007/0178552 A1 | 8/2007 | Arathoon et al. |
| 2007/0196274 A1 | 8/2007 | Sun |
| 2007/0269369 A1 | 11/2007 | Gegg et al. |
| 2007/0274985 A1* | 11/2007 | Dubel .................. C07K 16/00 424/133.1 |
| 2007/0274998 A1 | 11/2007 | Uktu |
| 2007/0287170 A1 | 12/2007 | Davis et al. |
| 2008/0044834 A1 | 2/2008 | Heyduk |
| 2008/0063641 A1 | 3/2008 | Huang et al. |
| 2008/0187954 A1 | 8/2008 | Kallmeier et al. |
| 2008/0280778 A1 | 11/2008 | Urdea |
| 2009/0023811 A1 | 1/2009 | Biadatti et al. |
| 2009/0117105 A1 | 5/2009 | Hu et al. |
| 2009/0155275 A1* | 6/2009 | Wu ...................... C07K 16/468 424/136.1 |

(56) References Cited

U.S. PATENT DOCUMENTS

| | | | |
|---|---|---|---|
| 2009/0162359 A1 | 6/2009 | Klein et al. | |
| 2009/0162360 A1 | 6/2009 | Klein et al. | |
| 2009/0175851 A1 | 7/2009 | Klein et al. | |
| 2009/0194692 A1 | 8/2009 | Kobaru | |
| 2009/0232811 A1 | 9/2009 | Klein et al. | |
| 2010/0021943 A1 | 1/2010 | An et al. | |
| 2010/0062436 A1 | 3/2010 | Jarosch et al. | |
| 2010/0081796 A1 | 4/2010 | Brinkmann et al. | |
| 2010/0111967 A1 | 5/2010 | Baehner et al. | |
| 2010/0254989 A1 | 10/2010 | Bossenmaier et al. | |
| 2010/0256338 A1* | 10/2010 | Brinkmann | C07K 16/00 530/387.3 |
| 2010/0256339 A1 | 10/2010 | Bossenmaier et al. | |
| 2010/0256340 A1 | 10/2010 | Brinkmann et al. | |
| 2010/0266617 A1 | 10/2010 | Carven et al. | |
| 2010/0316645 A1 | 12/2010 | Imhof-Jung et al. | |
| 2010/0322934 A1 | 12/2010 | Imhof-Jung et al. | |
| 2010/0322935 A1 | 12/2010 | Croasdale et al. | |
| 2011/0054151 A1 | 3/2011 | Lazar et al. | |
| 2011/0243966 A1* | 10/2011 | Farrington | A61K 47/48338 424/178.1 |
| 2012/0149879 A1 | 6/2012 | Brinkmann et al. | |
| 2012/0164726 A1 | 6/2012 | Klein et al. | |
| 2012/0184718 A1 | 7/2012 | Bruenker et al. | |
| 2012/0225071 A1 | 9/2012 | Klein et al. | |
| 2012/0237506 A1 | 9/2012 | Bossenmaier et al. | |
| 2012/0237507 A1 | 9/2012 | Bossenmaier et al. | |
| 2012/0302737 A1 | 11/2012 | Christensen et al. | |
| 2012/0321627 A1 | 12/2012 | Baehner et al. | |
| 2013/0022601 A1 | 1/2013 | Brinkmann et al. | |
| 2013/0058937 A1 | 3/2013 | Auer et al. | |
| 2013/0060011 A1 | 3/2013 | Bruenker et al. | |
| 2013/0078249 A1 | 3/2013 | Ast et al. | |
| 2013/0156772 A1 | 6/2013 | Bossenmaier et al. | |
| 2013/0266568 A1 | 10/2013 | Brinkmann et al. | |
| 2013/0267686 A1 | 10/2013 | Brinkmann et al. | |
| 2013/0273054 A1 | 10/2013 | Bossenmaier et al. | |
| 2013/0288267 A1 | 10/2013 | Gerg et al. | |
| 2013/0344094 A1 | 12/2013 | Gerg et al. | |
| 2014/0249296 A1 | 9/2014 | Ploegh | |
| 2014/0294810 A1 | 10/2014 | Lowman et al. | |
| 2015/0004166 A1 | 1/2015 | Baehner et al. | |
| 2015/0030598 A1 | 1/2015 | Croasdale et al. | |
| 2015/0232541 A1 | 8/2015 | Fenn et al. | |
| 2015/0232560 A1 | 8/2015 | Heindl et al. | |
| 2015/0232561 A1 | 8/2015 | Fenn et al. | |
| 2015/0291704 A1 | 10/2015 | Beck | |

FOREIGN PATENT DOCUMENTS

| | | | |
|---|---|---|---|
| CN | 1232039 A | 10/1999 | |
| CN | 1603345 A | 4/2005 | |
| CN | 101052653 A | 10/2007 | |
| CN | 101065151 A | 10/2007 | |
| CN | 101205255 A | 6/2008 | |
| CN | 101218251 A | 7/2008 | |
| CN | 101355966 A | 1/2009 | |
| EP | 0 292 128 A1 | 11/1988 | |
| EP | 0 307 434 B1 | 3/1989 | |
| EP | 0 307 434 B2 | 3/1989 | |
| EP | 0 313 219 A2 | 4/1989 | |
| EP | 0 339 217 B1 | 11/1989 | |
| EP | 0 340 109 A2 | 11/1989 | |
| EP | 0 404 097 B1 | 12/1990 | |
| EP | 0 423 839 A2 | 4/1991 | |
| EP | 0 425 235 B1 | 5/1991 | |
| EP | 0 523 978 A1 | 1/1993 | |
| EP | 0 618 192 A1 | 10/1994 | |
| EP | 0 637 593 A1 | 2/1995 | |
| EP | 0 786 468 A2 | 7/1997 | |
| EP | 1 074 563 A1 | 2/2001 | |
| EP | 1 186 613 A1 | 3/2002 | |
| EP | 1 391 213 A1 | 2/2004 | |
| EP | 1 431 298 A1 | 6/2004 | |
| EP | 1 538 221 A1 | 6/2005 | |
| EP | 1 870 459 A1 | 12/2007 | |
| EP | 2 050 764 A1 | 4/2009 | |
| EP | 2 443 154 B1 | 4/2012 | |
| JP | 7-501698 A | 2/1995 | |
| JP | 2008-531049 A | 8/2008 | |
| RU | 2005/124281 A | 1/2006 | |
| WO | WO-87/00195 A1 | 1/1987 | |
| WO | WO-89/02439 A1 | 3/1989 | |
| WO | WO-89/02931 A1 | 4/1989 | |
| WO | WO-89/12642 A1 | 12/1989 | |
| WO | WO-90/03430 A1 | 4/1990 | |
| WO | WO-90/08156 A1 | 7/1990 | |
| WO | WO-90/08187 A1 | 7/1990 | |
| WO | WO-90/11294 A1 | 10/1990 | |
| WO | WO-91/01133 A1 | 2/1991 | |
| WO | WO-91/06305 A1 | 5/1991 | |
| WO | WO-92/01047 A1 | 1/1992 | |
| WO | WO-92/04053 A1 | 3/1992 | |
| WO | WO-92/11388 A1 | 7/1992 | |
| WO | WO-93/01161 A1 | 1/1993 | |
| WO | WO-93/05060 A1 | 3/1993 | |
| WO | WO-93/06217 A1 | 4/1993 | |
| WO | WO-93/11161 A1 | 6/1993 | |
| WO | WO-93/11162 A1 | 6/1993 | |
| WO | WO-93/16185 A2 | 8/1993 | |
| WO | WO-93/16185 A3 | 8/1993 | |
| WO | WO-93/21232 A1 | 10/1993 | |
| WO | WO-94/04550 A1 | 3/1994 | |
| WO | WO-94/09131 A1 | 4/1994 | |
| WO | WO-94/10202 A1 | 5/1994 | |
| WO | WO-94/10308 A1 | 5/1994 | |
| WO | WO-94/11026 A2 | 5/1994 | |
| WO | WO-94/29350 A2 | 12/1994 | |
| WO | WO-94/29350 A3 | 12/1994 | |
| WO | WO-95/05399 A1 | 2/1995 | |
| WO | WO-95/09917 A1 | 4/1995 | |
| WO | WO-95/17886 A1 | 7/1995 | |
| WO | WO-96/27011 A1 | 9/1996 | |
| WO | WO-96/27612 A1 | 9/1996 | |
| WO | WO-97/01580 A1 | 1/1997 | |
| WO | WO-97/05156 A1 | 2/1997 | |
| WO | WO-97/14719 A1 | 4/1997 | |
| WO | WO-97/028267 A1 | 8/1997 | |
| WO | WO-97/028267 C1 | 8/1997 | |
| WO | WO-97/43451 A1 | 11/1997 | |
| WO | WO-98/45331 A2 | 10/1998 | |
| WO | WO-98/45331 A3 | 10/1998 | |
| WO | WO-98/45332 A2 | 10/1998 | |
| WO | WO-98/45332 A3 | 10/1998 | |
| WO | WO-98/48032 A2 | 10/1998 | |
| WO | WO-98/48032 A3 | 10/1998 | |
| WO | WO-98/50431 A2 | 11/1998 | |
| WO | WO-99/06587 A2 | 2/1999 | |
| WO | WO-99/06587 A3 | 2/1999 | |
| WO | WO-99/37791 A1 | 7/1999 | |
| WO | WO-99/54342 A1 | 10/1999 | |
| WO | WO-99/66951 A2 | 12/1999 | |
| WO | WO-99/66951 A3 | 12/1999 | |
| WO | WO-99/66951 C1 | 12/1999 | |
| WO | WO-00/24770 A2 | 5/2000 | |
| WO | WO-00/24770 A3 | 5/2000 | |
| WO | WO-00/29004 A1 | 5/2000 | |
| WO | WO-00/35956 A1 | 6/2000 | |
| WO | WO-00/61739 A1 | 10/2000 | |
| WO | WO 01/42505 A2 | 6/2001 | |
| WO | WO 01/42505 A3 | 6/2001 | |
| WO | WO-01/77342 A1 | 10/2001 | |
| WO | WO-01/90192 A2 | 11/2001 | |
| WO | WO-02/02781 A1 | 1/2002 | |
| WO | WO-02/051870 A2 | 7/2002 | |
| WO | WO 02/072141 A2 | 9/2002 | |
| WO | WO 02/072141 A3 | 9/2002 | |
| WO | WO-02/088172 A2 | 11/2002 | |
| WO | WO-02/092620 A2 | 11/2002 | |
| WO | WO-02/092620 A3 | 11/2002 | |
| WO | WO-03/012069 A2 | 2/2003 | |
| WO | WO-03/030833 A2 | 4/2003 | |
| WO | WO-03/030833 A3 | 4/2003 | |

(56) References Cited

FOREIGN PATENT DOCUMENTS

| | | |
|---|---|---|
| WO | WO-03/031589 A2 | 4/2003 |
| WO | WO-03/035694 A2 | 5/2003 |
| WO | WO-03/035694 A3 | 5/2003 |
| WO | WO-03/035835 A2 | 5/2003 |
| WO | WO-03/035835 A3 | 5/2003 |
| WO | WO-03/055993 A1 | 7/2003 |
| WO | WO-03/057134 A2 | 7/2003 |
| WO | WO-03/057134 A3 | 7/2003 |
| WO | WO-03/066660 A2 | 8/2003 |
| WO | WO-03/073238 A2 | 9/2003 |
| WO | WO-03/073238 A3 | 9/2003 |
| WO | WO-03/097105 A1 | 11/2003 |
| WO | WO 03/104249 A1 | 12/2003 |
| WO | WO-03/106501 A1 | 12/2003 |
| WO | WO-2004/032961 A1 | 4/2004 |
| WO | WO 2004/003019 * | 6/2004 |
| WO | WO-2004/058298 A1 | 7/2004 |
| WO | WO 2004/062602 A2 | 7/2004 |
| WO | WO 2004/062602 A3 | 7/2004 |
| WO | WO-2004/065417 A2 | 8/2004 |
| WO | WO-2004/065540 A2 | 8/2004 |
| WO | WO-2004/065540 A3 | 8/2004 |
| WO | WO-2004/072117 A2 | 8/2004 |
| WO | WO-2004/072117 A3 | 8/2004 |
| WO | WO 2004/081051 A1 | 9/2004 |
| WO | WO-2004/092215 A2 | 10/2004 |
| WO | WO-2004/092215 A3 | 10/2004 |
| WO | WO-2005/000900 A1 | 1/2005 |
| WO | WO-2005/001025 A2 | 1/2005 |
| WO | WO-2005/001025 A3 | 1/2005 |
| WO | WO-2005/004809 A2 | 1/2005 |
| WO | WO-2005/004809 A3 | 1/2005 |
| WO | WO-2005/005635 A2 | 1/2005 |
| WO | WO-2005/005635 A3 | 1/2005 |
| WO | WO-2005/011735 A1 | 2/2005 |
| WO | WO-2005/018572 A2 | 3/2005 |
| WO | WO-2005/018572 A3 | 3/2005 |
| WO | WO-2005/027966 A2 | 3/2005 |
| WO | WO-2005/027966 A3 | 3/2005 |
| WO | WO-2005/035572 A2 | 4/2005 |
| WO | WO-2005/035572 A3 | 4/2005 |
| WO | WO-2005/035727 A2 | 4/2005 |
| WO | WO-2005/035727 A3 | 4/2005 |
| WO | WO-2005/044853 A2 | 5/2005 |
| WO | WO-2005/044853 A3 | 5/2005 |
| WO | WO-2005/044859 A2 | 5/2005 |
| WO | WO-2005/044859 A3 | 5/2005 |
| WO | WO-2005/051976 A2 | 6/2005 |
| WO | WO-2005/063816 A2 | 7/2005 |
| WO | WO-2005/063816 A3 | 7/2005 |
| WO | WO-2005/074524 A2 | 8/2005 |
| WO | WO-2005/075514 A2 | 8/2005 |
| WO | WO-2006/020258 A2 | 2/2006 |
| WO | WO-2006/020258 A3 | 2/2006 |
| WO | WO-2005/035727 A2 | 3/2006 |
| WO | WO-2005/035727 A3 | 3/2006 |
| WO | WO-2006/031370 A2 | 3/2006 |
| WO | WO-2006/031370 A3 | 3/2006 |
| WO | WO-2006/034488 A2 | 3/2006 |
| WO | WO-2006/034488 A3 | 3/2006 |
| WO | WO-2006/044908 A2 | 4/2006 |
| WO | WO-2006/044908 A3 | 4/2006 |
| WO | WO-2006/045049 A1 | 4/2006 |
| WO | WO-2006/068953 A2 | 6/2006 |
| WO | WO-2006/068953 A3 | 6/2006 |
| WO | WO-2006/082515 A2 | 8/2006 |
| WO | WO-2006/082515 A3 | 8/2006 |
| WO | WO-2006/089364 A1 | 8/2006 |
| WO | WO-2006/091209 A2 | 8/2006 |
| WO | WO-2006/091209 A3 | 8/2006 |
| WO | WO-2006/093794 A1 | 8/2006 |
| WO | WO-2006/103100 A2 | 10/2006 |
| WO | WO-2006/103100 A3 | 10/2006 |
| WO | WO-2006/113665 A2 | 10/2006 |
| WO | WO-2006/114700 A2 | 11/2006 |
| WO | WO-2006/114700 A3 | 11/2006 |
| WO | WO-2006/116260 A2 | 11/2006 |
| WO | WO-2006/116260 A3 | 11/2006 |
| WO | WO 2006/137932 A2 | 12/2006 |
| WO | WO 2006/137932 A3 | 12/2006 |
| WO | WO-2007/024715 A2 | 3/2007 |
| WO | WO-2007/031875 A2 | 3/2007 |
| WO | WO-2007/031875 A3 | 3/2007 |
| WO | WO 2007/038658 A2 | 4/2007 |
| WO | WO 2007/038658 A3 | 4/2007 |
| WO | WO-2007/044887 A2 | 4/2007 |
| WO | WO-2007/044887 A3 | 4/2007 |
| WO | WO-2007/048037 A2 | 4/2007 |
| WO | WO-2007/048037 A3 | 4/2007 |
| WO | WO 2007/059816 A1 | 5/2007 |
| WO | WO-2007/068895 A1 | 6/2007 |
| WO | WO 2007/069092 A2 | 6/2007 |
| WO | WO 2007/069092 A3 | 6/2007 |
| WO | WO 2007/084181 A2 | 7/2007 |
| WO | WO-2007/084181 A3 | 7/2007 |
| WO | WO-2007/089445 A2 | 8/2007 |
| WO | WO-2007/089445 A3 | 8/2007 |
| WO | WO-2007/095338 A2 | 8/2007 |
| WO | WO-2007/108013 A2 | 9/2007 |
| WO | WO-2007/109254 A2 | 9/2007 |
| WO | WO-2007/110205 A2 | 10/2007 |
| WO | WO-2007/110205 A3 | 10/2007 |
| WO | WO-2008/005828 A2 | 1/2008 |
| WO | WO-2008/005828 A3 | 1/2008 |
| WO | WO-2008/017963 A2 | 2/2008 |
| WO | WO-2008/017963 A3 | 2/2008 |
| WO | WO-2008/077077 A2 | 6/2008 |
| WO | WO-2008/077077 A3 | 6/2008 |
| WO | WO-2008/077546 A1 | 7/2008 |
| WO | WO-2008/100624 A2 | 8/2008 |
| WO | WO-2008/100624 A3 | 8/2008 |
| WO | WO-2008/132568 A2 | 11/2008 |
| WO | WO-2008/132568 A3 | 11/2008 |
| WO | WO-2009/007124 A1 | 1/2009 |
| WO | WO-2009/018386 A1 | 2/2009 |
| WO | WO-2009/021745 A1 | 2/2009 |
| WO | WO-2009/021754 A2 | 2/2009 |
| WO | WO-2009/021754 A3 | 2/2009 |
| WO | WO-2009/023843 A1 | 2/2009 |
| WO | WO-2009/030780 A2 | 3/2009 |
| WO | WO-2009/030780 A3 | 3/2009 |
| WO | WO-2009/032782 A2 | 3/2009 |
| WO | WO-2009/032782 A3 | 3/2009 |
| WO | WO 2009/037659 A2 | 3/2009 |
| WO | WO 2009/037659 A3 | 3/2009 |
| WO | WO 2009/059278 A1 | 5/2009 |
| WO | WO-2009/080251 A1 | 7/2009 |
| WO | WO-2009/080252 A1 | 7/2009 |
| WO | WO-2009/080253 A1 | 7/2009 |
| WO | WO-2009/080254 A1 | 7/2009 |
| WO | WO 2009/105671 A2 | 8/2009 |
| WO | WO 2009/105671 A3 | 8/2009 |
| WO | WO-2009/126944 A1 | 10/2009 |
| WO | WO-2010/034441 A1 | 4/2010 |
| WO | WO-2010/040508 A1 | 4/2010 |
| WO | WO-2010/040508 A8 | 4/2010 |
| WO | WO-2010/040508 A9 | 4/2010 |
| WO | WO 2010/045193 A1 | 4/2010 |
| WO | WO-2010/065882 A1 | 6/2010 |
| WO | WO-2010/069532 A1 | 6/2010 |
| WO | WO-2010/087994 A2 | 8/2010 |
| WO | WO-2010/112193 A1 | 10/2010 |
| WO | WO-2010/112194 A1 | 10/2010 |
| WO | WO-2010/115552 A1 | 10/2010 |
| WO | WO-2010/115589 A1 | 10/2010 |
| WO | WO-2010/115589 A8 | 10/2010 |
| WO | WO 2010/118169 A2 | 10/2010 |
| WO | WO 2010/118169 A3 | 10/2010 |
| WO | WO-2010/136172 A1 | 12/2010 |
| WO | WO-2010/145792 A1 | 12/2010 |
| WO | WO-2010/145793 A1 | 12/2010 |
| WO | WO-2011/028952 A1 | 3/2011 |
| WO | WO-2011/034605 A2 | 3/2011 |
| WO | WO-2011/133886 A2 | 10/2011 |

(56) References Cited

FOREIGN PATENT DOCUMENTS

| | | |
|---|---|---|
| WO | WO-2012/006633 A1 | 1/2012 |
| WO | WO-2012/025525 A1 | 3/2012 |
| WO | WO-2012/025530 A1 | 3/2012 |
| WO | WO-2012/085069 A2 | 6/2012 |
| WO | WO-2012/085069 A3 | 6/2012 |
| WO | WO-2012/085111 A1 | 6/2012 |
| WO | WO-2012/085113 A1 | 6/2012 |
| WO | WO-2012/116927 A1 | 9/2012 |
| WO | WO-2013/003555 A1 | 1/2013 |
| WO | WO-2013/006544 A1 | 1/2013 |
| WO | WO-2013/006544 A8 | 1/2013 |
| WO | WO-2013/026833 A1 | 2/2013 |
| WO | WO-2013/092716 A1 | 6/2013 |
| WO | WO-2013/119966 A2 | 8/2013 |
| WO | WO-2013/174873 A1 | 11/2013 |
| WO | WO-2014/001326 A1 | 1/2014 |

OTHER PUBLICATIONS

Bachman (1987). "Derivations and Genotypes of Some Mutant Derivatives of *Esherichia coli* K-12," Chapter 72 in *Escherichia coli and Samonella typimurium Cellular and Molecular Biology*, vol. 2, American Society for Microbiology, Washington D.C., pp. 1190-1219.
Baldwin et al. (1986). "Monoclonal Antibodies in Cancer Treatment," *Lancet* 60:603-606.
Barnes et al. (Mar. 1, 1980). "Methods for Growth of Cultured Cells in Serum-free Medium," *Anal. Biochem.* 102:255-270.
Bass et al. (1990). "Hormone Phage: An Enrichment Method for Variant Proteins With Altered Binding Properties," *Proteins* 8:309-314.
Booy et al. (Mar.-Apr. 2006, e-pub. Mar. 24, 2006). "Monoclonal and Bispecific Antibodies as Novel Therapeutics," *Arch. Immunol. Ther. Exp.* 54:85-101.
Bothmann et al. (Jun. 2, 2000). "The Periplasmic *Escherichia coli* Peptidylprolyl *cis,trans*-Isomerase FkpA. I. Increased Functional Expression of Antibody Fragments With and Without *cis*-Prolines," *J. Biol. Chem.* 275(22):17100-17105.
Burton. (1985). "Immunoglobulin G: Functional Sites," *Molec. Immunol.* 22(3):161-206.
Cao et al. (2003). "Bispecific Antibody Conjugates in Therapeutics," *Advanced Drug Delivery Reviews* 55:171-197.
Capel et al. (1994). "Heterogenity of Human IgG Fc Receptors," *Immunomethods* 4:25-34.
Carlsson et al. (Sep. 1, 1978). "Protein Thiolation and Reversible Protein-protein Conjugation. *N*-Succinimidyl 3-(2-pyridyldithio)propionate, a New Heterobifunctional Reagent," *Biochem. J.* 173:723-737.
Carter et al. (May 15, 1992). "Humanization of an Anti-p185$^{HER2}$ Antibody for Human Cancer Therapy," *Proc. Natl. Acad. Sci USA* 89(10):4285-4289.
Chari et al. (Jan. 1, 1992). "Immunoconjugates Containing Novel Maytansinoids: Promising Anticancer Drugs," *Cancer Research* 52:127-131.
Chen et al. (Nov. 5, 1999). "Selection and Analysis of an Optimized Anti-VEGF Antibody: Crystal Structure of an Affinity-matured Fab in Complex With Antigen," *J. Mol. Biol.* 293(4):865-681.
Chen et al. (1999). "Chaperone Activity of DsbC," *J. Biol. Chem.* 274:19601-19605.
Chothia et al. (1987). "Canonical Structures for the Hypervariable Regions of Immunoglobulins," *J. Mol. Biol.* 196:901-917.
Chow et al. (Jun. 30, 2000). "Studies on the Subsite Specificity of Rat Nardilysin (N-arginine Dibasic Convertase)," *J. Biol. Chem..* 275:19545-19551.
Clynes et al. (Jan. 1998). "Fc Receptors are Required in Passive and Active Immunity to Melanoma," *Proc. Natl. Acad. Sci. USA* 95:652-656.
Daëron. (1997). "Fc Receptor Biology," *Annu. Rev. Immunol.* 15:203-234.

Davies. (1994). "'Camelising' Human Antibody Fragments: NMR Studies on VH Domains," *Febs Letter* 339:285-290.
De Haas et al. (Oct. 1995). "Fcy Receptors of Phagocytes," *J. Lab. Clin. Med.* 126:330-341.
Dooley et al. (2006). "Antibody Repertoire Development in Cartilaginous Fish," *Dev. Comp. Immunol.* 30(1-2):43-56.
Doronina et al. (Jul. 2, 2003, e-pub. Jun. 1, 2003). "Development of Potent Monoclonal Antibody Auristatin Conjugates for Cancer Therapy," *Nat. Biotechnol.* 21(7):778-784.
Eaton et al. (Dec. 30, 1986). "Construction and Characterization of an Active Factor VIII Variant Lacking the Central One-Third of the Molecule," *Biochemistry* 25:8343-8347.
Els Conrath et al. (Mar. 9, 2001). "Camel Single-domain Antibodies as Modular Building Units in Bispecific and Bivalent Antibody Constructs," *Journal of Biological Chemistry* 276(19):7346-7350.
Fischer et al. (2007). "Bispecific Antibodies: Molecules that Enable Novel Therapeutic Strategies," *Pathbiology* 74(1):3-14.
Fraker et al. (Feb. 28, 1978). "Protein and Cell Membrane Iodinations With a Sparingly Soluble Chloroamide, 1,3,4,6-tetrachloro-3a,6a-diphenylglycoluril," *Biochem. Biophys. Res. Commun.* 80(4):49-57.
Gazzano-Santoro et al. (1996). "A Non-radiactive Complement-dependent Cytotoxicity Assay for Anti-CD20 Monoclonal Antibody," *J. Immunol. Methods* 202:163.
Geoghegan et al. (1992). "Site-Directed Conjugation of Nonpeptide Groups to Peptides and Proteins via Periodate Oxidation of a 2-Amino Alcohol. Application Modification at N Terminator Serine," *Bioconjugate Chem.* 3:138-146.
Graham et al. (1977). "Characteristics of a Human Cell Line Transformed by DNA From Human Adenovirus Type 5," *J. Gen Virol.* 36:59-72.
Guss et al. (1986). "Structure of the IgG-binding regions of streptococcal protein G," *EMBO J.* 5:1567-1575.
Guyer et al. (1976). "Immunoglobulin Binding by Mouse Intestinal Epithelial Cell Receptors," *J. Immunol.* 117:587.
Ham et al. (1979). "Media and Growth Requirements," *Meth. Enz.* 58:44-93.
Hara et al. (1996). "Overproduction of Penicillin-binding Protein 7 Suppresses Thermosensitive Growth Defect at Low Osmolarity Due to an *spr* Mutation of *Escherichia coli,*" *Microbial Drug Resistance* 2:63-72.
Hinman et al. (Jul. 15, 1993). "Preparation and Characterization of Monoclonal Antibody Conjugates of the Calicheamicins: A Novel and Potent Family of Antitumor Antibiotics," *Cancer Res.* 53:3336-3342.
Hollinger et al. (1993). "Diabodies': Small bivalent and Bispecific Antibody Fragments," *Proc. Natl. Acad. Sci. USA* 90-6444-6448.
Holt et al. (Nov. 2003). "Domain Antibodies: Proteins for Therapy," *Trends Biotechnol.* 21:484-490.
Janeway. (Oct. 12, 1989). "Immunotherapy by Peptdes?," *Nature* 341:482-483.
Joly et al. (1998). "Overexpression of *Escherichia coli* Oxidoreductases Increases Recombinant Insulin-like Growth Factor-I Accumulation," *Proc. Natl. Acad. Sci. USA* 95-2773-2777.
Jones et al. (May 29, 1986). "Replacing the Complementarity-determining Regions in a Human Antibody with those From a Mouse," *Nature* 321:522-525.
Kim et al. (1994). "Localization of the Site of the Murine IgG1 Molecule that is Involved in Binding to the Murine Intestinal Fc Receptor," *Eur J Immunol.* 24:2429-2434.
Lindmark et al. (1983). "Binding of Immunoglobulins to Protein A and Immunoglobulin Levels in Mammalian Sera," *J. Immunol. Meth.* 62:1-13.
Liu et al. (Aug. 6, 1996) "Eradication of Large Colon Tumor Xenografts by Targeted Delivery of Maytansinoids," *Proc. Natl. Acad. Sci. USA* 93:8618-8623.
Lode et al. (1998). "Targeted Therapy With a Novel Enediyene Antibiotic Calicheamicin $\theta^1$ Effectively Suppresses Growth and Dissemination of Liver Metastases in a Syngeneic Model of Murine Neuroblastoma," *Cancer Res.* 58:2925-2928.
MacCallum et al. (1996)."Antibody-antigen Interactions: Contact Analysis and Binding Site Topography," *J. Mol. Biol.* 262:732-745.

(56) References Cited

OTHER PUBLICATIONS

Malmborg et al. (1995). "BIAcore as a Tool in Antibody Engineering," *J. Immunol. Methods* 183:7-13.

Mandler et al (Oct. 4, 2000). "Immunoconjugates of Geldanamycin and Anti-HER2 Monoclonal Antibodies: Antiproliferative Activity on Human Breast Carcinoma Cell Lines," *J. of the Nat. Cancer Inst.* 92(19):1573-1581.

Mandler et al. (May 15, 2000). "Synthesis and Evaluation of Antiproliferative Activity of a Geldanamycin-Herceptin Immunoconjugate," *Biorganic & Med. Chem. Letters* 10:1025-1028.

Mandler et al. (Jul.-Aug. 2002). "Modifications in Synthesis Strategy Improve the Yield and Efficacy of Geldanamycin-herceptin Immunoconjugates," *Bioconjugate Chem.* 13:786-791.

Marvin et al. (2006). "Bispecific Antibodies for Dual-modality Cancer Therapy: Killing Two Signaling Cascades with One Stone," *Current Opinion in Drug Discovery & Development* 9(2):184-193.

Mather (1980). "Establishment and Characterization of Two Distinct Mouse Testicular Epithelial Cell Lines," *Biol. Reprod.* 23:243-251.

Mather et al. (1982). "Culture of Testicular Cells in Hormone-supplemented Serum-free Medium," *Annals N.Y. Aca. Sci.* 383:44-68.

Morrison et al. (1984). "Chimeric Human Antibody Molecules: Mouse Antigen-binding Domains with Human Constant Region Domains," *Proc. Natl. Acad. Sci. USA* 81:6851-6855.

Müller et al. (Jan. 1, 2007). "Bispecific Antibodies," *Handbook of Therapeutic Antibodies*, Wiley-VCH, Weinham, pp. 345-378.

Muller et al (2000). "Processing and Sorting of the Prohormone Convertase 2 Propeptide," *J. Biol. Chem.* 275:39213-39222.

Murakami et al. (1995). "Cell Cycle Regulation, Oncogenes, and Antineoplastic Drugs" Chapter 1 in *The Molecular Basis of Cancer*, Mendelsohn and Israel, Philadelphia, W.B. Saunders, Philadelphia p. 13.

Muyldermas et al. (Apr. 2001). "Recognition of Antigens by Single-domain Antibody Fragments: the Superfluous Luxury of Paired Domains," *Trend Biochem. Sci.* 26(4):230-235.

Nicealous et al. (1994). Calicheamicin θ11:A Rationally Designed Molecule with Extremely Potent and Selective DNA Cleaving Properties and Apoptosis Inducing Activity, *Agnew Chem. Intl. Ed. Engl.* 33:183-186.

Niculescu-Duvaz et al. (1997). Antibody-directed Enzyme Prodrug Therapy (ADEPT): A Review, *Adv. Drg. Del. Rev.* 26:151-172 (1997).

Offner et al. (1991). "T Cell Receptor Peptide Therapy Triggers Autoregulation of Experimental Encephalomyelitis," *Science* 251:430-432.

Petitt et al. (1981). "Marine animal biosynthetic constituents for cancer chemotherapy," *J. Nat. Prod.* 44:482-485.

Petiti et al. (1997). "The Dolastatins," *Fortschr. Chem. Org. Naturst.* 70:1-79.

Pettit et al. (1998). "Antineoplastic Agents 360. Synthesis and Cancer Cell Growth Inhibitory Studies of Dolastatin 15 Structural Modifications," *Anti-Cancer Drug Design* 13:47-66.

Pettit et. al. (1998). "Specific Activities of Dolastatin 10 and Peptide Derivatives Against Cryptococcus Neoformans," *Antimirob. Agents Chemother.* 42:2961-2965.

Pluckthun. (1994). "Antibodies from *Escherichia coli*" Chapter 11 in *The Pharmacology of Monoclonal Antibodies: Handbook of Phannacology*, Rosenberg and Moore, eds., Berlin:Springer-Verlag, vol. 113, pp. 269-315.

Pluckthun et al. (1997). "New Protein Engineering Approaches to Multivalent and Bispecific Antibody Fragments," *Imunotechnology* 3(2):83-105.

Poncet (1999). "The Dolastatins, A Family of Promising Antineoplastic Agents," *Curr. Pharm. Des.* 5:139-162.

Presta (1992). "Antibody Engineering," *Curr. Op. Struct. Biol.* 2:593-596.

Presta et al. (1993). "Humanization of an Antibody Directed Against IgE," *J. Immunol.* 151:2623-2632.

Proba et al. (Jul. 4, 1995). "Functional Antibody Single-Chain Fragments From the Cytoplasm of *Escherichia coli*: Influence of Thioredoxin Reductase (TrxB)," *Gene* 159:203-207.

Ramm et al. (Jun. 2, 2001). "The Peroplasmic *Escherichia coli* Peptidylproly cis,trans-Isomerase FkpA," *J. Biol. Chem.* 275:17106-17113.

Ravetch et al. (1991). "Fc Receptors," *Annu. Rev. Immunol.* 9:457-492.

Riechmann et al (1988). "Reshaping Human Antibodies for Therapy," *Nature* 332:323-329.

Rowland et al (1986). "Drug Localisation and Growth Inhibition Studies of Vindesine-Monoclonal Anti-CEA Conjugates in a Human Tumour Xenograft," *Cancer Immunol. Immunother.* 21:183-187.

Rupert et al. (1993). "Cloning and Expression of Human $TAF_{II}250$: a TBP-associated Factor Implicated in Cell-cycle Regulation," *Nature* 362:175-179.

Santos et al. (Oct. 1999) "Generation and Characterization of a Single Gene-Encoded Single-chain-tetravalent Antitumor Antibody" *Clinical Cancer Research* 5(10 Suppl):3118s-3123s.

Shechter et al. (1976) "Selective Chemical Cleavage of Tryptophanyl Peptide Bonds by Oxidative Chlorination With N-Chlorosuccinimide," *Biochemistry* 15:5071-5075.

Schröder et al. (1965). "III. Formation of the Peptide Bond," *The Peptides*, vol. 1, Academic Press, New York, New York, pp. 76-136.

Siebenlist et al. (1980). "*E. coli* RNA Polymerase Interacts Homologously with Two Different Promoters," *Cell* 20:269-281.

Simmons et al. (2002). "Expression of Full-length Immunoglobulins in *Escherichia coli*: Rapid and Efficient Production of Aglycosylated Antibodies," *J. Immunol. Methods* 263:133-147.

Sims et al. (1993). "A Humanized CD18 Antibody Can Block Function Without Cell Destruction," *J. Immunol.* 151:2296-2308.

Steiner (1991). "The Biosynthesis of Biologically Active Peptides: A Perspective," Chapter 1 in *Peptide Biosynthesis and Processing*, Fricker ed., CRC Press, Boca Raton, FL, pp. 1-16.

Stella et al. (1985). "Prodrugs: A Chemical Approach to Target Drug Delivery" *Directed Drug Delivery*, Borchardt et al (ed.), Human Press, pp. 247-267.

Stites et al. (1994). "Immunoglobulin Protiens," Chapter 6 in *Basic Clinical Immunology*, 8th Edition, Appleton & Lange, Norwalk, CT, p. 71.

Syrigos et al. (1999). "Antibody Directed Enzyme Prodrug Therapy (ADEPT): A Review of the Experimental and Clinical Considerations," *Anticancer Research* 19:605-614.

Thorpe (1985) "Antibody Carriers of Cyotoxic Agents in Cancer Therapy: A Review," in *A Monoclonal Antibodies 84: Biological and Clinical Applications*, A. Pinchera et al (eds) pp. 475-506.

Urlaub et al. (1980). "Isolation of Chinese Hamster Cell Mutants Deficient in Dihydrofolate Reductase Activity," *Proc. Natl. Acad Sci USA* 77:4216.

Verhoeyen et al. (1988). "Reshaping Human Antibodies: Grafting an Antilysozyme Activity," *Science* 239:1534-1536.

Vitetta et al. (1987). "Redesigning Nature's Poisons to Create Anti-tumor Reagents," *Science* 238:1098.

Ward et al. (Oct. 12, 1989). "Binding Activities of a Repertoire of Single Immunoglobulin Variable Domains Secreted From *Escherichia coli*," *Nature* 341:544-546.

Wilman (1986). "Prodrugs in Cancer Chemotherapy," *Biochemical Society Transactions* 14:37-382, 615th Meeting Belfast.

Woyke et al. (Dec. 2001). "In Vitro Activities and Postantifungal Effects of the Potent Dolastatin10 Derivative Auristatin PHE," *Antimicrob. Agents and Chemother.* 45(12):3580-3584.

Wranik et al. (Dec. 21, 2012). "Luz-Y: A Novel Platform for the Mammalian Cell Production of Full-length IgG Bispeciic Antibodies," *Journal of Biological Chemistry* 287(52):43331-43339.

Yaniv. (1982). "Enhancing Elements for Activation of Eukaryotic Promoters," *Nature* 297:17-18.

Zapata et al. (1995). "Engineering Linear F(ab') 2 Fragments for Efficient Production in *Escherichia coli* and Enhanced Antiproliferative Activity," *Protein Eng.* 8(10):1057-1062.

Zhu et al. (1997). "Remodeling Domain Interfaces to Enhance Heterodimer Formation," *Protein Science* 6:781-788.

International Search Report mailed on Aug. 6, 2013, for PCT Application No. PCT/US2013/025365, filed Feb. 8, 2013, 6 pages.

(56) References Cited

OTHER PUBLICATIONS

Written Opinion mailed on Aug. 6, 2013, for PCT Application No. PCT/US2013/025365, filed Feb. 8, 2013, 9 pages.
Natsume et al. (Sep. 1, 2006). "Fucose Removal From Complex-type Oligosaccharide Enhances the Antibody-dependent Cellular Cytotoxicity of Single-gene-encoded Bispecific Antibody Comprising of Two Single-Chain Antibodies Linked to the Antibody Constant Region," *Journal of Biochemistry* 140(3):359-368.
U.S. Appl. No. 14/735,024, filed Jun. 9, 2015 for Christensen et al.
Aggarwal et al., (Jan. 22, 2008). "Fibroblast Activation Protein Peptide Substrates Identified from Human Collagen I Derived Gelatin Cleavage Sites," *Biochemistry* 47(3):1076-1086.
Anonymous. "Production in yeasts of stable antibody fragments," *Expert Opinion on Therapeutic Patents* 7(2):179-183, (1997).
Arndt, K.M. et al. (Sep. 7, 2001). "Helix-stabilized Fv (hsFv) antibody fragments: substituting the constant domains of a Fab fragment for a heterodimeric coiled-coil domain," *J. Mol. Biology* 312(1):221-228.
Atwell et al., "Stable heterodimers from remodeling the domain interface of a homodimer using a phage display library," *J. Mol. Biol.* 270 (1):26-35 (1997).
Ausubel et al., Short Protocols in Molecular Biology, Greene Publishing and Wiley Interscience, New York, New York, (Table of Contents), (1987).
Avgeris et al., "Kallikrein-related peptidase genes as promising biomarkers for prognosis and monitoring of human malignancies," *Biol. Chem* 391(5):505-511, (May 2010).
Bao et al., "HER2-mediated upregulation of MMP-1 is involved in gastric cancer cell invasion," *Arch Biochem Biophys* 499(1-2):49-55, (Jul. 2010).
Barbin et al. (Mar.-Apr. 2006). "Influence of Variable N-Glycosylation on the Cytolytic Potential of Chimeric CD19 Antibodies," *J. Immunother.* 29(2):122-133.
Barnes et al., "Advances in animal cell recombinant protein production: GS-NS0 expression system," *Cytotechnology* 32 (2):109-23 (Feb. 2000).
Barnes et al., "Characterization of the stability of recombinant protein production in the GS-NS0 expression system," *Biotechnol Bioeng.* 73(4):261-70 (May 2001).
Bera et al., "A bivalent disulfide-stabilized Fv with improved antigen binding to erbB2," *J. Mol. Biol.* 281(3):475-483, (Aug. 21, 1998).
Bird et al. (Oct. 21, 1988). "Single-Chain Antigen-Binding Proteins," *Science* 242(4877):423-6.
Bird et al. (Apr. 28, 1989). "Single-Chain Antigen-Binding Proteins," *Science* 244(4903):409, *Erratum.*
Boado et al., "IgG-single chain Fv fusion protein therapeutic for Alzheimer's disease: Expression in CHO cells and pharmacokinetics and brain delivery in the rhesus monkey," *Biotechnology and Bioengineering* 105(3):627-635, (Feb. 15, 2010).
Boerner et al., "Production of Antigen—Specific Human Monoclonal Antibodies From In Vitro-Primed Human Splenocytes," *J. Immunol.* 147(1):86-95, (Jul. 1991).
Borgström et al., "Complete Inhibition of Angiogenesis and Growth of Microtumors by Anti-Vascular Endothelial Growth Factor Neutralizing Antibody: Novel Concepts of Angiostatic Therapy from Intravital Videomicroscopy," *Cancer Research* 56:4032-4039, (1996).
Briggs et al., "Cystatin E/M suppresses legumain activity and invasion of human melanoma," *BMC Cancer* 10(17):1-13, (Jan. 2010).
Brinkmann. "Disulfide-stabilized Fv fragments," Chapter 14 in 2 in Antibody Engineering, Kontermann et al. eds., vol. 2, Springer-Verlag, Berlin Heidelberg, Germany, pp. 181-189, (Apr. 30, 2010).
Brinkmann et al., "A recombinant immunotoxin containing a disulfide-stabilized Fv fragment," *PNAS* 90(16):7538-7542, (1993).
Brorson et al., "Mutational Analysis of Avidity and Fine Specificity of Anti-Levan Antibodies," *J. Immunol.* 163:6694-6701 (1994).

Brüggemann et al., "Comparison of the effector functions of human immunoglobulins using a matched set of chimeric antibodies," *J Exp Med.* 166(5):1351-61, (Nov. 1987).
Brüggemann et al., "Designer Mice: The Production of Human Antibody Repertoires in Transgenic Animals," *Year in Immuno.* 7:33-40, (1993).
Brummell et al., "Probing the combining site of an anti-carbohydrate antibody by saturation-mutagenesis: role of the heavy-chain CDR3 residues," *Biochemistry* 32(4):1180-1187 (1993).
Brunhouse et al., "Isotypes of IgG: comparison of the primary structures of three pairs of isotypes which differ in their ability to activate complement," *Mol Immunol.* 16(11): 907-917 (Nov. 1979).
Budtschanow et al. "System of Humoral Immunity Antibodies (Theme 2)," Guidance Manual for General Immunology, Twer (2008) p. 3, English Translation, 3 pages, (5 pages both English Equivalent and Russian Reference.
Burgess et al. "Possible dissociation of the heparin-binding and mitogenic activities of heparin-binding (acidic fibroblast growth factor-1 from its receptor-binding activities by site-directed mutagenesis of a single lysine residue," *Journal of Cell Biology* 111:2129-2138, (Nov. 1990).
Burks et al., "In vitro scanning saturation mutagenesis of an antibody binding pocket," *PNAS* 94(2):412-417 (1997).
Burton et al., "The C1q Receptor Site on Immunoglobulin G," *Nature* 288(5789):338-344, (Nov. 27, 1980).
Caron et al., "Engineered humanized dimeric forms of IgG are more effective antibodies," *J. Exp. Med.* 176(4):1191-1195, (Oct. 1, 1992).
Carro et al., "Serum insulin-like growth factor I regulates brain amyloid-β levels," *Nature Medicine* 8(12):1390-1397, (2002, e-pub. Nov. 4, 2002).
Carter., "Bispecific human IgG by design," *Immunol. Methods* 248:7-15, (2001).
Chan, L.A. et al., "Variable Region Domain Exchange in Human IgGs Promotes Antibody Complex Formulation with Accompanying Structural Changes and Altered Effector Functions," *Molecular Immunology* 41(5):527-538. (2004).
Chernaia, "[Cathepsin L from human brain tumor. Purification and contents]." Ukr Biokhim Zh. 70(5):97-103, (Sep.-Oct. 1998). (English Translation of Abstract.) (Article in Russian).
Chitnis et al., "The type 1 insulin-like growth factor receptor pathway," *Clin. Cancer Res.* 14(20):6364-6370, (Oct. 16, 2008).
Chung et al., "Development of a novel albumin-binding prodrug that is cleaved by urokinase-type-plasminogen activator (uPA)," *Bioorg Med Chem Lett.* 16(19):5157-5163 (Oct. 1, 2006).
Cohen et al., "Nonchromosomal antibiotic resistance in bacteria: Genetic transformation of *Escherichia coli* by R-factor DNA," *Proc. Natl. Acad. Sci. USA* 69(8):2110-2114 (Aug. 1972).
Cole et al., "The EBV-hybridoma technique and its application to human lung cancer," *Monoclonal Antibodies and Cancer Therapy,* New York: Alan R. Liss, Inc. pp. 77-96 (1985).
Coleman., "Effects of amino acid sequence changes on antibody-antigen interactions," *Research in Immunol.* 145(1):33-38, (1994).
Coloma and Morrison., "Design and production of novel tetravalent bispecific antibodies," *Nature Biotechnology* 15(2):159-163 (Feb. 1997).
Cordingley et al., "Substrate requirements of human rhinovirus 3C protease for peptide cleavage in vitro," *J. Biol. Chem.* 265(16):9062-9065, (1990).
Cortesio et al. (Mar. 10, 2008). "Calpain 2 and PTP1B function in a novel pathway with Src to regulate invadopodia dynamics and breast cancer cell invasion," *J. Cell Biol.* 180(5):957-971.
Coxon et al., "Combined treatment of angiopoietin and VEGF pathway antagonists enhances antitumor activity in preclinical models of colon carcinoma," *99th AACR Annual Meeting,* Abstract #1113, (Apr. 2008).
Crawford et al., "Matrix metalloproteinase-7 is expressed by pancreatic cancer precursors and regulates acinar-to-ductal metaplasia in exocrine pancreas," *J. Clin. Invest.* 109(11):1437-1444, (Jun. 2002).
Cudic et al., "Extracellular proteases as targets for drug development," *Curr. Protein Pept Sci* 10(4):297-307, (Aug. 2009).

(56) References Cited

OTHER PUBLICATIONS

Cullen et al., "Granzymes in cancer and immunity," *Cell Death Differ* 17(4):616-623, (Apr. 2010).
Dall'Acqua, W. et al. (1998). "Contribution of Domain Interface Residues to the Stability of Antibody CH3 Domain Homodimers", *Biochemistry*, 37:9266-9273.
Davis et al. "SEEDbodies: Fusion Proteins Based on Strand-Exchange Engineered Domain (SEED) $C_H3$ Heterodimers in an Fc Analogue Platform for Asymmetric Binders or Immunofusions and Bispecific Antibodies," *Protein Engineering Design & Selection* 23(4):195-202, (2010, e-pub. Feb. 4, 2010).
Davies et al., "Expression of GnTIII in a recombinant anti-CD20 CHO production cell line: Expression of antibodies with altered glycoforms leads to an increase in ADCC through higher affinity for FcγRIII," *Biotechnol. Bioeng.* 74:288-294, (2001).
Deyev., "Multivalency: the hallmark of antibodies used for optimization of tumor targeting by design," *Bioessays* 30(9):904-918, (2008).
Deyev et al. "Modern Technologies for Creating synthetic Antibodies for clinical Application," *Acta Naturae* 1:32-50, (2009).
Dimmock, N.J. et al. (2004). "Valency of antibody binding to virions and its determination by surface plasmon resonance", *Rev. Med. Virol.*, 14:123-135.
Donaldson et al., "Design and development of masked therapeutic antibodies to limit off-target effects: Application to anti-EGFR antibodies," *Cancer Biology & Therapy* 8(22):2145-2150, (Nov. 15, 2009).
Dufner et al., "Harnessing phage and ribosome display for antibody optimization," *Trends Biotechol.* 24(11):523-29 (2006).
Durocher et al., "High-level and high-throughput recombinant protein production by transient transfection of suspension-growing human 293-EBNA1 cells," *Nucleic Acids Research* 30(2 e9):nine pages, (2002).
Edelman et al., "The covalent structure of an entire γG immunoglobulin molecule," *Proc. Natl. Acad. Sci. USA* 63:78-85, (1969).
Flatman et al., "Process analytics for purification of monoclonal antibodies," *J. Chromatogr B* 848:79-87, (2007).
Gadgil et al. (2006). "Identification of cysteinylation of a free cysteine in the Fab region of a recombinant monoclonal IgG1 antibody using lys-C limited proteolysis coupled with LC/MS analysis," *Analytical biochem.* 2006: 355:185-74.
Galamb et al., "Inflammation, adenoma and cancer: objective classification of colon biopsy specimens with gene expression signature," *Dis Markers* 25(1):1-16, (2008).
Geisse et al., "Eukaryotic expression systems: A comparison," *Protein Expression and Purification* 8:271-282 (1996).
Gerspach et al., "Target-selective activation of a TNF prodrug by urokinase-type plasminogen activator (uPA) mediated proteolytic processing at the cell surface," *Cancer Immunol. Immunother* 55:1590-1600 (2006).
Gold et al., "A novel bispecific, trivalent antibody construct for targeting pancreatic carcinoma," *Cancer Res.* 68(12):4819-4826, (2008).
Goldenberg et al., "Bi-Specific Antibodies that Bind Specific Target Tissue and Targeted Conjugates," Derwent Information Ltd., 12 pages, (2012).
Goodman et al (1994). Chapter 6: Basic and Clinical Immunology, 8th edition, Appleton & Lange, Norwalk, CT, pp. 66-79.
Grönwall C. et al. (Jun. 2008). "Generation of Affibody ligands binding interleukin-2 receptor alpha/CD25," *Biotechnol. Appl. Biochem.* 50(Pt. 2):97-112.
Graham et al., "A new technique for the assay of infectivity of human adenovirus 5 DNA," *Virology* 52 (2):456-467, (1973).
Greenwood et al. "Structural Motifs Involved in Human IgG Antibody Effector Functions,". *Eur. J. Immunology* 23(5):1098-1104, (May 1993).
Grote et al., "Bispecific Antibody Derivatives Based on Full-Length IgG Formats," Chapter 16 in *Methods in Molecular Biology* 901:247-263, (2012).

Gunasekaran et al., "Enhancing antibody Fc heterodimer formation through electrostatic steering effects: Applications to bispecific molecules and monovalent IgG," *The Journal of Biological Chemistry* 285(25):19637-19646, (Jun. 18, 2010).
Hamers-Casterman et al. (1993). "Naturally occurring antibodies devoid of light chains," *Nature* 363:446-448.
Hartog et al., "The Insulin-like growth factor 1 receptor in cancer: Old focus, new future," European Journal of Cancer, Pergamon Press, Oxford, GB, 43(13):1895-1904, (Aug. 23, 2007).
Henry et al., "Clinical implications of fibroblast activation protein in patients with colon cancer," *Clin Cancer Res.* 13(6):1736-1741, (Mar. 15, 2007).
Hezareh et al., "Effector Function Activities of a Panel of Mutants of a Broadly Neutralizing Antibody against Human Immunodeficiency Virus Type 1," *Journal of Virology* 75(24):12161-12168, (Dec. 2001).
Hollander., "Bispecific antibodies for cancer therapy," *Immunotherapy* 1(2):211-222, (Mar. 2009).
Holliger et al., "Engineered antibody fragments and the rise of single domains," *Nat Biotechnol.* 23(9):1126-1136, (Sep. 2005).
Hoogenboom and Winter., "By-passing immunisation. Human antibodies from synthetic repertoires of germline $V_H$ gene segments rearranged in vitro," *J Mol Biol.* 227 (2):381-388, (Sep. 20, 1992).
Hust et al., "Single Chain Fab (scFab) Fragment," *BMC Biotechnology* 7(14):1-15, (Mar. 8, 2007).
Huston, J.S. et al. (1993). "Medical Applications of Single-Chain Antibodies," *Intern. Rev. Immunol.* 10(2-3):195-217.
Huston et al. (Aug. 1988). "Protein Engineering of Antibody Binding Sites: Recovery of Specific Activity in an Anti-Digoxin Single-Chain Fv Analogue Produced in *Escherichia coli,*" *Proc. Natl. Acad. Sci. U.S.A.* 85(16):5879-5883.
Ibragimova et al., "Stability of the β-Sheet of the WW domain: A molecular dynamics simulation study," *Biophysical Journal* 77:2191-2198, (Oct. 1999).
Idusogie et al., "Mapping of the C1q binding site on rituxan, a Chimeric antibody with a human IgG1 Fc," *The Journal of Immunology* 164:4178-4184, (2000).
International Search Report mailed on Dec. 6, 2011, for PCT Patent Application No. PCT/EP2011/064476 filed on Aug. 23, 2011, seven pages. (149.40).
International Search Report mailed on Dec. 6, 2011, for PCT Patent Application No. PCT/EP2011/064468 filed on Aug. 23, 2011, seven pages. (150.40).
Jakobovits et al., "Analysis of Homozygous Mutant Chimeric Mice: Deletion of the Immunoglobulin Heavy-Chain Joining Region Blocks B-cell Development and Antibody Production," *Proc. Natl. Acad. Sci. USA* 90(6) :2551-2555, (Mar. 15, 1993).
Jakobovits et al., "Germ-line Transmission and Expression of a Human-derived Yeast Artificial Chromosome," *Nature* 362:255-258, (Mar. 1993).
Jang et al., "The structural basis for DNA binding by an anti-DNA autoantibody," *Mol. Immunol.* 35(18):1207-1217 (1998).
Jefferis et al., "IgG-Fc-mediated effector functions: molecular definition of interaction sites for effector ligands and the role of glycosylation," *Immunol Rev.* 163:59-76, (1998).
Jendreyko et al., "Simultaneous, Phenotypic Knockout of VEGF-R2 and Tie-2 With an Intradiabody Enhances Antiangiogenic Effects In Vivo," Therapieoptimierung und Risikostratifizierung, Scripps Research Institute, 218:143-151, (2006).
Jia et al., "A novel trifunctional IgG-like bispecific antibody to inhibit HIV-1 infection and enhance lysis of HIV by targeting activation of complement," *Virology Journal* 7(142):1-4, (Jun. 29, 2010).
Johnson et al., "Kabat Database and its applications: 30 years after the first variability plot," *Nucleic Acids Research* 28(1) :214-218, (2000).
Johnson et al. (1991). "Construction of Single-Chain Fv Derivatives Monoclonal Antibodies and Their Production in *Escherichia coli,*" *Methods Enzymol.* 203:88-98.
Johnson et al. (2003). "The Kabat Database and a Bioinformatics Example," Chapter 2 in *Methods in Molecular Biology*, Lo, B.K.C, Humana Press, Totawa, N.J., 248:11-25.

(56) References Cited

OTHER PUBLICATIONS

Kabat et al., "Evolutionary and structural influences on light chain constant ($C_L$) region of human and mouse immunoglobulins," *Proc. Natl. Acad. Sci. USA* 72(7):2785-2788, (Jul. 1975).

Kabat et al., Sequences of Proteins of Immunological Interest (Table of Contents and Introduction), 5th edition, Bethesda, MD: Public Health Service, NIH, vol. 1, (1991).

Karadag et al., "ADAM-9 (MDC-9/meltrin-γ), a member of the a disintegrin and metalloproteinase family, regulates myeloma-cell-induced interleukin-6 production in osteoblasts by direct interaction with the αvβ5 integrin," *Blood* 107(8):3271-3278, (Apr. 2006).

Kaufman., "Overview of Vector Design for Mammalian Gene Expression," *Molecular Biotechnology* 16:151-160, (2000).

Kazama et al., "Hepsin, a putative membrane-associated serine protease, activates human factor VII and initiates a pathway of blood coagulation on the cell surface leading to thrombin formation," *JBC* 270:66-72, (1995).

Kim et al., "Inhibition of Vascular Endothelial Growth Factor-Induced Angiogenesis Suppresses Tumour Growth In Vivo," *Nature* 362:841-844, (1993).

Kleinschmidt et al., "Design of a modular immunotoxin connected by polyionic adapter peptides," *J. Mol. Biol.* 327(2):445-452, (Mar. 21, 2003).

Kobayashi et al., "Similarities in the Biodistribution of Iodine-Labeled Anti-Tac Single-Chain Disulfide-Stabilized Fv Fragment and Anti-Tac Disulfide-Stabilized Fv Fragment," *Nuclear Medicine & Biology* 25:387-393, (1998).

Kobayshi et al. "Tryptophan H33 plays an important role in pyrimidine (6-4) pyrimidone photoproduct binding by a high-affinity antibody," *Protein Engineering* 12(10):879-844 (1999).

Kodukula et al., "Biosynthesis of phosphatidylinositol glycan-anchored membrane proteins. Design of a simple protein substrate to characterize the enzyme that cleaves the COOH-terminal signal peptide," *The Journal of Biological Chemistry* 266(7):4464-4470 (Mar. 5, 1991).

Krugmann et al. "Structural Requirements for Assembly of Dimeric IgA Probed by Site-Directed Mutagenesis of J Chain and a Cysteine Residue of the α-chain CH2 Domain," *The Journal of Immunology* 159:244-249, (1997).

Lamkanfi et al., "Inflammasomes: guardians of cytosolic sanctity," *Immunol. Rev.* 227(1):95-105, (Jan. 2009).

Lazar et al., "Transforming growth factor α: Mutation of aspartic acid 47 and leucine 48 results in different biological activities," *Molecular and Cellular Biology* 8(3):1247-1252, (Mar. 1988).

Lee et al. (1999). "Generation and Characterization of a Novel Single-Gene-Encoded Single-Chain Immunoglobulin Molecule With Antigen Binding Activity and Effector Functions" *Mol Immunol.* 36(1):61-71.

Lee et al., "Using substrate specificity of antiplasmin-cleaving enzyme for fibroblast activation protein inhibitor design," *Biochemistry* 48(23):5149-5158, (Jun. 16, 2009).

Leeman et al., "The Structure, Regulation, and Function of Human Matrix Metalloproteinase-13," *Crit. Rev Biochem Mol. Biol.* 37(3):149-166, (2002).

Lifely et al., "Glycosylation and Biological Activity of CAMPATH-1H Expressed in Different Cell Lines and Grown Under Different Culture Conditions," *Glycobiology* 5(8):813-822, (Dec. 1995).

Lin et al., "Structure-Function relationships in glucagon: Properties of highly purified des-his-, monoiodo-, and [Des-Asn$^{28}$, Thr$^{29}$](homoserine lactone$^{27}$)-glucagon," *Biochemistry USA* 14:1559-1563, (1975).

Liang et al., "Cross-species Vascular Endothelial Growth Factor (VEGF)-blocking Antibodies Completely Inhibit the Growth of Human Tumor Xenografts and Measure the Contribution of Stromal VEGF," *Journal of Biological Chemistry* 281(2):951-961, (2006).

Liotta et al., "Metastatic potential correlates with enzymatic degradation of basement membrane collagen," *Nature* 284(5751) 67-68, (Mar. 6, 1980).

Liu et al., "Clinical and imaging diagnosis of primary hepatic lymphoma," *J First Mil Med. Univ*, 25(10):1290-1292, three pages, (2005). (Translation of the Abstract Only.).

Lopez-Otin et al., "The regulatory crosstalk between kinases and proteases in cancer," *Nat. Rev. Cancer* 10(4):278-292, (Apr. 2010).

Love et al., "Recombinant antibodies possessing novel effector functions," *Methods in Enzymology* 178:515-527, (1989).

Lu et al., "A Fully Human Recombinant IgG-Like Bispecific Antibody to Both the Epidermal growth Factor Receptor and the Insulin-Like Growth Factor Receptor for Enhanced Antitumor Activity," *The Journal of Biological Chemistry* 280(20):19665-19672, (May 20, 2005).

Lu et al. (2002). "Fab-scFv Fusion Protein: an Efficient Approach to Production of Bispecific Antibody Fragments" *J. Immunol Methods* 267(2):213-26.

Lu et al., "Simultaneous blockage of both the epidermal growth factor receptor and the insulin-like growth factor receptor signaling pathways in cancer cells with a fully human recombinant bispecific antibody" J. Biol. Chem. 279(4):2856-65 (2004).

Lu et al. (2004. E-pub. Apr. 22, 2004). "The Effect of Variable Domain Orientation and Arrangement on the Antigen-Binding Activity of a Recombinant Human Bispecific Diabody" *Biochem. Biophys. Res. Commun.* 318(2):507-513.

Lu et al., "ADAMTS1 and MMP1 proteolytically engage EGF-like ligands in an osteolytic signaling cascade for bone metastasis," *Genes Dev.* 23(16):1882-1894, (Aug. 2009).

Lukas et al., "Inhibition of C1-Mediated Immune Hemolysis by Monomeric and Dimeric Peptides from the Second Constant Domain of Human Immunoglobulin G," *The Journal of Immunology* 127(6):2555-2560, (Dec. 1981).

Lund et al., "Oligosaccharide-protein interactions in IgG can modulate recognition by Fcγ receptors," *FASEB Journal* 9:115-119, (1995).

Makrides., "Components of Vectors for Gene Transfer and Expression in Mammalian Cells," *Protein Expression and Purification* 17:183-202, (1999).

Mamoune et al., "Calpain-2 as a target for limiting prostate cancer invasion," *Cancer Res.* 63(15):4632-4640, (Aug. 2003).

Marks et al., "By-Passing Immunization: Human Antibodies From V-gene Libraries Displayed on Phage," *J Mol Biol.* 222(3):581-597, (Dec. 5, 1991).

Marvin et al., "Recombinant approaches to IgG-like bispecific antibodies," *Acta Pharmacol. Sin.* 26:649-658, (2005).

Mason et al. (2004). "Coiled Coil Domains: Stability, Specificity, and Biological Implications," *ChemBioChem* 5:170-176.

Matrisian. "Cancer biology: extracellular proteinases in malignancy," *Curr. Biol.* 9(20):R776-R778, (Oct. 1999).

McLean, G.R. et al. (2005). "A point mutation in the CH3 domain of human IgG3 inhibits antibody secretion without affecting antigen specificity", *Molecular Immunology*, 42:1111-1119.

Meissner et al., "Transient Gene Expression: Recombinant Protein Production with Suspension-Adapted HEK293-EBNA Cells," *Biotechnology and Bioengineering* 75:197-203, (2001).

Melnyk et al., "Vascular Endothelial Growth Factor Promotes Tumor Dissemination by a Mechanism Distinct from Its Effect on Primary Tumor Growth," *Cancer Research* 56:921-924, (1996).

Merchant et al., "An efficient route to human bispecific IgG," *Nature Biotechnology* 16:677-681, (1998).

Michaelson et al., "Anti-tumor activity of stability-engineered IgG-like bispecific antibodies targeting TRAIL-R2 and LTβR," *MAbs* 1(2):128-141, (Mar. 2009, e-pub. Mar. 11, 2009).

Milstein et al., "Hybrid Hybridomas and Their Use in Immunohistochemistry," *Nature* 305:537-540, (Oct. 6, 1983).

Miller et al., "Design, Construction, and In Vitro Analyses of Multivalent Antibodies," *J. Immunol.* 170:4854-4861, (2003).

Mimura et al., "Role of Oligosaccharide Residues of IgG1-Fc in FcγRIIb Binding," *The Journal of Biological Chemistry* 276(49): 45539-45547, (Dec. 7, 2001).

Minn et al., "Genes that Mediate Breast Cancer Metastasis to Lung," *Nature* 436(7050):518-524, (Jul. 2005).

Mirny, L. et al. (2001). "Protein Folding Theory: From Lattice to All-Atom Models", *Annu. Rev. Biophys. Biomol. Struct.*, 30:361-96.

(56) References Cited

OTHER PUBLICATIONS

Morgan et al., "The N-terminal End of the $C_H2$ Domain of Chimeric Human IgG1 anti-HLA-DR is Necessary for C1q, FcγRI and FcγRIII Binding," *Immunology* 86:319-324, (1995).

Morrison et al., "Variable region domain exchange influences the functional properties of IgG," *Journal of Immunology, American Association of Immunologists* 160:2802-2808, (Jan. 1, 1998).

Morrison. "Two Heads are Better than One," *Nature Biotechnology* 25(11):1233-1234, (Nov. 2007).

Morrison. "Success in Specification," *Nature* 368:812-813, (Apr. 1994).

Müller et al., "Recombinant Bispecific Antibodies for Cellular Cancer Immunotherapy," *Current Opinion in Molecular Therapeutics* 9:319-326, (2007).

Müller et al., "The first constant domain ($C_H1$ and $C_L$) of an antibody used as heterodimerization domain for bispecific miniantibodies," *FEBS Letters* 422:259-264, (1998).

Mukhopadhyay et al., "Matrix metalloproteinase-12 is a therapeutic target for asthma in children and young adults," *J. Allergy Clin Immunol.* 126:70-76, (2010).

Netzel-Arnett et al., "Sequence Specificities of Human Fibroblast and Neutrophil Collagenases," *J. Biol. Chem.* 266(11):6747-6755, (Apr. 15, 1991).

Netzel-Arnett et al., "Comparative sequence specificities of human 72- and 92-kDa gelatinases (type IV collagenases) and PUMP (matrilysin)," *Biochemistry* 32(25):6427-6432, (Jun. 29, 1993).

Neuberger et al., "A hapten-specific chimeric IgE antibody with human physiological effector function," *Nature* 314:268-270, (Mar. 21, 1985).

Nieri et al. (Feb. 1, 2009). "Antibodies for Therapeutic Uses and the Evolution of Biotechniques," *Current Med. Chem.* 16(6):753-779.

Nilsson et al. (1987). "A synthetic IgG-binding domain based on staphylococcal protein A," *Prot. Eng.* 1:107-133.

Nord et al. (1995). "A combinatorial library of an α-helical bacterial receptor domain,"*Prot. Eng.* 8:601-608.

Nord et al. (1997). "Binding proteins selected from combinatorial libraries of an α-helical bacterial receptor domain," *Nat. Biotech.* 15:772-777.

Niwa et al., "IgG subclass-independent improvement of antibody-dependent cellular cytotoxicity by fucose removal from $Asn^{297}$-linked oligosaccharides," *J. Immunol. Methods* 306:151-160, (2005).

Norderhaug et al., "Versatile Vectors for Transient and Stable Expression of Recombinant Antibody Molecules in Mammalian Cells," *Journal of Immunological Methods* 204:77-87, (1997).

Novotný, J. et al. "Structural invariants of antigen binding: Comparison of immunoglobulin $V_L$-$V_H$ and $V_L$·$V_L$ domain dimmers", *Proc. Natl. Acad. Sci. USA*, 82:4592-4596, (1985).

Ohno et al., "Antigen-binding specificities of antibodies are primarily determined by seven residues of $V_H$," *Proc. Natl. Acad. Sci. USA* 82(9):2945-2949, (May 1985).

Oliner et al., "Suppression of Angiogenesis and Tumor Growth by Selective Inhibition of Angiopoietin-2," *Cancer Cell* 6:507-516, (2004).

Orcutt, et al., "A modular IgG-scFv bispecific antibody topology," *Protein Engineering, Design & Selection* 23(4):221-228, (Apr. 2010, e-pub. Dec. 17, 2009).

Orlandi et al., "Cloning Immunoglobulin Variable Domains for Expression by the Polymerase Chain Reaction," *Proc. Natl. Acad. Sci. USA* 86:3833-3837, (May 1989).

O'Shea et al. "Peptide 'Velcro': design of a heterodimeric coiled coil," *Current Biology* 3(10):658-667, (1993).

Pace et al., "How to Measure and Predict the Molar Absorption Coefficient of a Protein," *Protein Science* 4(11): 2411-2423, (Nov. 1995).

Pakula et al., "Genetic analysis of protein stability and function," *Annu. Rev. Genet.* 23:289-310, (1989).

Pan et al. (Jan. 2007). "Blocking Neuropilin-1 Function Has an Additive Effect with Anti-VEGF to Inhibit Tumor Growth," *Cancer Cell* 11:53-67.

Pleass et al. (Aug. 13, 1999). "Identification of Residues in the CH2/CH3 Domain Interface of IgA Essential for Interaction With the Human fcα Receptor (Fcα R) CD89," *The Journal of Biology Chemistry* 274(33):23508-23514.

PreScission Protease, GE Healthcare Catalogue No. 27-0843-01, located at http://www.gelifesciences.com/webapp/wcs/stores/servlet/productById/en/GELifeScience, last visited on Jul. 10, 2013, one page.

Radaev et al., "Recognition of IgG by Fcγ Receptor," *The Journal of Biological Chemistry* 276(19): 16478-16483, (May 11, 2001).

Rajagopal et al., "A Form of Anti-Tac(Fv) Which is Both Single-chain and Disulfide Stabilized: Comparison with its single-chain and Disulfide-stabilized Homologs," *Protein Engineering* 10(12):1453-1459, (1997).

Raju. "Glycosylation Variations with Expression Systems and Their Impact on Biological Activity of Therapeutic Immunoglobulins," *BioProcess International* 1(4): 44-53, (Apr. 2003).

Rawlings., "A large and accurate collection of peptidase cleavages in the *MEROPS* database," Database (Oxford), pp. 1-14, (2009, e-pub. Nov. 2, 2009).

Reiter et al. (1994). "Stabilization of the Fv Fragments in Recombinant Immunotoxins by Disulfide Bonds Engineered into Conserved Framework Regions," *Biochemistry* 33(18):5451-5449.

Reiter et al. (Jul. 15, 1994). "Improved Binding and Antitumor Activity of a Recombinant Anti-erbB2 Immunotoxin by Disulfide Stabilization of the Fv Fragment," *J. Biol. Chem.* 269(28):18327-18331.

Reiter et al. (May 1994). "Engineering Interchain Disulfide Bonds Into Conserved Framework Regions of Fv Fragments: Improved Biochemical Characteristics of Recombinant Immunotoxins Containing Disulfide-Stabilized Fv," *Protein Eng.* 7(5):697-704.

Reiter et al., "Cytotoxic and antitumor activity of a recombinant immunotoxin composed of disulfide-stabilized anti-Tac Fv fragment and truncated *Pseudomonas* exotoxin," *International Journal of Cancer* 58:142-149, (1994).

Reiter et al., "Antitumor activity and pharmacokinetics in mice of a recombinant immunotoxin containing a disulfide-stabilized Fv fragment," *Cancer Research* 54:2714-2718, (1994).

Reiter et al., "Antibody engineering of recombinant Fv immunotoxins for improved targeting of cancer: disulfide-stabilized Fv immunotoxins," *Clin. Cancer Res.* 2(2):245-252, (Feb. 1, 1996).

Reiter et al., "Disulfide stabilization of antibody Fv: computer predictions and experimental evaluation," *Protein Engineering* 8:1323-1331, (1995).

Reiter et al., "Construction of a functional disulfide-stabilized TCR Fv indicates that antibody and TCR Fv frameworks are very similar in structure," *Immunity* 2:281-287, (1995).

Reiter et al., "Engineering antibody Fv fragments for cancer detection and therapy: disulfide-stabilized Fv fragments," *Nature Biotechnology* 14:1239-1245, (1996).

Ridgway et al., "'Knobs-into-holes' Engineering of antibody $C_H3$ domains for heavy chain heterodimerization," *Protein Engineering* 9(7):617-621, (1996).

Roitt et al., "Immunology," English Translation by McElroy Translation Company, Moscow "Mir" (2000), p. 110-111, eight pages.

Roitt A. et al. "Multispecific Antibodies Comprising Full Length Antibodies and Single Chain Fab Fragments," *Immunology*, English Translation, Moscow:Mir, pp. 388-389, (2000).

Rossi, E.A. et al., "Multivalent Anti-CD20/Anti-CD22 Bispecific Antibody Fusion Proteins Made by the DNL Method Show Potent Lymphoma Cytotoxicity," *Blood, American Society of Hematology* 8:11, pp. 707A, (2006).

Routier et al., "The Glycosylation Pattern of a Humanized IgGI Antibody (D1.3) Expressed in CHO Cells," *Glycoconjugate Journal* 14:201-207, (1997).

Ruppert et al., "Protease levels in breast, ovary and other gynecological tumor tissues: prognostic importance in breast cancer," *Cancer Detect. Prev.* 21(5):452-459, (1997).

Sambrook et al., Molecular Cloning: A Laboratory Manual "The Table of Contents" Cold Spring Harbor, New York: Cold Spring Harbor Laboratory Press, (1989).

(56) References Cited

OTHER PUBLICATIONS

Schaefer et al., "Immunoglobulin domain crossover as a generic approach for the production of bispecific IgG antibodies," *Proc. Natl. Acad. Sci. U.S.A.* 108(27):11187-11192, (Jul. 5, 2011, e-pub. Jun. 20, 2011).
Schirrmann et al. (Jan./Feb. 2010). "Oligomeric Forms of Single Chain Immunoglobulin (scIgG)," *Landes Bioscience* 2(1):73-76.
Schlaeger., "The Protein Hydrolysate, Primatone RL, is a Cost Effective Multiple Growth Promoter of Mammalian Cell Culture in Serum-containing and Serum-free Media and Displays Anti-apoptosis Properties," *Journal of Immunological Methods* 194:191-199, (1996).
Schlaeger et al., "Transient Gene Expression in Mammalian Cells Grown in Serum-free Suspension Culture," *Cytotechnology* 30:71-83, (1999).
Schmidt et al., "Suppression of Metastasis Formation by a Recombinant Single Chain Antibody-Toxin Targeted to Full-length and Oncogenic Variant EGF Receptors," *Oncogene* 18:1711-1721, (1999).
Schmiedl et al., "Expression of a bispecific dsFv-dsFy' antibody fragment in *Escherichia coli*," *Protein Engineering* 13(10):725-734, (Oct. 2000).
Schoonjans, et al., "Fab Chains as an Efficient Heterodimerization Scaffold for the Production of Recombinant Bispecific and Trispecific Antibody Derivatives," *Journal of Immunology* 165:7050-7057, (2000).
Schoonjans et al. (2000). "Efficient Heterodimerization of Recombinant Bi- and Trispecific antibodies" *Bioseparation* 9(3):179-183.
Schwartz et al., "A superactive insulin: (B10-aspartic acid]insulin(human)," *Proc. Natl. Acad. Sci. USA* 84:6408-6411, (Sep. 1987).
Scott et al., "Biologic protease inhibitors as novel therapeutic agents," *Biochimie* 92(11):1681-1688, (Nov. 2010).
Shen et al., "Single variable domain antibody as a versatile building block for the construction of IgG-like bispecific antibodies," *Journal of Immunological Methods* 318:65-74, (2007).
Shen et al., "Single variable domain-IgG fusion: A novel recombinant approach to Fc domain-containing bispecific antibodies," *J. of Biological Chemistry* 281(16):10706-10714, (Apr. 21, 2006, e-pub. Feb. 15, 2006).
Shields et al., "High Resolution Mapping of the Binding Site on Human IgG1 for FcγRI, FcγRII, FcγRIII and FcRn and Design of IgG1 Variants with Improved Binding to the FcγR," *Journal of Biological Chemistry* 276 (9):6591-6604, (2001).
Shields et al., "Lack of Fucose on Human IgG1 N-Linked Oligosaccharide Improves Binding to Human FcγRIII and Antibody-dependent Cellular Toxicity," *J Biol Chem.* 277(30):26733-26740, (Jul 26, 2002).
Sheriff et al. (1996). "Redefining the minimal antigen-binding fragment," *Nature Struct. Biol.* 3:733-736.
Shinkawa et al., "The Absence of Fucose but Not the Presence of galactose or Bisecting N-Acetylglucosamine of Human IgG1 Complex-Type Oligosaccharides Shows the Critical Role of Enhancing Antibody-Dependent Cellular cytotoxicity," *J. Biol. Chem.* 278 (5) 3466-3473, (2003).
Simon et al., "Antibody Domain Mutants Demonstrate Autonomy of the Antigen Binding Site," *The EMBO Journal* 9(4):1051-1056, (1990).
Singer, M. and Berg, P. "Genes and genomes," Moscoer, MIR 1(1998) 63-64 (With English Translation.).
Stetler-Stevenson et al., "Progelatinase A activation during tumor cell invasion," *Invasion Metastasis* 14(1-6):259-268, (1994-1995).
Stevenson et al., "A chimeric antibody with dual Fc regions (*bis*FabFc) prepared by manipulations at the IgG hinge," *Anti-cancer Drug Des.* 3(4):219-230, (Mar. 1989).
Stork et al. (Nov. 2007, e-pub. Nov. 3, 2007 ). "A Novel Tri-Functional Antibody Fusion Protein With Improved Pharmacokinetic Properties Generated by Fusing a Bispecific Single-Chain Diabody With an Albumin-Binding Domain From Streptococcal Protein G," *Protein Eng. Des. Sel.* 20(11):569-576.

Tao et al. (Apr. 1991). "The Differential Ability of Human IgG1 and IgG4 to Activate Complement is Determined by the COOH-terminal Sequence of the $C_H2$ Domain," *J. Exp. Med* 173:1025-1028.
Thie et al. (Jul. 22, 2009). "Multimerization Domains for Antibody Phage Display and Antibody Production," *New Biotech.* 26(6):314-321.
Thommesen et al., "Lysine 322 in the human IgG3 CH2 domain is crucial for antibody dependent complement activation," *Molecular Immunology* 37:995-1004, (2000).
Torres, M. et al. (2005). "Variable-Region-Identical Antibodies Differing in Isotype Demonstrate Differences in Fine Specificity and Idiotype", *The Journal of Immunology*, 174:2132.
Tripathi et al., "Laminin-332 is a substrate for hepsin, a protease associated with prostate cancer progression," *JBC* 283:30576-30584, (2008).
Umaña et al., "Engineered Glycoforms of an Antineuroblastoma IgG1 with Optimized Antibody-Dependent Cellular Cytotoxic Activity," *Nature Biotechnology* 17(2):176-180 (Feb. 1999).
Van Dijk and Van De Winkel., "Human antibodies as next generation therapeutics," *Curr Opin Chem Biol.* 5(4): 368-74, (Aug. 2001).
Van Spriel et al., "Immunotherapeutic perspective for bispecific antibodies," *Immunology Today* 21(8):391-397, (Aug. 2000).
Van't Veer et al., "Gene expression profiling predicts clinical outcome of breast cancer," *Nature* 415(6871):530-536, (Jan. 2002).
Vazquez-Ortiz et al., "Overexpression of cathepsin F, matrix metalloproteinases 11 and 12 in cervical cancer," *BMC Cancer* 5:68, (Jun. 30, 2005).
Velasco et al., "Human cathepsin O. Molecular cloning from a breast carcinoma, production of the active enzyme in *Escherichia coli*, and expression analysis in human tissues," *J. Biol Chem* 269(43):27136-27142, (Oct. 28, 1994).
Veveris-Lowe et al., "Seminal Fluid Characterization for Male Fertility and Prostate Cancer: Kallikrein-Related Serine Proteases and whole Proteome Approaches," *Semin Thromb Hemost.* 33(1):87-99, (2007).
Vijayalakshmi., "Antibody Purification Methods," *Applied Biochemistry and Biotechnology* 75:93-102, (1998).
Walker et al., "Efficient and Rapid Affinity Purification of Proteins Using Recombinant Fusion Proteases," *Bio/Technology* 12:601-605, (1994).
Walker et al. (Jun. 5, 2009, e-pub. Apr. 16, 2009). "Efficient Recovery of High-Affinity Antibodies From a Single-Chain Fab Yeast Display Library," *J. Mol. Biol.* 389(2):365-375.
Warren et al., "Regulation of Vascular Endothelial Growth Factor of Human Colon Cancer Tumorigenesis in a Mouse Model of Experimental Liver Metastasis," *J. Clin. Invest.* 95:1789-1797, (1995).
Webber et al., "Preparation and characterization of a disulfide-stabilized Fv fragment of the anti-Tac antibody: comparison with its single-chain analog," *Molecular Immunology* 32:249-258, (1995).
Werner et al., "Appropriate Mammalian Expression Systems for Biopharmaceuticals," *Drug Research* 48(8):870-880, (1998).
Wielockx et al., "Matrilysin (matrix metalloproteinase-7): a new promising drug target in cancer and inflammation?," *Cytokine Growth Factor Rev.* 15(2-3):111-115, (Apr.-Jun. 2004).
Willems et al., "Optimizing expression and purification from cell culture medium of trispecific recombinant antibody derivatives," *Journal of Chromatography B* 786:161-176, (2003).
Wilman. (1986). "Prodrugs in Cancer Chemotherapy," *Biochemical Society Transactions* 14:37-382, 615th Meeting Belfast, 8 pages.
Woof et al., "Human antibody-FC receptor interactions illuminated by crystal structures," *Nat. Rev. Immunol.* 4:1-11, (2004).
Wright et al., "ADAM28: a potential oncogene involved in asbestos-related lung adenocarcinomas," *Genes Chromosomes Cancer* 49(8);688-698, (Aug. 2010).
Wright and Morrison, "Effect of Glycosylation on Antibody Function: Implications for Genetic Engineering," *Trends in Biotechnology* 15:26-32, (1997).
Written Opinion of the International Searching Authority mailed on Dec. 6, 2011, for PCT Patent Application No. PCT/EP2011/064476 filed on Aug. 23, 2011, four pages.
Written Opinion of the International Searching Authority mailed on Dec. 6, 2011, for PCT Patent Application No. PCT/EP2011/064468 filed on Aug. 23, 2011, four pages.

(56) References Cited

OTHER PUBLICATIONS

Wu et al., "Simultaneous Targeting of Multiple Disease Mediators by a Dual-Variable-Domain Immunoglobulin," *Nature Biotechnology* 25(11):1290-1297, (Nov. 2007).
Xie et al., "A New format of bispecific antibody: Highly efficient heterodimerization, expression and tumor cell lysis," *J. of Immunol. Methods* 296:95-101, (2005).
Xu et al. (2000). "Diversity in the CDR3 region of V(H) is sufficient for most antibody specificities," *Immunity* 13:37-45.
Zeidler et al., "Simultaneous activation of T cells and accessory cells by a new class of intact bispecific antibody results in efficient tumor cell killing," *Journal of Immunology* 163:1246-1252, (1999).
Zuo et al., "An efficient route to the production of an IgG-like bispecific antibody," *Protein Engineering* 13(5):361-367, (2000).
Extended European Search Report mailed on Aug. 5, 2013, for European Patent Application No. 10817575.3, eleven pages.
International Preliminary Report on Patentability for PCT/EP2011/054505, mailed on Oct. 2, 2012, filed on Mar. 24, 2011, 8 pages.
International Preliminary Report on Patentability mailed on Aug. 21, 2014, for PCT Patent Application No. PCT/US2013/025365, filed on Feb. 8, 2013, 11 pages.
International Search Report mailed on Jun. 15, 2011 for PCT Patent Application No. PCT/US2010/002546 filed on Sep. 16, 2010, five pages.
International Search Report for PCT/EP2011/054505 mailed on Jun. 28, 2011, filed on Mar. 24, 2011, 7 pages.
Written Opinion of the International Searching Authority mailed on Jun. 15, 2011 for PCT Patent Application No. PCT/US2010/002546 filed on Sep. 16, 2010, seven pages.
Chilean Office Action dated Jan. 11, 2012, for Chilean Application No. 3781-2008, 19 pages.
Chilean Office Action dated Aug. 1, 2012, for Chilean Application No. 2008003779, 22 pages.
Chinese Office Action dated Mar. 28, 2012, for Chinese Application No. 200880120258.8, 10 pages.
Korean Office Action dated Feb. 24, 2012, for Korean Patent Application No. 20107013773, 6 pages.
Citations from Israeli Office Action, dated Feb. 29, 2012, in Israeli Patent Application No. 205285, 2 pages.
Japanese Office Action dated Aug. 14, 2012, for Japanese Patent Application No. 2010-538440, 12 pages.
Japanese Office Action dated Aug. 14, 2012, for Japanese Patent Application No. 2010-538441, 11 pages.
Korean Office Action dated Jan. 31, 2012, for Korean Patent Application No. 2010-7013760, 11 pages.
European Search Report dated Mar. 14, 2006, for European Patent Application No. 07024864.6, 8 pages.
European Search Report dated Aug. 31, 2009, for European Patent Application No. 09005108.7, 6 pages.
Taiwanese Search Report for Taiwanese Patent Application No. 099110151, filed on Apr. 1, 2010, Completion of Search Sep. 12, 2012, 1 page.
International Search Report mailed on Aug. 5, 2010, for PCT Application No. PCT/EP2010/003559, filed on Jun. 14, 2010, 10 pages.
U.S. Appl. No. 14/551,957, filed Nov. 24, 1014 for Castoldi et al.
Adams et al. "Highly specific in vivo tumor targeting by monovalent and divalent forms of 741F8 anti-c-erbB-2 single-chain Fv," *Cancer Res.* 53:4026-4034, (1993).
An et al., "Targeted drug delivery to mesothelioma cells using functionally selected internalizing human single-chain antibodies," *Mol. Cancer Ther.* 7:569-578, (2008).
Anthony, R.M., et al. (2008). "A recombinant IgG Fc that recapitulates the antiinflammatory activity of IVIG", *Science*, 320(5874):373-376.
Armour, K.L. et al. (1999). "Recombinant human IgG molecules lacking Fcγ receptor I binding and monocyte triggering activities", *Eur. J. Immunol.* 29:2613-2624.

Arndt et al. "Factors influencing the dimer to monomer transition of an antibody single-chain Fv fragment," *Biochemistry*, 37(37):12918-26, (1998).
Backer et al. "Molecular vehicles for targeted drug delivery," *Bioconjugate Chem.* 13:462-467, (2002).
Behrens. "Synthesis of achiral linker reagents for direct labelling of oligonucleotides on solid supports," *Nucleosides & Nucleotides* 18:291-305, (1999).
Bordusa. in *Highlights in Biooraanic Chemistry*, Schmuck, C. and Wennemers, H., (eds.), Wiley VCH, Weinheim, pp. 389-403, (2004).
Brennan et al. "Preparation of bispecific antibodies by chemical recombination of monoclonal immunoglobulin G1 fragments," *Science* 229:81-83, (1985).
Carmichael et al. "Evaluation of a tetrazolium-based semiautomated colorimetric assay: assessment of chemosensitivity testing," *Cancer Res.* 47:936-942, (1987).
Carter et al. "High level *Escherichia coli* expression and production of a bivalent humanized antibody fragment," Bio/Technology 10:163-167, (1992).
Carter. "Potent antibody therapeutics by design", *Nature Reviews Immunology* 6:343-357, (2006).
Chames P. et al. (2009). "Bispecific antibodies for cancer therapy", *Current Opinion in Drug Discovery & Development*, 12(2):276-283.
Chan et al. "Therapeutic antibodies for autoimmunity and inflammation", *Nat. Rev. Immunol.*, 10(5):301-316, (2010).
Chang et al. "A General Method for Facilitating Heterodimeric Pairing Between Two Proteins: Application to Expression of *a* and *p* T-cell Receptor Extracellular Segments," *Proc. Nat'l Acad. Sci.* 91:11408-12, (Nov. 1994).
Charlton. In: *Methods in Molecular Biology*, vol. 248, Lo, B.K.C. (ed.), Humana Press, Totowa, N.J., pp. 245-254, (2003).
Cheong et al. "Affinity enhancement of bispecific antibody against two different epitopes in the same antigen," Biochem. Biophys. Res. Commun. 173:795-800, (1990).
Chin et al. "Addition of *p*-azido-L-phenylalanine to the genetic code of *Escherichia coli*", *J. Am. Chem. Soc.*, 124(31):9026-9027, (2002).
Chin et al. "In vivo photocrosslinking with unnatural amino Acid mutagenesis", *ChemBioChem*, 3(11):1135-1137, (2002).
Chin et al. "Addition of a photocrosslinking amino acid to the genetic code of *Escherichia coli*", *Proc. Natl. Acad. Sci. U.S.A.*, 99(17):11020-11024, (2002).
Clackson et al. "Making antibody fragments using phage display libraries," *Nature* 352:624-628, (1991).
Clancy et al. "Sortase transpeptidases: insights into mechanism, substrate specificity, and inhibition", *Biopolymers*, 94(4):385-396, (2010).
Cocuzza, "A Phosphoramidite Reagent for automated solid phase synthesis of 5'-biotinylated oligonucleotides," *Tetrahedron Letters* 30:6287-6290, (1989).
De Graaf et al. "Nonnatural amino acids for site specific protein conjugation," *Bioconjug. Chem.* 20:1281-1295, (2009).
Dervan. "Molecular recognition of DNA by small molecules," *Bioorg. Med. Chem.* 9:2215-2235, (2001).
Ding et al., "Gold Nanorods Coated with Multilayer Polyelectrolyte as Contrast Agents for Multimodal Imaging," *J. Phys. Chem. C* 111 (2007) 12552-12557.
Dubowchik et al. "Doxorubicin immunoconjugates containing bivalent, lysosomally-cleavable dipeptide linkages," *Bioorg. & Med. Chem. Letters* 12:1529-1532, (2002).
Ellman et al. "Biosynthetic Method for Introducing Unnatural Amino Acids Site-Specifically into Proteins", *Meth. Enzym.* ,202:301-336, (1991).
Frese. "Formylglycine aldehyde Tag—protein engineering through a novel post-translational modification," *ChemBioChem* 10:425-427, (2009).
Friend et al. "Phase I study of an engineered aglycosylated humanized CD3 antibody in renal transplant rejection", *Transplantation*, 68(11):1632-1637, (1999).
Gautier et al. "An engineered protein tag for multiprotein labeling in living cells," *Chem. Biol.* 15:128-136, (2008).

(56) References Cited

OTHER PUBLICATIONS

Gerngross. "Advances in the production of human therapeutic proteins in yeasts and filamentous fungi," *Nat. Biotech.* 22:1409-1414, (2004).
Goldenberg et al. "Multifunctional antibodies by the Dock-and-Lock method for improved cancer imaging and therapy by pretargeting," *J. Nuc. Med.* 49:158-163, (2008).
Gruber et al. "Efficient tumor cell lysis mediated by a bispecific single chain antibody expressed in *Escherichia coli*," *J. Immunol.* 152:5368-5374, (1994).
Hackenberger. "Chemoselective ligation and modification strategies for peptides and proteins," *Angew. Chem. Int. Ed.* 47:10030-10074, (2008).
Hatfield et al. "Antiangiogenic therapy in acute myelogenous leukemia: targeting of vascular endothelial growth factor and interleukin 8 as possible antileukemic strategies", *Curr. Cancer Drug Targets*, 5(4):229-248, (2005).
Hayashi et al. "Application of L-DNA as a molecular tag," *Nucl. Acids Symp. Ser.* 49:261-262, (2005).
Herberman, "Immunodiagnosis of Cancer," in *The Clinical Biochemistry of Cancer*, Fleisher ed., American Association of Clinical Chemists, p. 347, (1979).
Hey et al. "Artificial, non-antibody binding proteins for pharmaceutical and industrial applications," *Trends Biotechnol.* 23:514-522, 2005).
Hoppe et al. "A parallel three stranded alpha-helical bundle at the nucleation site of collagen triple-helix formation," *FEBS Lett.* 344:191-195, (1994).
Huber et al. "Crystallographic structure studies of an IgG molecule and an Fc fragment", *Nature*, 264:415-420, (1976).
Hudson et al. "Engineered antibodies," *Nat. Med.* 9:129-134, (2003).
Huynh et al. "Synthesis of cholesteryl supports and phosphoramidites containing a novel peptidyl linker for automated synthesis of triple-helix forming oligonucleotides (TFOs)," Nucleic Acids Symposium Series 29, Second International Symposium on Nucleic Acids Chemistry, pp. 19-20, (1993).
Ilangovan et al. (2001). "Structure of sortase, the transpeptidase that anchors proteins to the cell wall of *Staphylococcus aureus*", *Proc. Natl. Acad. Sci. U.S.A.* 98(11):6056-6061, (2001).
Iyer. "Abasic oligodeoxyribonucleoside phosphorothioates: synthesis and evaluation as anti-HIV-1 agents," *Nucleic Acids Research* 18:2855-2859, (1990).
Jackman et al. "Development of a Two-part Strategy to Identify a Therapeutic Human Bispedfic Antibody That Inhibits IgE Receptor Signaling," *The Journal of Biological Chemistry* 285(27):20850-20859, (Jul. 2, 2010).
Jeffrey et al. "Dipeptide-based highly potent doxorubicin antibody conjugates," *Bioorg. Med. Chem. Lett.* 16:358-362, (2006).
Jiang et al. "Advances in the assessment and control of the effector functions of therapeutic antibodies", *Nat. Rev. Drug Discov.*, 10(2):101-111, (2011).
Kindt et al., Kuby Immunology, 6th ed., W.H. Freeman and Co., N.Y., p. 91, (2007).
King et al. "Monoclonal antibody conjugates of doxorubicin prepared with branched peptide linkers: inhibition of aggregation by methoxytriethyleneglycol chains," *J. Med. Chem.* 45:4336-4343, (2002).
Klein et al., "Progress in Overcoming the Chain Association Issue in Bispecific Heterodimeric IgG Antibodies" *mAbs* 4(6):653-663, (2012).
Kostelny et al. "Formation of a bispecific antibody by the use of leucine zippers," *J. Immunol.* 148:1547-1553, (1992).
Kratz et al. "Prodrugs of anthracyclines in cancer chemotherapy," *Current Med. Chem.* 13:477-523, (2006).
Landschulz et al. "The leucine zipper: a hypothetical structure common to a new class of DNA binding proteins," *Science* 240:1759-1764, (1988).
Levary et al. "Protein-Protein fusion catalyzed by sortase A," *PLOS One* 6:e18342.1-e18342.1-6, (2011).

Li et al. "Optimization of humanized IgGs in glycoengineered Pichia pastoris," *Nat. Biotech.* 24:210-215, (2006).
Liu et al. "Mapping tumor epitope space by direct selection of single-chain Fv antibody libraries on prostate cancer cells," *Cancer Res.* 64 704-710, (2004).
Madej et al. "Engineering of an anti-epidermal growth factor receptor antibody to single chain format and labeling by sortase A-mediated protein ligation", *Biotechnology and Bioengineering*, 109(6):1461-1470, (2012).
Mann. "Proteomic analysis of post-translational modifications," *Biochemistry* 21:255-261, (2003).
McCarron et al. "Antibody conjugates and therapeutic strategies," *Mol. Interventions* 5:368-380, (2005).
McKeen et al. "Synthesis of fluorophore and quencher monomers for use in scorpion primers and nucleic acid structural probes," *Organic & Biomol. Chem.* 1: 2267-2275, (2003).
Meyer et al. "Oligonucleotide sequential bis-conjugation via click-oxime and click-Huisgen procedures," *Journal of Organic Chemistry* 75:3927-3930, (2010).
Mizukami et al. "Induction of interleukin-8 preserves the angiogenic response in HIF-1alpha-deficient colon cancer cells", *Nat. Med.*, 11(9):992-997, (2005).
Möhlmann et al. "In vitro sortagging of an antibody fab fragment: overcoming unproductive reactions of sortase with water and lysine side chains," *Chembiochem: A European Journal of Chemical Biology*, 12(11):1774-1780, (2011).
Morimoto et al. "Single-step purification of F(ab')2 fragments of mouse monoclonal antibodies (immunoglobulins G1) by hydrophobic interaction high performance liquid chromatography using TSKgel Phenyl-5PW," *J. Biochem. Biophys. Meth.* 24:107-117, (1992).
Morocho et al., "Novel biotin phosphoramidites with super-long tethering arms," *Nucleosides, Nucleotides & Nucleic Acids* 22:1439-1441, (2003).
Muller et al. "A dimeric bispecific miniantibody combines two specificities with avidity," *FEBS Lett.* 432:45-49, (1998).
Nagy et al., "Stability of cytotoxic luteinizing hormone-releasing hormone conjugate (AN-152) containing doxorubicin 14-O-hemiglutarate in mouse and human serum in vitro: implications for the design of preclinical studies," *Proc. Natl. Acad. Sci. USA* 97:829-834, (2000).
Nelson et al., "Oligonucleotide labeling methods. 3. Direct labeling of oligonucleotides employing a novel, non-nucleosidic, 2-aminobutyl-1,3-propanediol backbone," *Nucleic Acids Research* 20:6253-6259, (1992).
Neri et al. "High-affinity antigen binding by chelating recombinant antibodies (CRAbs)," *J. Mol. Biol.* 246:367-373, (1995).
Nielsen et al. "Therapeutic efficacy of anti-ErbB2 immunoliposomes targeted by a phage antibody selected for cellular endocytosis," *Biochim. Biophys. Acta* 1591:109-118, (2002).
Noren et al. "A General Method for Site-Specific Incorporation of Unnatural Amino Acids into Proteins", *Science*, 244:182-188, (1989).
Novellino et al. "A listing of human tumor antigens recognized by T cells: Mar. 2004 update", *Cancer Immunol. Immunother*, 54(3):187-207, (2005).
Pack et al. "Miniantibodies: use of amphipathic helices to produce functional, flexibly linked dimeric FV fragments with high avidity in *Escherichia coli*," *Biochem.* 31:1579-1584, (1992).
Parmiani et al. "Unique human tumor antigens: immunobiology and use in clinical trials", *J. Immunol*, 178(4):1975-1979, (2007).
Pon "A long chain biotin phosphoramidite reagent for the automated synthesis of 5'-biotinylated oligonucleotides," *Tetrahedron Letters* 32:1715-1718, (1991).
Popp et al. "Making and breaking peptide bonds: protein engineering using sortase", *Angewandte Chemie*, 50(22):5024-5032, (2011).
Portolano et al. "Lack of promiscuity in autoantigen-specific H and L chain combinations as revealed by human H and L chain roulette," *J. Immunol.* 150:880-887, (1993).
Presta et al. "Humanization of an anti-vascular endothelial growth factor monoclonal antibody for the therapy of solid tumors and other disorders," *Cancer Res.* 57:4593-4599, (1997).

(56) References Cited

OTHER PUBLICATIONS

Presta. "Molecular engineering and design of therapeutic antibodies," *Current Opinion in Immunology* 20:460-470, (2008).
Prokhorenko et al. "Incorporation of a Pyrene Nucleoside Analogue Into Synthetic Oligodeoxynucleotides Using a Nucleoside-Like Synthon," *Bioorganic & Medicinal Chemistry Letters* 5:2081-2084, (1995).
Putnam et al. "Synthesis and evaluation of RNA transesterification efficiency using stereospecific serinol-terpyridine conjugates," *Nucleosides, Nucleotides & Nucleic Acids* 24:1309-1323, (2005).
Ramzaeva et al. Oligonucleotides functionalized by fluorescein and rhodamine dyes: Michael addition of methyl acrylate to 2'-deoxypseudouridine, *Helv. Chim. Acta* 83:1108-1126, (2006).
Ren et al. "Macrophage migration inhibitory factor stimulates angiogenic factor expression and correlates with differentiation and lymph node status in patients with esophageal squamous cell carcinoma," *Ann. Surg.* 242:55-63, (2005).
Ren et al. (2009). "A biocompatible condensation reaction for the labeling of terminal cysteine residues on proteins," *Angew. Chem. Int. Ed.* 48:9658-9662, (2009).
Roget et al. "Synthesis and use of labelled nucleoside phosphoramidite building blocks bearing a reporter group: biotinyl, dinitrophenyl, pyrenyl and dansyl," *Nucleic Acids Research* 17:7643-7651, (1989).
Roland et al. "Dual Targeting strategies with bispecific antibodies," *MABS Landes Bioscience* 4(2):182-197, (2012).
Roux et al. "Comparisons of the ability of human IgG3 hinge mutants, IgM, IgE, and IgA2, to form small immune complexes: a role for flexibility and geometry," *J. Immunol.*, 161(8):4083-4090, (1998).
Sakamoto et al. "Enzyme-Mediated Site-Specific Antibody-Protein Modification Using a ZZ Domain as a Linker,"*BioConjugate Chem.*. 21 :2227-2293 (2010, e-pub. Nov. 11, 2010).
Salfeld. "Isotype Selection in Antibody Engineering," *Nat. Biotechnol.* 25(12):1369-1372, (Dec. 2007).
Seela. "Oligodeoxyribonucleotides containing 1,3-propanediol as nucleoside substitute," *Nucleic Acids Research* 15:3113-3129, (1987).
Sensi et al. "Unique tumor antigens: evidence for immune control of genome integrity and immunogenic targets for T cell-mediated patient-specific immunotherapy," *Clin. Cancer Res.* 12:5023-5032, (2006).
Senter. "Potent antibody drug conjugates for cancer therapy," *Curr. Opin. Chem. Biol.* 13:235-244, (2009).
Seo. "Post-translational modifications and their biological functions: proteomic analysis and systematic approaches," *Biochemistry and Molecular Biology* 37(1):35-44, (2004).
Shi et al. "A stereospecific synthesis of L-deoxyribose, L-ribose and L-ribosides," *Tetrahed.* 58:3287-3296, (2002).
Silva et al. "Synthesis of a new phosphoramidite nucleoside Biotinylated for the Preparation Oligonucleotide Multibiotinilado," *Biotecnologia Aplicada* 15:154-158, (1998).(Translation of English Abstract Only).
Sondermann et al. "The 3.2-A crystal structure of the human IgG1 Fc fragment-FcyRIII complex", *Nature*, 406:267-273, (2000).
Strop. et al. "Generating Bispecific Human IgG1 and IgG2 Antibodies from Any Antibody Pair", *Journal of Molecular Biology*, 420(3):204-219, (2012).
Su et al. "Novel non-nucleosidic phosphoramidites for oligonucleotide modification and labeling," *Bioorganic & Medicinal Chemistry Letters* 7:1639-1644, (1997).
Sunbul. "Site specific protein labeling by enzymatic post-translational modification," *Org. Biomol. Chem.* 7:3361-3371, (2009).
Ta et al. "Enzymatic Single-Chain Antibody Tagging a Universal Approach to Targeted Molecular Imaging and Cell Homing in Cardiovascular Disease", *Circulation Research*, 109(4):365-373, (2011).
Taki et al., "Transglutaminase-mediated N- and C-terminal fluorescein labeling of a protein can support the native activity of the modified protein," *Prot. Eng. Des. Sel.* 17:119-126, (2004).
Taylor et al., "Native chemical ligation: semisynthesis of post-translationally modified proteins and biological probes," *Nucl. Acids Mol. Biol.* 22:65-96, (2009).
Thies et al. "Folding and association of the antibody domain CH3: prolyl isomerization precedes dimerization," *J. Mol. Biol.*, 293:67-79, (1999).
Theisen et al. "Fluorescent dye phosphoramidite labelling of oligonucleotides," *Nineteenth Symposium on Nucleic Acids Chemistry*, Fukuoka, Japan, Nov. 11-13, 1992, Nucleic Acids Symposium Series 27, 27:99-100, (1992).
Ton-That et al. "Purification and characterization of sortase, the transpeptidase that cleaves surface proteins of *Staphylococcus aureus* at the LPXTG motif", *Proc. Natl. Acad. Sci. U.S.A.*, 96(22):12424-12429, (1999).
Torgov et al., "Generation of an intensely potent anthracycline by a monoclonal antibody-beta-galactosidase conjugate," *Bioconjug. Chem.* 16 (2005) 717-721.
Tso et al., "Preparation of a Bispecific F(ab')$_2$ Targeted to the Human II-2 Receptor," *J. Hematotherapy* 4:389-94, (1995).
Tsukiji S. et al. "Sortase-Mediated Ligation: A Gift from Gram-Positive Bacteria to Protein Engineering", *Chembiochem*, 10(5):787-798, (2009).
Urata et al., "Synthesis and properties of mirror-image DNA," *Nucl. Acids Res.* 20:3325-3332, (1992).
Vallböhmer et al "Molecular determinants of cetuximab efficacy", *J Clin. Oncol.*, 23(15):3536-3544, (2005).
Wagner et al. "Bispecific antibody generated with sortase and click chemistry has broad antiinfluenza virus activity," *Proc. Natl. Acad. Sci. USA* 111:16820-16825, (Nov. 25, 2014).
Wang et al. "Expanding the genetic code", *Chem. Commun (Camb.)*, 7:1-11, (2002).
Wang et al. "Site-specific fluorescent labeling of DNA using Staudinger ligation," *Bioconjugate Chemistry* 14:697-701, (2003).
Ward et al. "The effector functions of immunoglobulins: implications for theraty", *Ther. Immunol.*, 2:77-94, (1995).
Witte et al. "Preparation of unnatural N-to-N and C-to-C protein fusions", *Proceedings of the National Academy of Sciences of the United States of America*, 109(30):11993-11998, (2012).
Wojczewski et al. "Fluorescent oligonucleotides—versatile tools as probes and primers for DNA and RNA analysis," *Synlett* 10:1667-1678, (1999).
Wright et al. "Phage display of chelating recombinant antibody libraries," *Molecular Immunology* 44:2860-2869, (2007).
Yazaki et al. Methods in Molecular Biology, vol. 248, Lo, B.K.C. (ed.), Humana Press, Totowa, NJ (2004), pp. 255-268, (2004).
Zahn et al. "Alternative heterocycles for DNA recognition: a 3-pyrazole/pyrrole pair specifies for G.C base pairs," *Bioorg. Med. Chem.* 8:2467-2474, (2000).

* cited by examiner

Conjugated Common LC multi chain Ab (mcAb)

SEQUENCE LISTING

```
<160> NUMBER OF SEQ ID NOS: 21

<210> SEQ ID NO 1
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Thr His Thr
1

<210> SEQ ID NO 2
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Gly Gly Gly Ser Thr His Thr
1               5

<210> SEQ ID NO 3
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Gly Gly Gly Ser Gly Gly Gly Ser Thr His Thr
1               5                   10

<210> SEQ ID NO 4
<211> LENGTH: 7
<212> TYPE: PRT
<213> ORGANISM: Unknown
<220> FEATURE:
<221> NAME/KEY: source
<223> OTHER INFORMATION: /note="Description of Unknown: Cleavage site
      peptide cleaved by TEV"

<400> SEQUENCE: 4

Glu Asn Leu Tyr Phe Gln Gly
1               5

<210> SEQ ID NO 5
<211> LENGTH: 9
<212> TYPE: PRT
<213> ORGANISM: Unknown
<220> FEATURE:
<221> NAME/KEY: source
<223> OTHER INFORMATION: /note="Description of Unknown: Cleavage site
      peptide for Hedgehog protein"

<400> SEQUENCE: 5

Gly Asp Trp Asn Ala Arg Trp Cys Phe
1               5

<210> SEQ ID NO 6
```

```
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Any basic amino acid
<220> FEATURE:
<221> NAME/KEY: MOD_RES
<222> LOCATION: (2)..(3)
<223> OTHER INFORMATION: Any amino acid
<220> FEATURE:
<221> NAME/KEY: source
<223> OTHER INFORMATION: /note="see specification as filed for detailed
      description of substitutions and preferred embodiments"

<400> SEQUENCE: 6

Xaa Xaa Xaa Arg
1

<210> SEQ ID NO 7
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: VARIANT
<222> LOCATION: (5)..(5)
<223> OTHER INFORMATION: /replace="Arg"
<220> FEATURE:
<221> NAME/KEY: misc_feature
<222> LOCATION: (5)..(5)
<223> OTHER INFORMATION: /note="Residue given in the sequence has no
      preference with respect to the annotation for said position"

<400> SEQUENCE: 7

Arg Xaa Arg Xaa Lys Arg
1               5

<210> SEQ ID NO 8
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid

<400> SEQUENCE: 8

Arg Xaa Arg Xaa Arg Arg
1               5
```

```
<210> SEQ ID NO 9
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Arg Lys Arg Lys Arg Arg
1               5

<210> SEQ ID NO 10
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Arg His Arg Gln Pro Arg
1               5

<210> SEQ ID NO 11
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Arg Ser Arg Lys Arg Arg
1               5

<210> SEQ ID NO 12
<211> LENGTH: 6
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (2)..(2)
<223> OTHER INFORMATION: a, c, t, g, unknown or other

<400> SEQUENCE: 12 cncaat                                                              6

<210> SEQ ID NO 13
<211> LENGTH: 6
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13 aataaa                                                              6
```

-continued

<210> SEQ ID NO 14
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Arg Lys Arg Lys Arg Arg Gly Gly Gly Ser Gly Gly Ser Gly Gly Ser
1               5                   10                  15

Gly Gly Ser Gly Gly Ser Gly Gly Ser Gly Arg Ser Arg Lys Arg Arg
            20                  25                  30

<210> SEQ ID NO 15
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Gly Gly Ser Gly Gly Ser Gly Gly Ser Gly Gly Ser Gly Gly Ser Gly
1               5                   10                  15

Gly Ser Gly Gly Ser Gly Gly Ser Arg Ser Arg Lys Arg Arg
            20                  25                  30

<210> SEQ ID NO 16
<211> LENGTH: 33
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Arg Ser Arg Lys Arg
            20                  25                  30

Arg

<210> SEQ ID NO 17
<211> LENGTH: 36
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser Arg Ser
            20                  25                  30

Arg Lys Arg Arg
        35

<210> SEQ ID NO 18
<211> LENGTH: 5

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Arg Lys Arg Lys Arg
1               5

<210> SEQ ID NO 19
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (25)..(27)
<223> OTHER INFORMATION: /replace=" "
<220> FEATURE:
<221> NAME/KEY: misc_feature
<222> LOCATION: (25)..(27)
<223> OTHER INFORMATION: /note="Residues given in the sequence have no
      preference with respect to those in the annotation for said
      positions"
<220> FEATURE:
<221> NAME/KEY: misc_feature
<222> LOCATION: (1)..(27)
<223> OTHER INFORMATION: /note="This sequence may encompass 8 to 9 "Gly
      Gly Ser" repeating units

<400> SEQUENCE: 19

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser
            20                  25

<210> SEQ ID NO 20
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Gly Gly Ser Gly Gly Ser Gly Gly Ser Gly Gly Ser Gly Gly Ser Gly
1               5                   10                  15

Gly Ser

<210> SEQ ID NO 21
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 10xHis tag"

<400> SEQUENCE: 21

His His His His His His His His His His
1               5                   10
```

US 9,688,758 B2

SINGLE-CHAIN ANTIBODIES AND OTHER HETEROMULTIMERS

This application is a continuation of International Application No. PCT/US2013/025365 having an international filing date of Feb. 8, 2013, the entire contents of which are incorporated herein by reference, and which claims the benefit of priority under 35 U.S.C. §119 to U.S. Provisional Application Ser. No. 61/597,486, filed Feb. 10, 2012, the disclosure of which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Jul. 31, 2014, is named P4733C1_SequenceListing.txt and is 7,543 bytes in size.

FIELD OF THE INVENTION

This invention relates to novel engineered proteins and protein complexes, including heteromultimers (e.g., single-chain antibodies, multi-chain antibodies, and immunoadhesin-antibody complexes) with mono- or multi-specificity, methods of constructing them and producing them. This invention also relates to the new application of technologies useful in obtaining the mono- or multi-specific heteromultimers. The heteromultimers generated by the methods provided herein are useful as a therapeutic for any disease or pathological condition as well as any other use in which use of an antibody is advantageous.

BACKGROUND OF THE INVENTION

Developing technologies for producing antibodies or other heteromultimers with different binding characteristics (e.g., monospecific or multispecific) that are useful and scalable for commercial and therapeutic purposes has been elusive. Many methods have been tried, but nearly all suffer significant drawbacks such as being poorly soluble or inexpressible in mammalian cells, demonstrating low yield of heterodimer formation, being technically challenging to manufacture or immunogenic, exhibiting short half-life in vivo, or being unstable, among other problems (e.g., Hollinger et al., (1993) PNAS 90:6444-6448; U.S. Pat. No. 5,932,448; U.S. Pat. No. 6,833,441; U.S. Pat. No. 5,591,828; U.S. Pat. No. 7,129,330; U.S. Pat. No. 7,507,796; Fischer et al., (2007) Pathobiology 74:3-14; Booy (2006) Arch. Immunol. Ther. Exp. 54:85-101; Cao et al., (2003) 55: 171-197; and Marvin et al., (2006) Current Opinion in Drug Discovery & Development 9(2): 184-193). Thus, there is a need for improved technologies and processes to make antibodies or other heteromultimers with different binding characteristics.

SUMMARY OF THE INVENTION

The present invention provides heteromultimers (e.g., novel single-chain antibodies (scAbs), multi-chain antibodies (mcAbs), and immunoadhesin-antibody complexes) and methods of creating, manufacturing, and using the heteromultimers. In one aspect, the invention features a heteromultimeric single-chain antibody including a HeteroDimerization (HD) tether, which links a first heavy chain variable (VH) domain to a second VH domain, wherein the heteromultimer includes one or more heavy chain constant (CH) domains selected from a first CH2 domain, a first CH3 domain, a second CH2 domain, and a second CH3 domain. In one embodiment, the heteromultimer includes at least one pair of heavy chain constant domains. In another embodiment, the heteromultimer may include a hinge domain positioned between a VH and CH2 domain on one or both heavy chains. In another embodiment, the heteromultimer includes a first and/or second CH1 domain. The one or two CH1 domains are positioned C-terminal to one or both VH domains and N-terminal to one or both hinge domains, or one or both CH2 domains in the absence of the hinge domains. In particular embodiments, the heteromultimer may also include one or two light chain variable (VL) domains, which are linked N-terminal to the first and/or second VH domains by one or two CLH tethers (Cognate LC-HC tether). In some embodiments, the heteromultimer further includes one or two light chain constant (CL) domains, which are each positioned C-terminal to one or both VL domains and immediately N-terminal to one or both CLH tethers.

In another aspect, the invention features a heteromultimeric single-chain antibody including a single polypeptide with the following domains positioned relative to each other in an N-terminal to C-terminal direction as follows: $VL_1$-$CL_1$-CLH tether$_1$-$VH_1$-$CH1_1$-hinge$_1$-$CH2_1$-$CH3_1$-HD tether-$VL_2$-$CL_2$-CLH tether$_2$-$VH_2$-$CH1_2$-hinge$_2$-$CH2_2$-$CH3_2$.

In another aspect, the invention features a multi-chain antibody heteromultimer including three polypeptide chains, where the first and second polypeptide chains are identical and each forms a light chain (LC) and the third polypeptide chain forms a first heavy chain (HC) and second HC. The first and second polypeptide chains each include a VL and CL domain. The third polypeptide chain includes two VH domains, an HD tether, one or two hinge domains, and one or more heavy chain constant domains selected from a first CH1 domain, a first CH2 domain, a first CH3 domain, a second CH1 domain, a second CH2 domain, and a second CH3 domain, wherein the components of the second polypeptide chain are positioned relative to each other in an N-terminal to C-terminal direction as follows: $VH_1$-optional $CH1_1$-optional hinge$_1$-optional $CH2_1$-optional $CH3_1$-HD tether-$VH_2$-optional $CH1_2$-optional hinge$_2$-optional $CH2_2$-optional $CH3_2$.

In another aspect, the invention features a multi-chain antibody heteromultimer including two polypeptide chains, where the first polypeptide chain forms a first light chain (LC) and the second polypeptide chain forms a first heavy chain (HC), second LC, and second HC. The first polypeptide chain includes a first VL and CL domain. The second polypeptide chain includes two VH domains, an HD tether, a second VL domain, a second CL domain, a CLH tether, one or two hinge domains, and one or more heavy chain constant domains selected from a first CH1 domain, a first CH2 domain, a first CH3 domain, a second CH1 domain, a second CH2 domain, and a second CH3 domain, wherein the components of the second polypeptide chain are positioned relative to each other in an N-terminal to C-terminal direction as follows: $VH_1$-optional $CH1_1$-optional hinge$_1$-optional $CH2_1$-optional $CH3_1$-HD tether-$VL_2$-$CL_2$-CLH tether-$VH_2$-optional $CH1_2$-optional hinge$_2$-optional $CH2_2$-optional $CH3_2$.

In another aspect, the invention features a multi-chain antibody heteromultimer including two polypeptide chains, where the first polypeptide chain forms a first LC, first HC, and second HC and the second polypeptide chain forms a second LC. The first polypeptide chain includes two VH domains, an HD tether, a first VL domain, a first CL domain, a CLH tether, one or two hinge domains, and one or more heavy chain constant domains selected from a first CH1 domain, a first CH2 domain, a first CH3 domain, a second CH1 domain, a second CH2 domain, and a second CH3 domain, wherein the components of the second polypeptide chain are positioned relative to each other in an N-terminal to C-terminal direction as follows: $VL_1$-$CL_1$-CLH tether-$VH_1$-optional $CH1_1$-optional hinge$_1$-optional $CH2_1$-optional $CH3_1$-HD tether-$VH_2$-optional $CH1_2$-optional hinge$_2$-optional $CH2_2$-optional $CH3_2$. The second polypeptide chain includes a second VL and CL domain.

In another aspect, the invention features a heteromultimer including two polypeptide chains, where the first polypeptide includes an immunoadhesin that includes an adhesin and one or more heavy chain constant domains (e.g., $CH2_1$ and/or $CH3_1$), the second polypeptide forms a half-antibody that includes a VH domain and one or more heavy chain constant domains (e.g., CH1, $CH2_2$, and/or $CH3_2$), and the first and second polypeptide chains are linked to one another by an HD tether to form a single polypeptide chain. The components of the heteromultimer are positioned relative to each other in an N-terminal to C-terminal direction as follows: adhesin-optional $CH2_1$-optional $CH3_1$-HD tether-VH-optional CH1-optional $CH2_2$-optional $CH3_2$. The HD tether facilitates interaction between the one or more constant domains of the immunoadhesin and the half-antibody. In one embodiment, a CLH tether facilitates the interaction between light chain and heavy chain components of the half-antibody to yield a heteromultimer with components positioned relative to each other in an N-terminal to C-terminal direction as follows: adhesin-optional $CH2_1$-optional $CH3_1$-HD tether-VL-CL-CLH tether-VH-optional CH1-optional $CH2_2$-optional $CH3_2$. In another embodiment, the VL and CL domains of the light chain of the half-antibody are provided by a second polypeptide, which associates with the heavy chain of the half-antibody of the first polypeptide chain to form a light chain-heavy chain cognate pair. In another embodiment, the immunoadhesin portion of the heteromultimer may include an amino acid spacer between its adhesin and heavy chain constant domain components. The spacer, in one embodiment, includes glycine (G) and serine (S) residues, for example, as GGS repeats. In another embodiment, the spacer is between 10-80 amino acids in length, for example, between 20-40 residues in length.

The heteromultimer of the invention may include an HD tether of between 15-100 amino acids in length. In a particular embodiment, the HD tether is between 30-39 amino acids in length, for example, 30, 31, 32, 33, 34, 35, 36, 37, 38, or 39 amino acids in length. The tether, in one embodiment, includes glycine (G) and serine (S) residues. In another embodiment, the tether includes GGS repeats. In a preferred embodiment, the tether includes 8 to 9 GGS repeats (SEQ ID NO: 19).

The heteromultimer of the invention may also include one or more CLH tethers. In one embodiment, the one or more CLH tethers are each between 10-80 amino acids in length. In a particular embodiment, the one or more CLH tethers are each between 20-40 amino acids in length. The tether, in one embodiment, includes glycine (G) and serine (S) residues. In another embodiment, the tether includes GGS repeats.

In another embodiment, one or more of the HD and CLH tethers of the invention are cleavable by one or more of the following endopeptidases: furin, urokinase, thrombin, tissue plasminogen activator (tPa), genenase, Lys-C, Arg-C, Asp-N, Glu-C, Factor Xa, tobacco etch virus protease (TEV), enterokinase, human rhinovirus C3 protease (HRV C3), or kininogenase. In a preferred embodiment, at least one of the tethers is cleavable by furin. In another embodiment, at least one of the one or more of the tethers of the invention is cleavable in two sites at or near the N- and C-terminus of the tether. Preferably for the HD tether, one of the two cleavage sites is a furin cleavage site and the other cleavage site is a Lys-C cleavage site. Preferably for CLH tethers, both N- and C-terminal cleavage sites of the one or more CLH tethers are cleavable by furin. In certain embodiments, the furin cleavage site comprises the amino acid sequence RKRKRR (SEQ ID NO:9). In certain other embodiments, the furin cleavage site comprises the amino acid sequence RHRQPR (SEQ ID NO:10). In one embodiment, endopeptidase cleavage occurs in situ. In certain embodiment, the endopeptidase is recombinantly expressed in a host cell. In another embodiment, endopeptidase cleavage occurs upon addition of the endopeptidase following purification.

The heteromultimer of the invention may have one or more (e.g., two) CLH tethers which each include one or more cleavage sites for one or more of the following specific exopeptidases: Carboxypeptidase A, Carboxypeptidase B, plasma Carboxypeptidase B (also known as Carboxypeptidase U or thrombin-activatable fibrinolysis inhibitor (TAFI)), Carboxypeptidase D, Carboxypeptidase E (also known as enkephalin convertase or Carboxypeptidase H), Carboxypeptidase M, Carboxypeptidase N, or Carboxypeptidase Z. In a preferred embodiment, the heteromultimer of the invention is cleavable by a Carboxypeptidase B exopeptidase. In one embodiment, exopeptidase cleavage occurs in situ. In certain embodiment, the exopeptidase is recombinantly expressed in a host cell. In another embodiment, exopeptidase cleavage occurs upon addition of the exopeptidase following purification. As used herein, Carboxypeptidase B may refer to the class of carboxypeptidases or the specific carboxypeptidase. As a class, Carboxypeptidase B includes all specific carboxypeptidases except Carboxypeptidase A. As a specific carboxypeptidase, Carboxypeptidase B is also known as Carboxypeptidase U or TAFI. One of skill in the art can readily discern the distinction between Carboxypeptidase B as a class and Carboxypeptidase B as a specific exopeptidase, depending on the context in which the term is used.

In yet another embodiment, the heteromultimer of the invention may include one or more hinge domains, including but not limited to hinge domains that include Glu216 to Pro230 of human IgG1. In some embodiments, one or both hinge domains include a mutation that removes a Lys-C endopeptidase cleavage site. In one example, the mutation that removes a Lys-C endopeptidase cleavage site is a K222A substitution (EU numbering system).

The heteromultimer of the invention may be monospecific. In one embodiment, the monospecific heteromultimer of the invention comprises two half-antibodies that bind the same epitope target but may bind with different affinities. In another embodiment, the monospecific heteromultimer of the invention includes a half-antibody associated with an immunoadhesin that each are specific for the same binding partner or epitope.

The heteromultimer of the invention may be bispecific or multispecific. In one embodiment, the heteromultimer is capable of binding at least two antigens. In another embodiment, the heteromultimer is capable of binding at least two epitopes on the same antigen. In yet another embodiment, the bispecific or multispecific heteromultimer of the invention includes a half-antibody associated with an immunoadhesin, each of which is specific for a different binding partner or epitope.

In another embodiment, the heteromultimer of the invention includes a constant region conjugated to a cytotoxic agent.

In another embodiment, the heteromultimer may include two heavy chain constant domains (e.g., two CH3 domains) having a protuberance or cavity, wherein the protuberance or cavity of one heavy chain constant domain (e.g., $CH3_1$ domain) is positionable into the cavity or protuberance, respectively, of the second heavy chain constant domain (e.g., $CH3_2$ domain). Preferably, the two constant domains meet at an interface comprising the protuberance and cavity. In yet another embodiment, the heteromultimer may include at least one light chain constant domain and one heavy chain constant domain interface (e.g., a CL/CH1 interface), wherein the light chain constant domain (e.g., CL domain) and heavy chain constant domain (e.g., CH1 domain) interact, at least in part, by a protuberance-cavity interaction.

In another embodiment, the heteromultimer of the invention includes a CH2 domain mutation in either its $CH2_1$ or $CH2_2$ that results in an antibody with altered effector functions. In a preferred embodiment, the CH2 domain mutation is a N297 mutation. In certain embodiments, the N297 mutation is an N297A mutation. In certain other embodiments, the CH2 domain further comprises a D256A mutation.

In a further aspect, the invention features methods for producing a heteromultimer. In another aspect, the invention features polynucleotides encoding heteromultimers of the invention. In additional aspects, the invention features vectors including the polynucleotides of the invention and a host cell including the vectors. In one embodiment, the host cell is a mammalian cell. In a preferred embodiment, the mammalian cell is a CHO cell. In another embodiment, the host cell is a prokaryotic cell. In a further embodiment, the prokaryotic cell is an *E. coli* cell. In an additional aspect, the invention features a method of producing a heteromultimer that includes culturing the host cell that comprises the vector with heteromultimer-encoding polynucleotides in a culture medium. Preferably, the heteromultimer is recovered from the host cell or the host cell's culture medium.

In a further aspect, the invention provides single-chain antibodies comprising a single polypeptide comprising the following domains positioned relative to each other in an N-terminal to C-terminal direction: $VL_1$-$CL_1$-CLH $tether_1$-$VH_1$-$CH1_1$-$hinge_1$-$CH2_1$-$CH3_1$-HD tether-$VL_2$-$CL_2$-CLH $tether_2$-$VH_2$-$CH1_2$-$hinge_2$-$CH2_2$-$CH3_2$, wherein the CLH $tether_1$, CLH $tether_2$ and HD tether each comprises an amino acid sequence cleavable by furin endopeptidase. In certain embodiments of the aspect, the furin cleavable sequence comprises the amino acid sequence RKRKRR (SEQ ID NO: 9), while in other embodiments, the furin cleavable sequence comprises the amino acid sequence RHRQPR (SEQ ID NO: 10). In related aspects, the invention provides polynucleotide molecules encoding the single-chain antibody of the invention, vectors comprising the polynucleotides, and host cells comprising the vectors. In certain embodiments, the host cell is a mammalian cell, including without limitation, a CHO cell. In certain other embodiments, the host cell is a prokaryotic cell, including without limitation, an *E. coli* cell. In a further related aspect, the invention provides methods of producing the single-chain antibody comprising culturing the host cell that comprises the vector in a culture medium. In certain embodiments, the method further comprises the step of recovering said single-chain antibody from said host cell or said culture medium.

Other features and advantages of the invention will be apparent from the following Detailed Description, the Drawings, and the Claims.

DETAILED DESCRIPTION OF THE INVENTION

Figure 1:
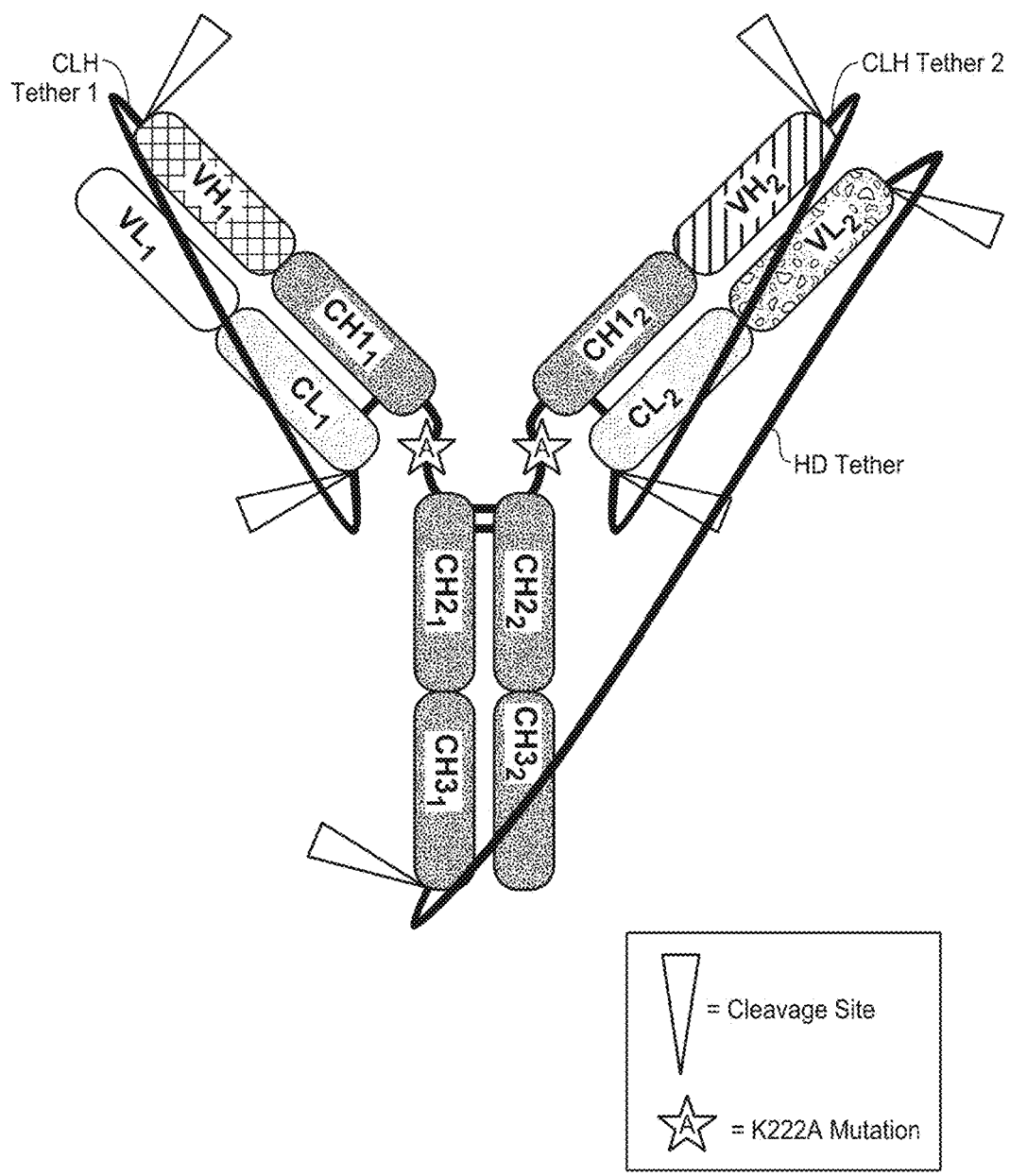
FIG. 1 is a schematic diagram showing the structure of an exemplary heteromultimeric single-chain antibody comprising three cleavable tethers. Endopeptidase cleavage sites are indicated by the triangles. Also depicted is an optional K222A mutation.

Unwanted heavy-chain homodimerization typically occurs when generating monospecific or multispecific (e.g., bispecific) antibodies or other heteromultimers having different binding properties with multiple polypeptide chains. We have discovered this common problem can be circumvented by the generation of single-chain monospecific or multispecific heteromultimers, whose assembly is directed by one or more tethers. Without being bound by theory, we believe that the HD tether enables the binding of distinct Fc heavy-chain components with a high degree of accuracy and efficiency, yielding a functional heteromultimer comprising two-half molecules (e.g., two half-antibodies) which bind the same target or different targets with the same or different binding affinity. The heteromultimer with linked heavy-chain components may additionally include distinct light-chain components, yielding a functional single-chain monospecific or multispecific heteromultimer (e.g., antibody) with a complete complement of heavy and light chains. Additional tethers according to the present invention can be used to link the light and heavy chains of a heteromultimer and thereby aid in the proper association of each light chain to its cognate heavy chain.

Use of the methods for making heteromultimers described herein allows for the production of a substantially homogeneous population of monospecific or multispecific heteromultimers generated from a single or multiple polypeptide sequences. The heteromultimers generated by the methods described herein can be useful for recognition of more than one target in a pathogenic pathway or for co-localization of a specific target (e.g., a tumor cell) and an agent directed against the target (e.g., a T cell). In addition, the heteromultimers described herein are advantageous because they eliminate the need for combination therapy to target two antigens and the risk associated with providing two or more therapeutics to a subject.

I. Definitions

The term "antibody" herein is used in the broadest sense and refers to any immunoglobulin (Ig) molecule comprising two heavy chains and two light chains, and any fragment, mutant, variant or derivation thereof so long as they exhibit the desired biological activity (e.g., epitope binding activity). Examples of antibodies include monoclonal antibodies, polyclonal antibodies, bispecific antibodies, multispecific antibodies, and antibody fragments.

The Kabat numbering system is generally used when referring to a residue in the variable domain (approximately residues 1-107 of the light chain and residues 1-113 of the heavy chain) (e.g., Kabat et al., Sequences of Immunological Interest. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies means residue numbering by the Kabat numbering system. Unless stated otherwise herein, references to residue numbers in the heavy chain constant domain of antibodies means residue numbering by the EU numbering system.

A naturally occurring basic 4-chain antibody unit is a heterotetrameric glycoprotein composed of two identical light chains (LCs) and two identical heavy chains (HCs) (an IgM antibody consists of 5 of the basic heterotetramer units along with an additional polypeptide called J chain, and therefore contains 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each LC is linked to an HC by one covalent disulfide bond, while the two HCs are linked to each other by one or more disulfide bonds depending on the HC isotype. Each HC and LC also has regularly spaced intrachain disulfide bridges. Each HC has, at the N-terminus, a variable domain (VH) followed by three constant domains (CH1, CH2, CH3) for each of the α and γ chains and four Cj domains for μ and ε isotypes. Each LC has, at the N-terminus, a variable domain (VL) followed by a constant domain (CL) at its other end. The VL is aligned with the VH and the CL is aligned with the first constant domain of the heavy chain (CH1). CH1 can be connected to the second constant domain of the heavy chain (CH2) by a hinge region. Particular amino acid residues are believed to form an interface between the light chain and heavy chain variable domains. The pairing of a VH and VL together forms a single antigen-binding site. For the structure and properties of the different classes of antibodies, see, e.g., Basic and Clinical Immunology, 8th edition, Daniel P. Stites, Abba I. Ten and Tristram G. Parslow (eds.), Appleton & Lange, Norwalk, Conn., 1994, page 71 and Chapter 6.

"Hinge region" is generally defined as stretching from Glu216 to Pro230 of human IgG1 (Burton, Molec. Immunol. 22: 161-206 (1985)). Hinge regions of other IgG isotypes may be aligned with the IgG1 sequence by placing the first and last cysteine residues forming inter-heavy chain S—S bonds in the same positions.

The "lower hinge region" of an Fc region is normally defined as the stretch of residues immediately C-terminal to the hinge region, i.e., residues 233 to 239 of the Fc region. Prior to the present invention, FcgammaR binding was generally attributed to amino acid residues in the lower hinge region of an IgG Fc region.

The "CH2 domain" of a human IgG Fc region usually extends from about residues 231 to about 340 of the IgG. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, Molec. Immunol. 22: 161-206 (1985).

The "CH3 domain" comprises the stretch of residues C-terminal to a CH2 domain in an Fc region (i.e., from about amino acid residue 341 to about amino acid residue 447 of an IgG).

The light chain (LC) from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated α, δ, γ, ε, and μ, respectively. The γ and α classes are further divided into subclasses on the basis of relatively minor differences in CH sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The V domain mediates antigen binding and defines specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md., 1991). The constant domains are not involved directly in binding an antibody to an antigen, but exhibit various effector functions, such as participation of the antibody in antibody dependent cellular cytotoxicity (ADCC).

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. An HVR as used herein comprise any number of residues located within positions 24-36 (for L1), 46-56 (for L2), 89-97 (for L3), 26-35B (for H1), 47-65 (for H2), and 93-102 (for H3). Therefore, an HVR includes residues in positions described previously in (A), (B), and (C): (A) 24-34 (L1), 50-52 (L2), 91-96 (L3), 26-32 (H1), 53-55 (H2), and 96-101 (H3) (Chothia and Lesk, *J. Mol. Biol.* 196:901-917 (1987); (B) 24-34 of L1, 50-56 of L2, 89-97 of L3, 31-35B of H1, 50-65 of H2, and 95-102 of H3 (Kabat et al., *Sequences of Proteins of Immunological Interest*, 5th Ed. Public Health Service, National Institutes of Health, Bethesda, Md. (1991); (C) 30-36 (L1), 46-55 (L2), 89-96 (L3), 30-35 (H1), 47-58 (H2), 93-100a-j (H3) (MacCallum et al. J. Mol. Biol. 262: 732-745 (1996). Unless otherwise indicated, HVR residues and other residues in the variable domain (e.g., FR residues) are numbered herein according to Kabat et al., supra.

A number of HVR delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md., 1991). Chothia refers instead to the location of the structural loops (Chothia and Lesk J. Mol. Biol. 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat | AbM | Chothia | Contact |
| --- | --- | --- | --- | --- |
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B (Kabat Numbering) | H26-H32 | H30-H35B |
| H1 | H31-H35 | H26-H35 (Chothia Numbering) | H26-H32 | H30-H35 |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

"Framework regions" (FR) are those variable domain residues other than the CDR residues. Each variable domain typically has four FRs identified as FR1, FR2, FR3, and FR4. If the CDRs are defined according to Kabat, the light chain FR residues are positioned at about residues 1-23 (LCFR1), 35-49 (LCFR2), 57-88 (LCFR3), and 98-107 (LCFR4) and the heavy chain FR residues are positioned about at residues 1-30 (HCFR1), 36-49 (HCFR2), 66-94 (HCFR3), and 103-113 (HCFR4) in the heavy chain residues. If the CDRs comprise amino acid residues from hypervariable loops, the light chain FR residues are positioned about at residues 1-25 (LCFR1), 33-49 (LCFR2), 53-90 (LCFR3), and 97-107 (LCFR4) in the light chain and the heavy chain FR residues are positioned about at residues 1-25 (HCFR1), 33-52 (HCFR2), 56-95 (HCFR3), and 102-113 (HCFR4) in the heavy chain residues. In some instances, when the CDR comprises amino acids from both a CDR as defined by Kabat and those of a hypervariable loop, the FR residues will be adjusted accordingly. For example, when CDRH1 includes amino acids H26-H35, the heavy chain FR1 residues are at positions 1-25 and the FR2 residues are at positions 36-49.

A "human consensus framework" is a framework that represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat. In one embodiment, for the VL, the subgroup is subgroup kappa I as in Kabat. In one embodiment, for the VH, the subgroup is subgroup III as in Kabat.

One example of an "intact" antibody is one that comprises an antigen-binding site as well as a CL and heavy chain constant domains, CH1, CH2, and CH3. The constant domains can be native sequence constant domains (e.g., human native sequence constant domains) or amino acid sequence variant thereof.

"Antibody fragments" comprise a portion of an intact antibody, preferably the antigen binding or a variable region of the intact antibody. Examples of antibody fragments include Fab, Fab', F(ab')2, and Fv fragments; diabodies (Db); tandem diabodies (taDb), linear antibodies (e.g., U.S. Pat. No. 5,641,870, Example 2; Zapata et al., Protein Eng.

8(10): 1057-1062 (1995)); one-armed antibodies, single variable domain antibodies, minibodies, single-chain antibody molecules; and multispecific antibodies formed from antibody fragments (e.g., including but not limited to, Db-Fc, taDb-Fc, taDb-CH3 and (scFV)4-Fc).

A "Fab" fragment is an antigen-binding fragment generated by papain digestion of antibodies and consists of an entire L chain along with the variable region domain of the H chain (VH), and the first constant domain of one heavy chain (CH1). Papain digestion of antibodies produces two identical Fab fragments. Pepsin treatment of an antibody yields a single large F(ab')2 fragment which roughly corresponds to two disulfide linked Fab fragments having divalent antigen-binding activity and is still capable of cross-linking antigen. Fab' fragments differ from Fab fragments by having an additional few residues at the carboxy terminus of the CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

A "Fc" fragment is a residual antibody fragment generated by papain digestion, the designation reflecting the ability of the fragment to crystallize readily. The Fc fragment comprises the carboxy-terminal portions of both H chains held together by disulfides. The effector functions of antibodies are determined by sequences in the Fc region; this region is also the part recognized by Fc receptors (FcR) found on certain types of cells.

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue.

A "functional Fc region" possesses an "effector function" of a native sequence Fc region. Exemplary "effector functions" include C1q binding; CDC; Fc receptor binding; ADCC; phagocytosis; down regulation of cell surface receptors (e.g., B cell receptor; BCR), etc. Such effector functions generally require the Fc region to be combined with a binding domain (e.g., an antibody variable domain) and can be assessed using various assays as disclosed, for example, in definitions herein.

A "native sequence Fc region" comprises an amino acid sequence identical to the amino acid sequence of an Fc region found in nature. Native sequence human Fc regions include a native sequence human IgG 1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g., from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

"Fc complex" as used herein refers to two CH2 domains of an Fc region interacting together and/or two CH3 domains of an Fc region interacting together, wherein the CH2 domains and/or the CH3 domains interact through bonds and/or forces (e.g., Van der Waals, hydrophobic, hydrophilic forces) that are not peptide bonds.

"Fc component" as used herein refers to a hinge region, a CH2 domain or a CH3 domain of an Fc region.

"Fc CH component" or "FcCH" as used herein refers to a polypeptide comprising a CH2 domain, a CH3 domain, or CH2 and CH3 domains of an Fc region.

"Fv" consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although often at a lower affinity than the entire binding site.

As used herein, the term "immunoadhesin" designates molecules which combine the binding specificity of a heterologous protein (an "adhesin") with the effector functions of immunoglobulin constant domains. Structurally, the immunoadhesins comprise a fusion of an amino acid sequence with a desired binding specificity, which amino acid sequence is other than the antigen recognition and binding site of an antibody (i.e., is "heterologous" compared to a constant region of an antibody), and an immunoglobulin constant domain sequence (e.g., CH2 and/or CH3 sequence of an IgG). The adhesin and immunoglobulin constant domains may optionally be separated by an amino acid spacer. Exemplary adhesin sequences include contiguous amino acid sequences that comprise a portion of a receptor or a ligand that binds to a protein of interest. Adhesin sequences can also be sequences that bind a protein of interest, but are not receptor or ligand sequences (e.g., adhesin sequences in peptibodies). Such polypeptide sequences can be selected or identified by various methods, include phage display techniques and high throughput sorting methods. The immunoglobulin constant domain sequence in the immunoadhesin can be obtained from any immunoglobulin, such as IgG1, IgG2, IgG3, or IgG4 subtypes, IgA (including IgA1 and IgA2), IgE, IgD, or IgM.

By amino acid "spacer" as used herein is meant an amino acid sequence of two or more amino acids in length that is not cleavable, for example, by auto-cleavage, enzymatic, or chemical cleavage. The spacer can consist of neutral, polar, or nonpolar amino acids. An amino acid spacer can be, for example, 2 to 100 amino acids in length, such as between 10-80 amino acids or 20-40 amino acids in length, for example, 3, 5, 10, 15, 20, 25, 30, 35, or 40 amino acids in length. In some embodiments, an amino acid spacer may include glycine (G) and serine (S) residues, for example, as GGS repeats. In some embodiments, an amino acid spacer may include threonine (T) and histidine (H) residues. Exemplary spacers are THT (SEQ ID NO: 1), GGGSTHT (SEQ ID NO: 2), and GGGSGGGSTHT (SEQ ID NO: 3).

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and VL domains, which enables the sFv to form the desired structure for antigen binding. For a review of sFv, see Pluckthun, The Pharmacology of Monoclonal Antibodies, vol. 113, Rosenburg and Moore eds., Springer-Verlag, New York, pp. 269-315 (1994); Malmborg et al., J. Immunol. Methods 183:7-13, 1995.

The term "diabodies" refers to small antibody fragments prepared by constructing sFv fragments (see preceding paragraph) with short linkers (about 5-10 residues) between the VH and VL domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the VH and VL domains of the two antibodies are present on different polypeptide chains. Diabodies are described more fully in, for example, EP 404,097; WO 93/11161; and Hollinger et al., Proc. Natl. Acad. Sci. USA 90:6444-6448 (1993).

The expression "single domain antibodies" (sdAbs) or "single variable domain (SVD) antibodies" generally refers to antibodies in which a single variable domain (VH or VL) can confer antigen binding. In other words, the single variable domain does not need to interact with another variable domain in order to recognize the target antigen. Examples of single domain antibodies include those derived from camelids (llamas and camels) and cartilaginous fish (e.g., nurse sharks) and those derived from recombinant methods from humans and mouse antibodies (Nature (1989) 341:544-546; Dev Comp Immunol (2006) 30:43-56; Trend Biochem Sci (2001) 26:230-235; Trends Biotechnol (2003) 21:484-490; Febs Lett (1994) 339:285-290; WO00/29004; WO 02/051870).

The term "half-antibody" as used herein refers to one arm of an antibody and includes at least a VH domain and one CH domain. In some embodiments, a half-antibody may associate with an immunoadhesin to form a heteromultimer of the invention. In other embodiments, a first half-antibody may associate with a second half-antibody of identical or different amino acid sequence (e.g., differing by at least one amino acid residue) to form a symmetric or an asymmetric heteromultimer, respectively.

The term "single-chain antibody" is used herein in the broadest sense and specifically covers an antibody with monospecificity or multispecificity (e.g., bispecificity) that is initially generated as a single continuous polypeptide chain. Such single-chain antibodies include, but are not limited to, an antibody having two linked HCs, which can be different from or identical to one another and include two different or identical VH domains, an HD tether linking the two HCs, and at least one heavy chain constant domain selected from two different or identical CH2 domains and two different or identical CH3 domains. The single-chain antibodies may additionally include one or two, different or identical, CH1 domains. In some embodiments, the single-chain antibodies include one or two hinge domains, which link one HC domain (e.g., VH or CH1) with a second contiguously located domain (e.g., CH2). In other embodiments, the single-chain antibodies may include one or two linked LCs that can be different from or identical to one another and which may each include two different or identical VL and CL domains, each linked to a particular HC by a CLH tether. As described herein, the single-chain antibodies may additionally use knob-into-hole technology to support HC/HC or HC/LC heterodimerization and may include cleavable tethers. Single-chain antibodies are heteromultimers of the invention.

As used herein, the term "multi-chain antibody" refers to an antibody comprised of two LCs and two HCs, wherein the two HCs are expressed as a single polypeptide and at least one LC is expressed as a separate polypeptide. The independently expressed LCs associate with their cognate HCs to form an antibody with two functional arms. The multi-chain antibodies may be monospecific or multispecific. The multi-chain antibodies may additionally use knob-into-hole technology to support HC/HC or HC/LC heterodimerization and may include cleavable tethers.

The term "knob-into-hole" or "KnH" technology as mentioned herein refers to the technology directing the pairing of two polypeptides together in vitro or in vivo by introducing a protuberance (knob) into one polypeptide and a cavity (hole) into the other polypeptide at an interface in which they interact. For example, KnHs have been introduced in the Fc:Fc binding interfaces, CL:CH1 interfaces or VH/VL interfaces of antibodies (e.g., US2007/0178552, WO 96/027011, WO 98/050431 and Zhu et al. (1997) Protein Science 6:781-788). This is especially useful in driving the pairing of two different heavy chains together during the manufacture of multispecific antibodies. For example, multispecific antibodies having KnH in their Fc regions can further comprise single variable domains linked to each Fc region, or further comprise different heavy chain variable domains that pair with similar or different light chain variable domains. KnH technology can also be used to pair two different receptor extracellular domains together or any other polypeptide sequences that comprise different target recognition sequences.

The term "multispecific antibody" is used in the broadest sense and specifically covers an antibody that has polyepitopic specificity. Such multispecific antibodies include, but are not limited to, an antibody comprising a heavy chain variable domain (VH) and a light chain variable domain (VL), where the VH/VL unit has polyepitopic specificity, antibodies having two or more VL and VH domains with each VH/VL unit binding to a different epitope, antibodies having two or more single variable domains with each single variable domain binding to a different epitope, full-length antibodies, antibody fragments such as Fab, Fv, dsFv, scFv, diabodies, bispecific diabodies and triabodies, antibody fragments that have been linked covalently or non-covalently. "Polyepitopic specificity" refers to the ability to specifically bind to two or more different epitopes on the same or different target(s). "Monospecific" refers to the ability to bind only one antigen. In one embodiment, the monospecific heteromultimer binds two different epitopes on the same target/antigen. According to one embodiment, the multispecific antibody is an IgG antibody that binds to each epitope with an affinity of 5 μM to 0.001 pM, 3 μM to 0.001 pM, 1 μM to 0.001 pM, 0.5 μM to 0.001 pM, or 0.1 μM to 0.001 pM.

Antibodies of the invention can be "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, provided that they exhibit the desired biological activity (U.S. Pat. No. 4,816,567; and Morrison et ah, Proc. Natl. Acad. Sci. USA 81:6851-6855 (1984)). Chimeric antibodies of interest herein include primatized antibodies comprising variable domain antigen-binding sequences derived from a non-human primate (e.g., Old World Monkey, Ape, etc.) and human constant region sequences.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all or at least one, and typically two, variable domains, in which all or substantially all of the hypervariable loops correspond to those of a non-human immunoglobulin and all, or substantially all, of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al, Nature 332:323-329 (1988); and Presta, Curr. Op. Struct. Biol. 2:593-596 (1992).

"Complex" or "complexed" as used herein refers to the association of two or more molecules that interact with each other through bonds and/or forces (e.g., Van der Waals, hydrophobic, hydrophilic forces) that are not peptide bonds. In one embodiment, the complex is heteromultimeric. It should be understood that the term "protein complex" or "polypeptide complex" as used herein includes complexes that have a non-protein entity conjugated to a protein in the protein complex (e.g., including, but not limited to, chemical molecules such as a toxin or a detection agent).

The term "heteromultimer" or "heteromultimeric" as used herein describes two or more polypeptides of different sequence that interact with each other by a non-peptidic, covalent bond (e.g., disulfide bond) and/or a non-covalent interaction (e.g., hydrogen bonds, ionic bonds, Van der Waals forces, or hydrophobic interactions). Also included in this definition are multimeric polypeptides in an initially linked form (e.g., as produced in the form of a single continuous polypeptide chain). As used herein, heteromultimers include, for example, single-chain antibodies and multi-chain antibodies, as well as multimers having one or more half antibodies associated with one or more immunoadhesins. Heteromultimers include polypeptides and/or polypeptide complexes in which an HD tether is present or absent.

An antibody of this invention "which binds" an antigen of interest is one that binds the antigen with sufficient affinity such that the antibody is useful as a diagnostic and/or therapeutic agent in targeting a protein or a cell or tissue expressing the antigen, and does not significantly cross-react with other proteins. In such embodiments, the extent of binding of the antibody to a "non-target" protein will be less than about 10% of the binding of the antibody to its particular target protein as determined by fluorescence activated cell sorting (FACS) analysis or radioimmunoprecipitation (RIA) or ELISA. With regard to the binding of an antibody to a target molecule, the term "specific binding" or "specifically binds to" or is "specific for" a particular polypeptide or an epitope on a particular polypeptide target means binding that is measurably different from a non-specific interaction (e.g., a non-specific interaction may be binding to bovine serum albumin or casein). Specific binding can be measured, for example, by determining binding of a molecule compared to binding of a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of about 1 µM to about 1 fM, alternatively about 200 nM to about 1 fM, alternatively about 200 nM to about 1 pM, alternatively about 150 nM to about 1 fM, alternatively about 150 nM to about 1 pM, alternatively about 100 nM to about 1 fM, alternatively about 100 nM to about 1 pM, alternatively about 60 nM to about 1 fM, alternatively about 60 nM to about 1 pM, alternatively about 50 nM to about 1 fM, alternatively about 50 nM to about 1 pM, alternatively about 30 nM to about 1 fM, alternatively about 30 nM to about 1 pM, alternatively about 20 nM to about 1 fM, alternatively about 20 nM to about 1 pM, alternatively about 10 nM to about 1 fM, alternatively about 10 nM to about 1 pM, alternatively about 8 nM to about 1 fM, alternatively about 8 nM to about 1 pM, alternatively about 6 nM to about 1 fM, alternatively about 6 nM to about 1 pM, alternatively about 4 nM to about 1 fM, alternatively about 4 nM to about 1 pM, alternatively about 2 nM to about 1 fM, alternatively about 2 nM to about 1 pM, alternatively about 1 nM to about 1 fM, alternatively about 1 nM to about 1 pM. In one embodiment, the term "specific binding" refers to binding where a molecule binds to a particular polypeptide or epitope on a particular polypeptide without substantially binding to any other polypeptide or polypeptide epitope.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). For example, the Kd can be about 200 nM, 150 nM, 100 nM, 60 nM, 50 nM, 40 nM, 30 nM, 20 nM, 10 nM, 8 nM, 6 nM, 4 nM, 2 nM, 1 nM, or stronger. Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention.

In one embodiment, the "Kd" or "Kd value" according to this invention is measured by using surface plasmon resonance assays using a BIAcore™-2000 or a BIAcore™-3000 (BIAcore, Inc., Piscataway, N.J.) at 25° C. with immobilized antigen CM5 chips at ~10 response units (RU). The antibodies of this invention can have affinities for their targets with Kd values of about 1 µM to about 1 fM, alternatively about 200 nM to about 1 fM, alternatively about 200 nM to about 1 pM, alternatively about 150 nM to about 1 fM, alternatively about 150 nM to about 1 pM, alternatively about 100 nM to about 1 fM, alternatively about 100 nM to about 1 pM, alternatively about 60 nM to about 1 fM, alternatively about 60 nM to about 1 pM, alternatively about 50 nM to about 1 fM, alternatively about 50 nM to about 1 pM, alternatively about 30 nM to about 1 fM, alternatively about 30 nM to about 1 pM, alternatively about 20 nM to about 1 fM, alternatively about 20 nM to about 1 pM, alternatively about 10 nM to about 1 fM, alternatively about 10 nM to about 1 pM, alternatively about 8 nM to about 1 fM, alternatively about 8 nM to about 1 pM, alternatively about 6 nM to about 1 fM, alternatively about 6 nM to about 1 pM, alternatively about 4 nM to about 1 fM, alternatively about 4 nM to about 1 pM, alternatively about 2 nM to about 1 fM, alternatively about 2 nM to about 1 pM, alternatively about 1 nM to about 1 fM, alternatively about 1 nM to about 1 pM. To measure Kd values by using surface plasmon resonance assays, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 µg/ml (~0.2 µM) before injection at a flow rate of 5 µl/minute to achieve approximately 10 response units (RU) of coupled protein. Following the injection of antigen, 1M ethanolamine is injected to block unreacted groups. For kinetics measurements, two-fold serial dilutions of Fab (e.g., 0.78 nM to 500 nM) are injected in PBS with 0.05% Tween 20 (PBST) at 25° C. at a flow rate of approximately 25 µl/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) is calculated as the ratio $k_{off}/k_{on}$. See, e.g., Chen et al., J. Mol. Biol. 293:865-881 (1999). If the on-rate exceeds $10^6$ $M^{-1}S^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-Aminco spectrophotometer (ThermoSpectronic) with a stir red cuvette.

An "on-rate" or "rate of association" or "association rate" or "$k_{on}$" according to this invention can also be determined with the same surface plasmon resonance technique described above using a BIAcore™-2000 or a BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 µg/ml (~0.2 µM) before injection at a flow rate of 5 µl/minute to achieve approximately 10 response units (RU) of coupled protein. Following the injection of antigen, 1M ethanolamine is injected to block unreacted groups. For kinetics measurements, two-fold serial dilutions of Fab (e.g., 0.78 nM to 500 nM) are injected in PBS with 0.05% Tween 20 (PBST) at 25° C. at a flow rate of approximately 25 µl/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) is calculated as the ratio $k_{off}/k_{on}$. See, e.g., Chen et al., J. Mol. Biol. 293:865-881 (1999). However, if the on-rate exceeds $10^6$ $M^{-1}S^{-1}$ by the surface plasmon resonance assay above, then the on-rate is preferably determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stirred cuvette.

"Biologically active" and "biological activity" and "biological characteristics" with respect to a polypeptide of this invention, such as an antibody, fragment, or derivative thereof, means having the ability to bind to a biological molecule, except where specified otherwise.

The heteromultimers of the present invention are generally purified to substantial homogeneity. The phrases "substantially homogeneous," "substantially homogeneous form" and "substantial homogeneity" are used to indicate that the product is substantially devoid of by-products originated from undesired polypeptide combinations.

Expressed in terms of purity, substantial homogeneity means that the amount of byproducts does not exceed 10%, 9%, 8%, 7%, 6%, 4%, 3%, 2% or 1% by weight or is less than 1% by weight. In one embodiment, the by-product is below 5%.

"Biological molecule" refers to a nucleic acid, a protein, a carbohydrate, a lipid, and combinations thereof. In one embodiment, the biologic molecule exists in nature.

"Isolated," when used to describe the various heteromultimers disclosed herein, means a heteromultimer that has been identified and separated and/or recovered from a cell or cell culture from which it was expressed. Contaminant components of its natural environment are materials that would typically interfere with diagnostic or therapeutic uses for the polypeptide, and can include enzymes, hormones, and other proteinaceous or nonproteinaceous solutes. In preferred embodiments, the heteromultimer will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated heteromultimers include antibodies in situ within recombinant cells, because at least one component of the polypeptide natural environment will not be present. Ordinarily, however, isolated polypeptides will be prepared by at least one purification step.

By "linked" or "links" as used herein is meant either a direct peptide bond linkage between a first and second amino acid sequence or a linkage that involves a third amino acid sequence that is peptide bonded to and between the first and second amino acid sequences. For example, an amino acid linker bonded to the C-terminal end of one amino acid sequence and to the N-terminal end of the other amino acid sequence.

By "linker" as used herein is meant an amino acid sequence of two or more amino acids in length. The linker can consist of neutral, polar, or nonpolar amino acids. A linker can be, for example, 2 to 100 amino acids in length, such as between 2 and 50 amino acids in length, for example, 3, 5, 10, 15, 20, 25, 30, 35, 40, 45, or 50 amino acids in length. A linker can be "cleavable," for example, by auto-cleavage, or enzymatic or chemical cleavage. Cleavage sites in amino acid sequences and enzymes and chemicals that cleave at such sites are well known in the art and are also described herein.

By a "HD tether" or "HeteroDimerization tether" as used herein is meant an amino acid linker that joins two different heavy chain constant (CH) domain-containing polypeptides together. Generally, the two CH domain-containing polypeptides are joined together by linking a CH2 or CH3 domain of the first polypeptide to a VL domain, which is itself a component of a second CH-containing polypeptide. In some embodiments, the HD tether links the CH3 domain of a first polypeptide directly to the VH domain of a second CH domain-containing polypeptide. In general, HD tethers of 15-100 amino acids are effective, as are HD tethers of 20-40 amino acids, 25-40 amino acids, and 30-40 amino acids. In particular embodiments, an HD tether is between 30 and 39 amino acids in length (e.g., 30, 31, 32, 33, 34, 35, 36, 37, 38, or 39 amino acids in length). An HD tether may be "cleavable," for example, by auto-cleavage, or enzymatic or chemical cleavage using methods and reagents standard in the art.

By a "CLH tether" or "Cognate LC-HC tether" as used herein is meant an amino acid linker that joins a light chain with its cognate heavy chain. A CLH tether generally refers to amino acids that link the CL domain of a light chain to the VH domain of a heavy chain. In some embodiments, the CLH tether links the VL domain of a light chain directly to the VH domain of a heavy chain. In general, CLH tethers of 10-80 amino acids are effective, as are CLH tethers of 20-40 amino acids, 25-40 amino acids, 30-40 amino acids, and 30-35 amino acids (e.g., 30, 31, 32, 33, 34, or 35 amino acids). Single-chain antibodies of the invention may have multiple CLH tethers that may or may not differ in sequence and/or length. In preferred embodiments, a single-chain antibody has two tethers (CLH tether$_1$ and CLH tether$_2$) which each join a light chain to its cognate heavy chain. A CLH tether may be "cleavable," for example, by auto-cleavage, or enzymatic or chemical cleavage using methods and reagents standard in the art.

Enzymatic cleavage of a "linker" or a "tether" may involve the use of an endopeptidase such as, for example, urokinase, Lys-C, Asp-N, Arg-C, V8, Glu-C, chymotrypsin, trypsin, pepsin, papain, thrombin, tissue plasminogen activator (tPa), genenase, Factor Xa, TEV (tobacco etch virus cysteine protease), enterokinase, HRV C3 (human rhinovirus C3 protease), kininogenase, as well as subtilisin-like proprotein convertases (e.g., furin (PC1), PC2, or PC3) or N-arginine dibasic convertase. In a desirable embodiment, enzymatic cleavage involves the endopeptidase furin. Chemical cleavage may also involve use of, for example, hydroxylamine, N-chlorosuccinimide, N-bromosuccinimide, or cyanogen bromide.

A "furin endopeptidase cleavage site" as used herein is an $X_1$-$X_2$-$X_3$-Arginine amino acid sequence (SEQ ID NO:6), where $X_1$ is a basic amino acid residue (natural or unnatural, modified or unmodified) and $X_2$ and $X_3$ can be any amino acid residue (natural or unnatural, modified or unmodified) that can be cleaved at the C-terminal side by furin endopeptidase. Furin endopeptidase cleaves at the C-terminal side of an Arginine residue. In certain embodiments, the furin cleavage site comprises the amino acid sequence RXRXYR, wherein Y is K or R and X is any amino acid residue (SEQ ID NO:7), and more specifically RXRXRR (SEQ ID NO:8). In certain embodiments, the furin cleavage site comprises the amino acid sequence RKRKRR (SEQ ID NO:9). In certain other embodiments, the furin cleavage site comprises the amino acid sequence of RHRQPR (SEQ ID NO:10). In yet other embodiments, the furin cleavage site comprises the amino acid sequence RSRKRR (SEQ ID NO:11).

A "Lys-C endopeptidase cleavage site" as used herein is a Lysine residue in an amino acid sequence that can be cleaved at the C-terminal side by Lys-C endopeptidase. Lys-C endopeptidase cleaves at the C-terminal side of a Lysine residue.

Enzymatic cleavage of a "linker" or a "tether" may also involve the use of an exopeptidase such as, for example, Carboxypeptidase A, Carboxypeptidase B, Carboxypeptidase D, Carboxypeptidase E (also called Carboxypeptidase H), Carboxypeptidase M, Carboxypeptidase N, or Carboxypeptidase Z to remove the residual endopeptidase recognition sequences following endopeptidase cleavage.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxic agents. The antibodies "arm" the cytotoxic cells and are absolutely required for such killing. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch and Kinet, Annu. Rev. Immunol. 9:457-92 (1991). To assess ADCC activity of a molecule of interest, an in vitro ADCC assay, such as that described in U.S. Pat. No. 5,500,362 or 5,821,337 can be performed. Useful effector cells for such assays include peripheral blood mononuclear cells (PBMC) and Natural Killer (NK) cells. Alternatively, or additionally, ADCC activity of the molecule of interest can be assessed in vivo, e.g., in a animal model such as that disclosed in Clynes et al., Proc. Natl. Acad. Sci. USA 95:652-656 (1998).

"Fc receptor" or "FcR" describes a receptor that binds to the Fc region of an antibody. The preferred FcR is a native sequence human FcR. Moreover, a preferred FcR is one that binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain Inhibiting receptor FcγRIIB contains an immunoreceptor tyrosine-based inhibition motif (ITIM) in its cytoplasmic domain (see review M. in Daëron, Annu Rev. Immunol. 15:203-234 (1997)). FcRs are reviewed in Ravetch and Kinet, Annu. Rev. Immunol. 9:457-492 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976) and Kim et al., J. Immunol. 24:249 (1994)).

"Human effector cells" are leukocytes that express one or more FcRs and perform effector functions. Preferably, the cells express at least FcγRIII and perform ADCC effector function. Examples of human leukocytes that mediate ADCC include peripheral blood mononuclear cells (PBMC), natural killer (NK) cells, monocytes, cytotoxic T cells, and neutrophils; with PBMCs and NK cells being preferred. The effector cells can be isolated from a native source, e.g., from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) that are bound to their cognate antigen. To assess complement activation, a CDC assay, e.g., as described in Gazzano-Santoro et al., J. Immunol. Methods 202:163 (1996), can be performed.

The term "therapeutically effective amount" refers to an amount of heteromultimer, antibody, antibody fragment, or derivative to treat a disease or disorder in a subject. In the case of tumor (e.g., a cancerous tumor), the therapeutically effective amount of the heteromultimer, antibody, or antibody fragment (e.g., a multispecific antibody or antibody fragment) may reduce the number of cancer cells; reduce the primary tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the heteromultimer, antibody, or antibody fragment may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

By "reduce or inhibit" is meant the ability to cause an overall decrease preferably of 20% or greater, more preferably of 50% or greater, and most preferably of 75%, 85%, 90%, 95%, or greater. Reduce or inhibit can refer to the symptoms of the disorder being treated, the presence or size of metastases, the size of the primary tumor, or the size or number of the blood vessels in angiogenic disorders.

The term "cytotoxic agent" as used herein refers to a substance that inhibits or prevents the function of a cell and/or causes destruction of a cell. The term is intended to include radioactive isotopes (e.g., $At^{211}$, $I^{131}$, $I^{125}$, $Y^{90}$, $Re^{186}$, $Re^{188}$, $sm^{153}$, $Bi^{212}$, $Ra^{223}$, $P^{32}$, and radioactive isotopes of Lu), chemotherapeutic agents, e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor, anticancer, and chemotherapeutic agents disclosed herein. Other cytotoxic agents are described herein. A tumoricidal agent causes destruction of tumor cells.

A "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARTNOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma 1 (see, e.g., Agnew, Chem. Intl. Ed. Engl. 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, EL), and TAXOTERE® doxetaxel (Rhone-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluorometlhylomithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® GnRH antagonist; lapatinib ditosylate (an ErbB-2 and EGFR dual tyrosine kinase small-molecule inhibitor also known as GW572016); and pharmaceutically acceptable salts, acids or derivatives of any of the above.

A "growth inhibitory agent" when used herein refers to a compound or composition which inhibits growth of a cell either in vitro or in vivo. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (e.g., vincristine and vinblastine), taxanes, and topoisomerase II inhibitors such as doxorubicin, epirubicin, daunorubicin, etoposide, and bleomycin. The agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Anti-cancer therapy" as used herein refers to a treatment that reduces or inhibits cancer in a subject. Examples of anti-cancer therapy include cytotoxic radiotherapy as well as the administration of a therapeutically effective amount of a cytotoxic agent, a chemotherapeutic agent, a growth inhibitory agent, a cancer vaccine, an angiogenesis inhibitor, a prodrug, a cytokine, a cytokine antagonist, a corticosteroid, an immunosuppressive agent, an anti-emetic, an antibody or antibody fragment, or an analgesic to the subject.

"Target molecule" refers to a molecule which can bind to a protein complex of this invention (preferably with affinity higher than 1 µM Kd according to Scatchard analysis). Examples of target molecules include, but are not limited to, serum soluble proteins and their receptors, such as cytokines and cytokine receptors, adhesins, growth factors and their receptors, hormones, viral particles (e.g., RSVF protein, CMV, StaphA, influenza, hepatitis C virus), micoorganisms (e.g., bacterial cell proteins, fungal cells), adhesins, CD proteins and their receptors.

A "subject" is a vertebrate, such as a mammal, e.g., a human. Mammals include, but are not limited to, farm animals (such as cows), sport animals, pets (such as cats, dogs and horses), primates, mice, and rats.

Commercially available reagents referred to in the Examples were used according to manufacturer's instructions unless otherwise indicated. The source of those cells identified in the following Examples, and throughout the specification, by ATCC accession numbers is the American Type Culture Collection, Manassas, Va. Unless otherwise noted, the present invention uses standard procedures of recombinant DNA technology, such as those described hereinabove and in the following textbooks: Sambrook et al., supra; Ausubel et al., Current Protocols in Molecular Biology (Green Publishing Associates and Wiley Interscience, NY, 1989); Innis et al., PCR Protocols: A Guide to Methods and Applications (Academic Press, Inc., NY, 1990); Harlow et al., Antibodies: A Laboratory Manual (Cold Spring Harbor Press, Cold Spring Harbor, 1988); Gait, Oligonucleotide Synthesis (IRL Press, Oxford, 1984); Freshney, Animal Cell Culture, 1987; Coligan et al., Current Protocols in Immunology, 1991.

Throughout this specification and claims, the word "comprise," or variations such as "comprises" or "comprising," will be understood to imply the inclusion of a stated integer or group of integers but not the exclusion of any other integer or group of integers.

The term "prodrug" as used in this application refers to a precursor or derivative form of a pharmaceutically active substance that may optionally be less cytotoxic to tumor cells compared to the parent drug and is capable of being enzymatically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). Prodrugs include, but are not limited to, phosphate-containing prodrugs, thiophosphate-containing prodrugs, sulfate-containing prodrugs, peptide-containing prodrugs, D-amino acid-modified prodrugs, glycosylated prodrugs, beta-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone (HGH), N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); epidermal growth factor (EGF); hepatic growth factor; fibroblast growth factor (FGF); prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-α; platelet-growth factor; transforming growth factors (TGFs) such as TGF-alpha and TGF-β; insulin-like growth factor-I and -II; erythropoietin (EPO); osteoinductive factors; interferons such as interferon-alpha, -beta and -gamma colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-1β, IL-2, IL-3, IL-4, IL-5, IL-6, IL-7, IL-8, IL-9, IL-10, IL-11, IL-12; IL-18 a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

By "cytokine antagonist" is meant a molecule that partially or fully blocks, inhibits, or neutralizes a biological activity of at least one cytokine. For example, the cytokine antagonists may inhibit cytokine activity by inhibiting cytokine expression and/or secretion, or by binding to a cytokine or to a cytokine receptor. Cytokine antagonists include antibodies, heteromultimers, synthetic or native-sequence peptides, immunoadhesins, and small-molecule antagonists that bind to a cytokine or cytokine receptor. The cytokine antagonist is optionally conjugated with or fused to a cytotoxic agent.

The term "immunosuppressive agent" as used herein refers to substances that act to suppress or mask the immune system of the subject being treated. This includes substances that suppress cytokine production, downregulate or suppress self-antigen expression, or mask the MHC antigens. Examples of immunosuppressive agents include 2-amino-6-aryl-5-substituted pyrimidines (see U.S. Pat. No. 4,665,077); mycophenolate mofetil such as CELLCEPT®; azathioprine (IMURAN®, AZASAN®/6-mercaptopurine; bromocryptine; danazol; dapsone; glutaraldehyde (which masks the MHC antigens, as described in U.S. Pat. No. 4,120,649); anti-idiotypic antibodies for MHC antigens and MHC fragments; cyclosporin A; steroids such as corticosteroids and glucocorticosteroids, e.g., prednisone, prednisolone such as PEDIAPRED® (prednisolone sodium phosphate) or ORAPRED® (prednisolone sodium phosphate oral solution), methylprednisolone, and dexamethasone; methotrexate (oral or subcutaneous) (RHEUMATREX®, TREXALL™); hydroxycloroquine/chloroquine; sulfasalazine; leflunomide; cytokine or cytokine receptor antagonists including anti-interferon-γ, -β, or -α antibodies, anti-tumor necrosis factor-α antibodies (infliximab or adalimumab), anti-TNFα immunoadhesin (ENBREL®, etanercept), anti-tumor necrosis factor-β antibodies, anti-interleukin-2 antibodies and anti-IL-2 receptor antibodies; anti-LFA-1 antibodies, including anti-CD11a and anti-CD18 antibodies; anti-L3T4 antibodies; heterologous anti-lymphocyte globulin; polyclonal or pan-T antibodies, or monoclonal anti-CD3 or anti-CD4/CD4a antibodies; soluble peptide containing a LFA-3 binding domain (WO 90/08187); streptokinase; TGF-β; streptodornase; RNA or DNA from the host; FK506; RS-61443; deoxyspergualin; rapamycin; T-cell receptor (Cohen et al., U.S. Pat. No. 5,114,721); T-cell receptor fragments (Offner et al. Science 251: 430-432 (1991); WO 90/11294; Ianeway, Nature 341:482 (1989); and WO 91/01133); T cell receptor antibodies (EP 340,109) such as T10B9; cyclophosphamide (CYTOXAN®); dapsone; penicillamine (CUPRIMINE®); plasma exchange; or intravenous immunoglobulin (IVIG). These may be used alone or in combination with each other, particularly combinations of steroid and another immunosuppressive agent or such combinations followed by a maintenance dose with a non-steroid agent to reduce the need for steroids.

An "analgesic" refers to a drug that acts to inhibit or suppress pain in a subject. Exemplary analgesics include non-steroidal anti-inflammatory drugs (NSAIDs) including ibuprofen (MOTRIN®), naproxen (NAPROSYN®), acetyl-salicylic acid, indomethacin, sulindac, and tolmetin, including salts and derivatives thereof, as well as various other medications used to reduce the stabbing pains that may occur, including anticonvulsants (gabapentin, phenyloin, carbamazepine) or tricyclic antidepressants. Specific examples include acetaminophen, aspirin, amitriptyline (ELAVIL®), carbamazepine (TEGRETOL®), phenyltoin (DILANTIN®), gabapentin (NEURONTIN®), (E)-N-Vanillyl-8-methyl-6-noneamid (CAPSAICIN®), or a nerve blocker.

"Corticosteroid" refers to any one of several synthetic or naturally occurring substances with the general chemical structure of steroids that mimic or augment the effects of the naturally occurring corticosteroids. Examples of synthetic corticosteroids include prednisone, prednisolone (including methylprednisolone), dexamethasone triamcinolone, and betamethasone.

A "cancer vaccine," as used herein is a composition that stimulates an immune response in a subject against a cancer. Cancer vaccines typically consist of a source of cancer-associated material or cells (antigen) that may be autologous (from self) or allogenic (from others) to the subject, along with other components (e.g., adjuvants) to further stimulate and boost the immune response against the antigen. Cancer vaccines can result in stimulating the immune system of the subject to produce antibodies to one or several specific antigens, and/or to produce killer T cells to attack cancer cells that have those antigens.

An "anti-emetic" is a compound that reduces or prevents nausea in a subject. Anti-emetic compounds include, for example, neurokinin-1 receptor antagonists, 5HT3 receptor antagonists (such as ondansetron, granisetron, tropisetron, and zatisetron), GABAB receptor agonists, such as baclofen, a corticosteroid such as dexamethasone, KENALOG®, ARISTOCORT®, or NASALIDE®, an antidopaminergic, phenothiazines (for example prochlorperazine, fluphenazine, thioridazine and mesoridazine), dronabinol, metroclopramide, domperidone, haloperidol, cyclizine, lorazepam, prochlorperazine, and levomepromazine.

II. Construction of Single-Chain and Multi-Chain Tethered Antibodies and Other Heteromultimers Heteromultimers, including monospecific and multispecific (e.g., bispecific) antibodies, described herein may be constructed by using one or more tethers.

Use of tethers enables the construction of a relatively pure population of heteromultimers that have different heavy and/or light chains within a single heteromultimer. In particular, as described above, antibodies typically include two identical heavy chains, each of which is paired with one of two identical light chains. Use of the tether technology of the invention enables different antibody heavy chains to dimerize with each other in the formation of a single heteromultimeric antibody formed by a single polypeptide chain. The tethers can connect a first heavy chain to a second heavy chain, typically by linking a CH3 domain of a first heavy chain to a VL domain of a light chain, which itself is linked to a second heavy chain by a second tether. In a heteromultimeric single-chain antibody, a third tether may link a second light chain directly to the first heavy chain, thus resulting in a heteromultimer that includes two different heavy chains, which may each be paired with its cognate light chain. In other embodiments, the tethers can connect a first heavy chain to a second heavy chain directly by linking the C-terminus of a first heavy chain constant domain with the N-terminus of a second heavy chain variable domain. Each pair of heavy and light chains within such a heteromultimer may have different binding specificity due to the presence of the different heavy and light chain cognate pairs, and thus the heteromultimer can be considered as a multi-specific antibody. Use of the tether technology of the invention also enables the formation of a heteromultimer (e.g., a multi-chain antibody) that may include the association of three polypeptide chains, wherein one polypeptide chain includes two HCs connected directly together by an HD tether as described above, and the other two polypeptide chains are identical and form LCs which associate with the two HCs to form two functional HC/LC cognate pairs. In other embodiments, use of an HD and CLH tether enable the formation of a multi-specific antibody by two polypeptide chains, wherein one polypeptide chain forms a first LC and the other polypeptide chain includes two HCs and a second LC, which associates with the first HC via an HD tether and with the second HC via a CLH tether. In other embodiments, use of an HD and CLH tether enable the formation of a multi-specific antibody with two polypeptide chains, wherein the first polypeptide chain includes a first LC and two HCs, where one HC interacts with the first LC directly via a CLH tether and with the second HC directly via an HD tether, and the second polypeptide forms a second LC which associates with the HC that is not linked to the first LC. In other embodiments, use of the tether technology of the invention enables the formation of a heteromultimer in which an immunoadhesin associates with a half-antibody via an HD tether. The tether technology can be exploited alone or in combination with knob-into-hole ("KnH") technology to engineer the heteromultimers of the invention. Heteromultimers including tethers, with or without KnH technology, as well as recombinant heteromultimer production are described in detail below.

A. Heteromultimer Tethers

The invention provides heteromultimers constructed using tethers. For example, a heteromultimer can have a tether that links the C-terminus of an immunoglobulin heavy chain constant domain with the N-terminus of an immunoglobulin heavy chain variable domain. In other embodiments, the heteromultimer further includes one or more (e.g., two) additional tethers to aid in proper association of the heavy chain with its cognate light chain (i.e., association of the heavy chain with the light chain to which it is tethered). Such a heteromultimer can be constructed with or without an additional heterodimerizing domain, such as one created with KnH technology.

As depicted in the schematic diagram in FIG. 1, an exemplary heteromultimer is a multispecific single-chain antibody that contains two different heavy chains (HC1 and HC2) and two different light chains (LC1 and LC2), where HC1 and LC1 form a first cognate pair and HC2 and LC2 form a second cognate pair. In the exemplary heteromultimer, three tethers exist. A first tether (HD tether) links HC1 with LC2, and a second tether (CLH tether$_1$) and third tether (CLH tether$_2$) link LC1 with HC1 and LC2 with HC2, respectively. The tethers aid in bringing the two different heavy chains and their cognate light chains together, thereby generating a heteromultimeric single-chain antibody with multispecificity.

In a particular embodiment, the HD tether is long enough to span the distance between the C-terminus of HC1 and the N-terminus of LC2 (or, in the absence of LC2, HC2) in the assembled heteromultimer (FIG. 1) to allow for proper association of the first and second heavy chains, but is short enough to prevent intermolecular homodimerization of HC1 and/or HC2. The distances between the C-terminus of HC1 and the N-terminus of LC2 (or, in the absence of LC2, HC2) can differ between assembled heteromultimers, and thus the length of HD tethers can also vary between heteromultimers. In general, HD tethers of 15-100 amino acids are effective, as are HD tethers of 20-40 amino acids, 25-40 amino acids, and 30-40 amino acids. In particular embodiments, an HD tether is between 36 and 39 amino acids in length (e.g., 36, 37, 38, or 39 amino acids in length).

In a particular embodiment, the CLH tethers are each long enough to span the distance between the N-terminus of a heavy chain and the C-terminus of its cognate light chain in the assembled heteromultimer (FIG. 1) to allow for the proper light chain/heavy chain association, but are short enough to prevent unwanted intrachain association (i.e., the association of a light chain with a non-cognate heavy chain to which it is not directly tethered). The distances between the N-terminus of a heavy chain and the C-terminus of its cognate light chain can differ between antibodies, or even within the antibody itself (i.e., the distance between the N-terminus of a heavy chain and the C-terminus of a cognate light chain of the first cognate pair is different from that of the second cognate pair). Accordingly, the lengths of the HD tethers can vary between heteromultimers of the invention, and the length of CLH tether$_1$ may not equal the length of CLH tether$_2$ within the same heteromultimer. In general, CLH tethers of 10-80 amino acids are effective, as are CLH tethers of 20-40 amino acids, 25-40 amino acids, 30-40 amino acids, and 30-35 amino acids (e.g., 30, 31, 32, 33, 34, or 35 amino acids). Heteromultimers of the invention may have two tethers (CLH tether$_1$ and CLH tether$_2$) joining a first light chain with a first heavy chain and a second light chain with a second heavy chain.

Figure 2:
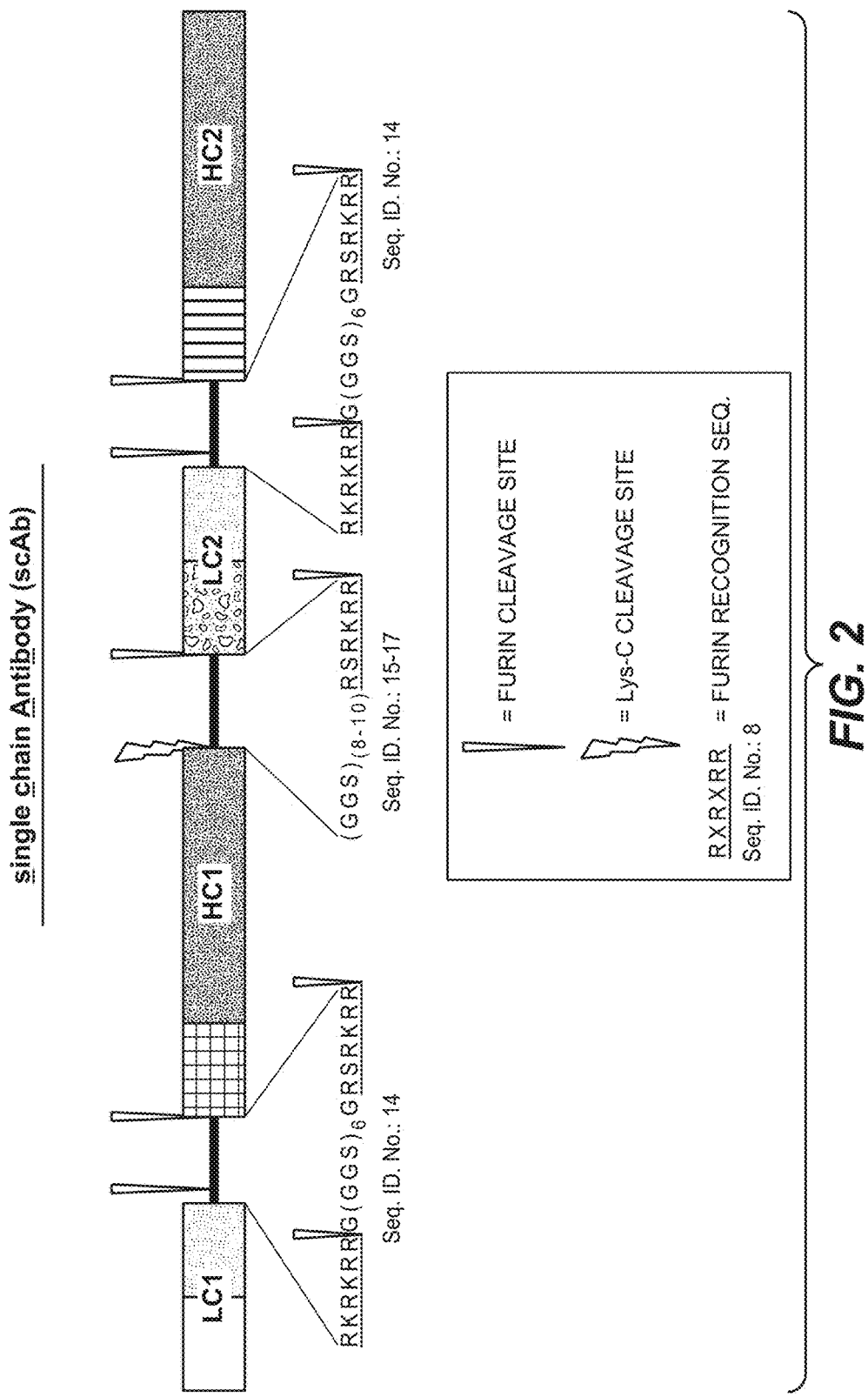
FIG. 2 is a schematic diagram showing the arrangement of an exemplary heteromultimeric single-chain antibody's LCs, HCs, tethers, and cleavage sites. The cleavage sites are exemplified by RKRKRRG(GGS)$_6$GRSRKRR (SEQ ID NO:14) and (GGS)$_{(8-10)}$ RSRKRR (SEQ ID NOs:15-17). The furin recognition site is illustrated as RXRXRR (SEQ ID NO:8).

An HD or CLH tether may remain flexible and not form secondary structures, and for this purpose tethers containing glycine (G) and serine (S) residues can be used. Tethers may consist solely of G and S residues, but also may include other residues, as long as the tethers remain flexible to allow for the intrachain associations described above. In particular embodiments, the HD or CLH tethers contain GGS repeats (FIG. 2). In some embodiments, the HD tether contains at least 1 GGS repeat. An exemplary HD tether described herein contains 8-9 GGS repeats (SEQ ID NO: 19) and endopeptidase cleavage sites (e.g., furin and Lys-C cleavage sites) at its N- and C-termini (FIG. 2). In another embodiment, the CLH tethers contain at least 1 GGS repeat. An exemplary CLH tether described herein contains 6 GGS repeats (SEQ ID NO: 20) and endopeptidase cleavage sites (e.g., furin cleavage sites) at its N- and C-termini (FIG. 2).

B. Cleavage of Heteromultimer Tethers

Once heteromultimers of the invention are assembled, the tethers may no longer be required and can, in some embodiments, be cleaved from the heteromultimers. Cleavage sites found in or immediately adjacent to the tethers, but either not present in the non-tether heteromultimer component sequences or not accessible for cleavage under the conditions used, can be used to remove the tethers.

FIG. 2 illustrates the location of exemplary cleavage sites in the three tethers that can exist within an exemplary heteromultimeric single-chain antibody. In general, cleavage sites in the tethers are located at or close to the C- and N-termini of the tether sequences or within the antibody sequence at or close to the site where the antibody and tether are joined. If one or more of the tethers are cleaved using Lys-C endopeptidase (e.g., at a Lysine residue at the C-terminus of the constant heavy chain), the sequence of the heteromultimer may need to be modified to remove Lys-C endopeptidase cleavage sites. An example of such a modification is the mutation of a lysine in the hinge region to an alanine (e.g., K222A, Kabat numbering system; K222A, EU numbering system in exemplary heteromultimers described herein). Modifications of other cleavage sites may be required and made in a similar manner when different cleavage agents are selected for use in the invention.

Figure 3A:
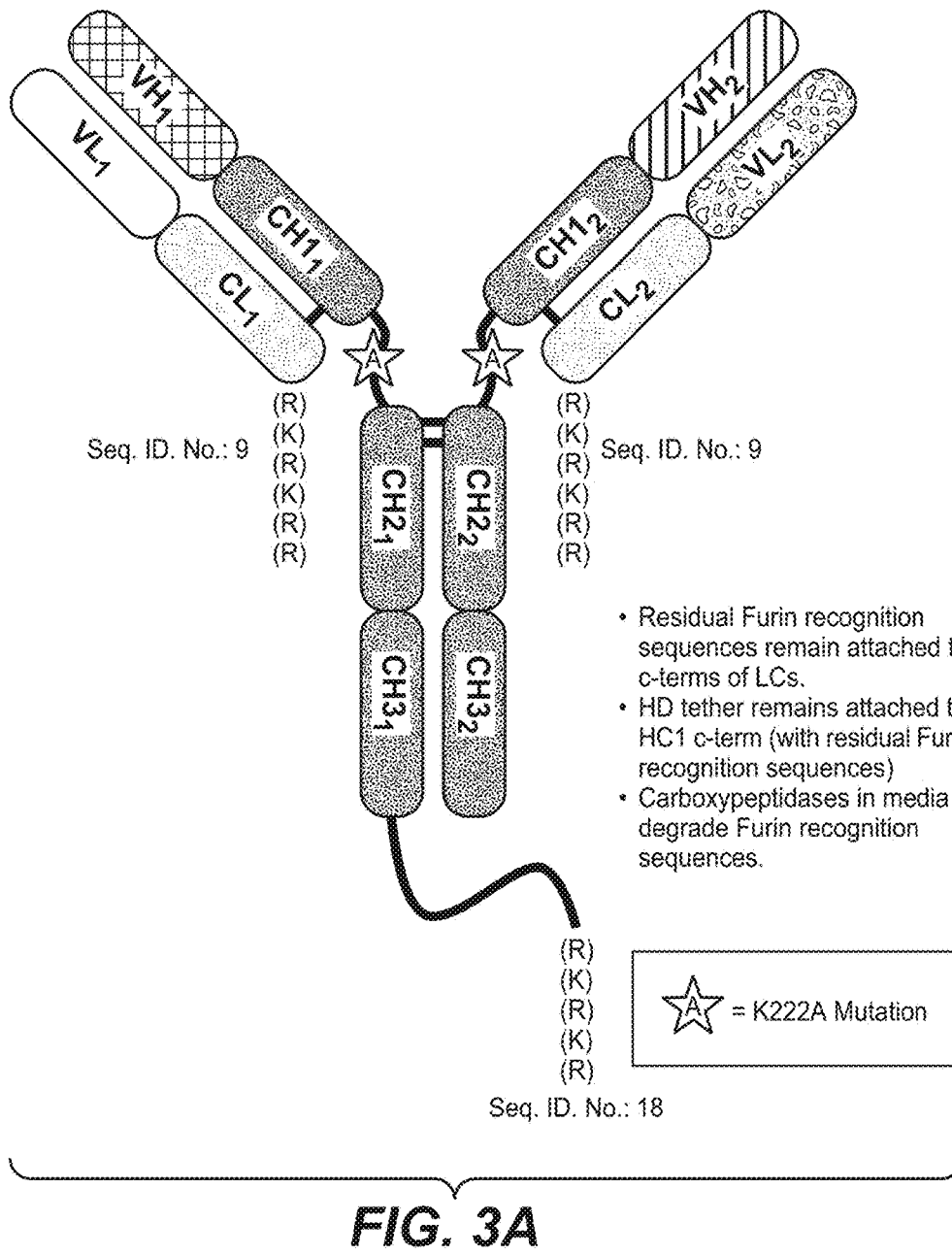
FIG. 3A is an example of a heteromultimeric single-chain antibody after furin cleavage. The residues in parentheses (RKRKRR (SEQ ID NO:9), and RKRKR (SEQ ID NO:18)) indicate residues that may be removed by endogenous exopeptidases prior to purification over the Protein A column resulting in ragged C-termini. Also depicted is an optional K222A mutation.

Cleavage of amino acid sequences at particular sites is standard in the art and can involve enzymatic cleavage, chemical cleavage, or auto-processing. For example, a tether may be cleaved from a protein using an endopeptidase. Exemplary endopeptidases include, without limitation, furin, urokinase, Lys-C, Asp-N, Arg-C, V8, Glu-C, thrombin, tissue plasminogen activator (tPa), genenase (a variant of subtilisin BPN' protease), Factor Xa, TEV (tobacco etch virus cysteine protease), enterokinase, HRV C3 (human rhinovirus C3 protease), kininogenase, chymotrypsin, trypsin, pepsin, and papain, all of which are commercially available (e.g., from Boehringer Mannheim, Thermo Scientific, or New England Biolabs). Subtilisin-like proprotein convertases such as furin (PC1), PC2, and PC3, (Steiner (1991) in Peptide Biosynthesis and Processing (Fricker ed.) pp. 1-16, CRC Press, Boca Raton, Fla.; Muller et al., JBC 275:39213-39222, (2000)) and N-arginine dibasic convertases (Chow et al., JBC 275:19545-19551 (2000)) cleave at dibasic sites. Lys-C cleaves at the carboxyl side of lysine residues, V8 and Glu-C cleave at the carboxyl side of Glutamate residues, Arg-C cleaves at the carboxyl side of arginine residues, Asp-N cleaves at the amino side of aspartate residues, chymotropsin cleaves at the carboxyl side of tyrosine, phenylalanine, tryptophan, and leucine residues, and trypsin cleaves at the carboxyl side of arginine and lysine residues. TEV cleaves the amino acid sequence GluAsnLeuTyrPheGlnGly (SEQ ID NO: 4) between the "Gln" and "Gly" residues. Use of such enzymes is standard in the art and protocols are available from the manufacturers. FIG. 3A shows an exemplary heteromultimeric single-chain antibody after cleavage with furin.

Alternatively a tether may be cleaved from a protein using a chemical, such as hydroxylamine. Hydroxylamine cleaves asparagine-glycine peptide bonds. If hydroxylamine is used to cleave the tether from a protein, several glycine or asparagine residues in the protein may need to be mutated to avoid fragmenting the protein.

Numerous other chemicals that cleave peptide bonds are known in the art. For example, N-chlorosuccinimide cleaves at the C-terminal side of tryptophan residues (Shechter et al., Biochemistry 15:5071-5075 (1976)). N-bromosuccinimide and cyanogen bromide also cleave at the C-terminal side of tryptophan residues. In addition, 2-nitrothiocyanobenzoic acid or organophosphines may be used to cleave a protein at the N-terminal side of a Cysteine residue (see, e.g., EP 0339217).

Proteins are also known to auto-process. For example, the Hedgehog protein is processed at a GlyAspTrpAsnAlaArg-TrpCysPhe cleavage site (SEQ ID NO: 5) by a proteolytic activity within the protein. An autoproteolytic cleavage site may also be included in a linker or tether sequence.

Figure 3B:
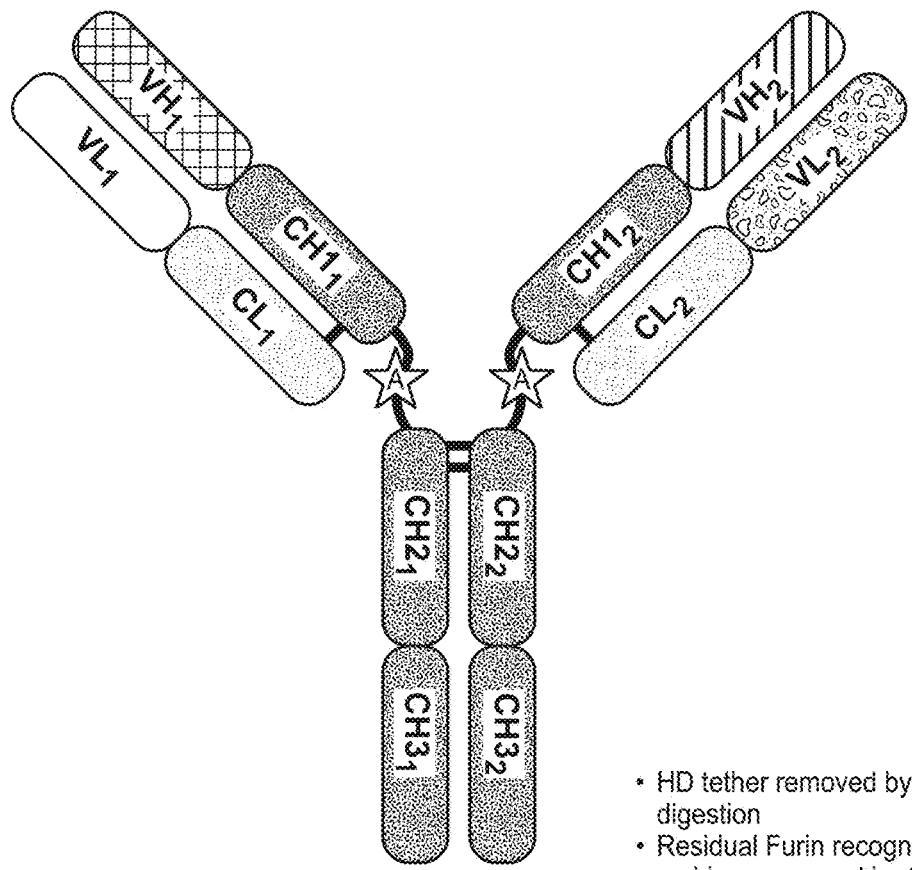
FIG. 3B is an example of a heteromultimeric single-chain antibody after furin, Lys-C, and exopeptidase (e.g., Carboxypeptidase B) treatment. Also depicted is an optional K222A mutation.

Following endopeptidase cleavage, the heteromultimers of the invention can be further processed by one or more exopeptidases either before or after purification of the heteromultimer. FIG. 3B shows a heteromultimeric single-chain antibody after purification and furin, Lys-C, and exopeptidase (e.g., Carboxypeptidase B) treatment. Following furin treatment, the HD tether still attached to the CH3$_1$ domain of the heteromultimer is removed by Lys-C treatment. The residual furin recognition sequences attached to the CL$_1$ and CL$_2$ domains are removed by treatment with an exopeptidase (e.g., Carboxypeptidase B).

C. Knob-into-Hole Technology

The heteromultimers of the invention may additionally include a heterodimerization domain using knob-into-hole (KnH) technology (see, e.g., U.S. Pat. No. 5,731,168, which is incorporated herein by reference in its entirety), which would engineer an interface between the two different antibody heavy chains to promote their association. In general, the method involves introducing a "protuberance" at the interface of a first heavy chain and a corresponding "cavity" in the interface of a second heavy chain, such that the protuberance can be positioned in the cavity so as to further promote heterodimerization of the heavy chains.

A first preferred interface includes at least part of the CH3 domain of a first heavy chain (CH3') constant domain and at least part of the CH3 domain of a second heavy chain (CH3$_2$) constant domain. Protuberances can be constructed by replacing small amino acid side chains from the interface of a first domain (e.g., CH3$_1$) with larger side chains (e.g., tyrosine or tryptophan). Compensatory cavities of identical or similar size to the protuberances are optionally created on the interface of a second domain (e.g., CH3$_2$) by replacing large amino acid side chains with smaller ones (e.g., alanine or threonine). A second preferred interface includes at least part of the CL domain of a light chain and at the CH1 domain of a heavy chain, at which a protuberance-cavity interaction can be constructed as described above. Where a suitably positioned and dimensioned protuberance or cavity exists at the interface of either the first or second domain, it is only necessary to engineer a corresponding cavity or protuberance, respectively, at the adjacent interface.

D. Monospecific or Multispecific Heteromultimers Having Different Binding Properties It should be understood that the variable domains of such heteromultimers can be derived from several methods. For example, the variable domains of the heteromultimers of this invention can be the same as existing antibodies known in the art.

As described above, an HD tether of the invention may be used to generate a heteromultimer having varied binding properties. In some embodiments, the invention may be used to generate a single-chain monospecific antibody that includes two half-antibodies with different binding affinities for the same target epitope. In another embodiment, the invention may be used to generate a single-chain multispecific antibody (an antibody that binds to at least two antigens or to at least two epitopes on the same antigen). Typically, in naturally occurring IgG antibodies, the variable regions of each pair of heavy and light chains in the antibody are identical. Use of tethers according to the present invention enables the two heavy chains within an antibody to be different, resulting in antibodies having antigen-binding domains with different binding specificities (e.g., epitope targets) or antigen-binding domains with the same binding specificities but different binding affinities. In some embodiments, the HD tether promotes association between two different heavy chains encoded within a single polypeptide chain to yield heavy-chain only, single-chain antibodies. In other embodiments, CLH tethers promote the association between a heavy chain and its cognate light chain. In some embodiments, the association between one of the heavy chains and its cognate light chain is established without a CLH tether to generate a heteromultimer of the invention. Optionally, one or more of the tethers include endopeptidase cleavage sites (e.g., furin and Lys-C cleavage sites), which can be cleaved so that the one or more tethers are removed from the heteromultimer after assembly. Optionally, the heteromultimer of this invention further includes one or more protuberance-cavity interfaces generated using KnH technology.

As depicted in FIG. 1, the exemplary bispecific heteromultimer (in this case, bispecific antibody) described above contains an HD tether and two CLH tethers, which may each include two furin cleavage sites at their N- and C-termini. Optionally, the exemplary heteromultimer can use KnH technology to further promote the association of HC1 and HC2.

Heteromultimers for which cleavage of tethers is anticipated should contain within its sequence no cleavage sites for the endopeptidase(s) used to cleave tethers or, if there are cleavage sites within the non-tether sequence of the heteromultimer, the cleavage sites should not be cleaved under the conditions used, unless cleavage of the heteromultimer is also intended. The sequence of a heteromultimer can be scanned to determine whether there are any cleavage sites (e.g., a furin or a Lys-C endopeptidase cleavage site) in the heavy or light chain sequences of the heteromultimer that would need to be removed to avoid cleavage of the heteromultimer itself upon removal of the tethers.

Single-chain monospecific or multispecific heteromultimers (e.g., antibodies) may be constructed using the methods described herein where the two different heavy chains of the heteromultimer are connected directly to one another by the HD tether. In one embodiment, the single-chain, heavy chain-only monospecific or multispecific heteromultimer may additionally lack CH1 domains (the VH domains are directly connected to at least one CH domain, optionally by hinges). In another embodiment, the single-chain monospecific or multispecific heteromultimer heavy chains lack CH1 domains, but associate with their corresponding light chains, which lack CL domains, via CLH tethers. Such heteromultimers can be used to bring two different antigens together or to associate B and T cells. In yet another embodiment, tethers may be utilized to associate a half-antibody with an immunoadhesin.

Further, the invention includes heteromultimers with monospecificity or multispecificity. In one embodiment, a first heavy chain, linked to its cognate light chain by a CLH tether, associates with a second heavy chain, whose cognate light chain associates with it independently of a tether.

E. Heteromultimers Having Different Effector Functions

In some embodiments, heteromultimers (e.g., single-chain or multi-chain antibodies, or antibody-immunoadhesin complexes) of the invention constructed using the methods described herein may include a CH2 domain mutation, allowing for altered effector function. Typically, the CH2 domain mutation is a mutation at N297 that may result in the heteromultimer having an altered glycosylation state. In certain embodiments, the N297 mutation is an N297A substitution. Altered effector functions include, but are not limited to, C1q binding and complement dependent cytotoxicity, Fc receptor binding, antibody-dependent cell-mediated cytotoxicity, phagocytosis, down regulation of cell surface receptors (e.g., B cell receptor), and B cell activation.

F. Conjugated Protein Complexes

Figure 4:
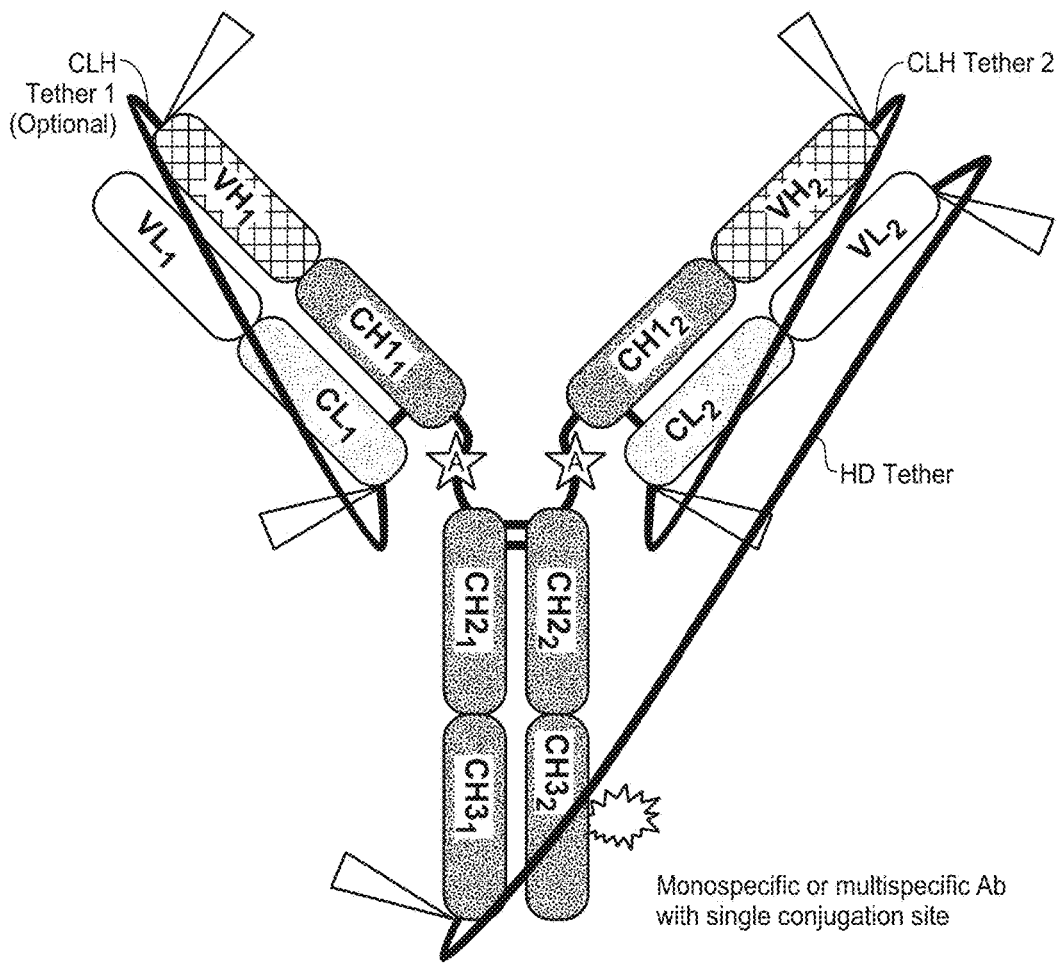
FIG. 4 is an exemplary conjugated heteromultimeric single-chain antibody prior to cleavage to remove the tethers. Also depicted is an optional conjugated moiety, e.g., toxin, antibiotic, etc., and optional K222A mutation.
Figure 5A:
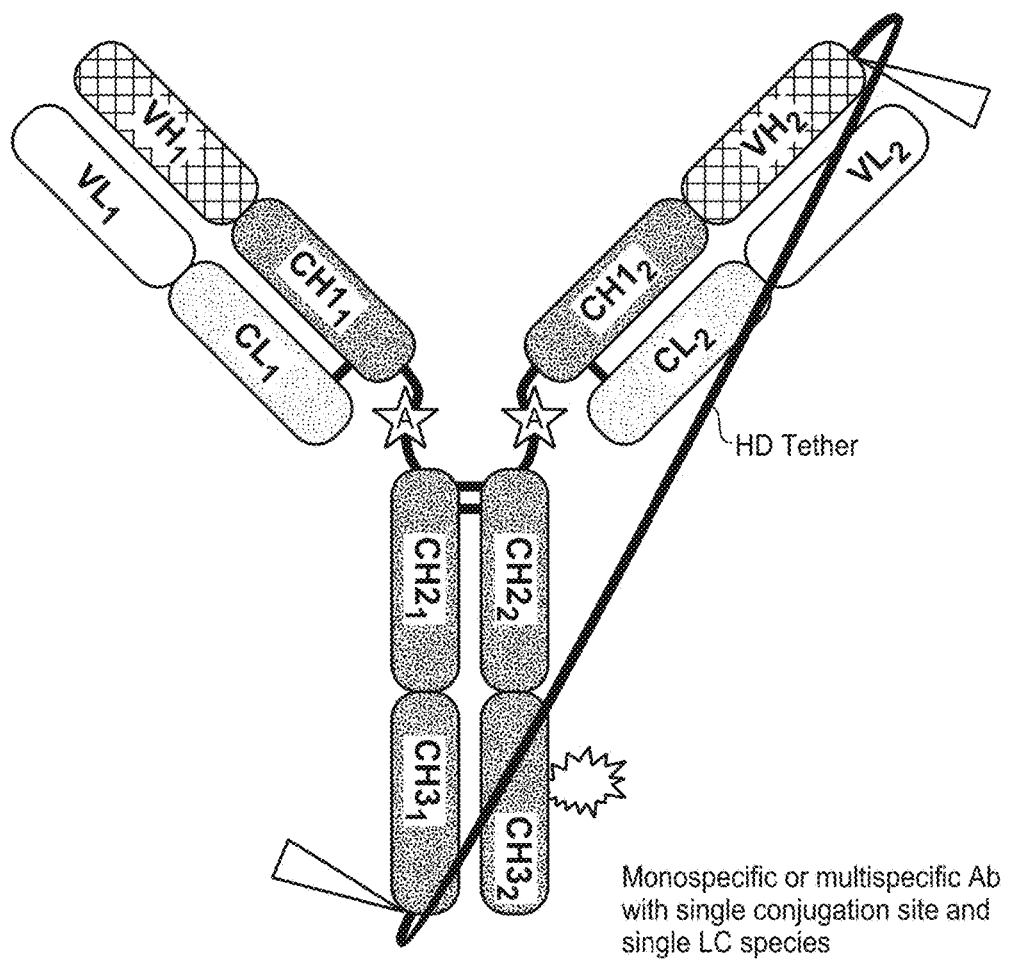
FIG. 5A is a schematic diagram showing the structure of an exemplary heteromultimeric multi-chain antibody containing one cleavable tether. The two untethered LCs may be expressed independently of the tether-containing polypeptide. The untethered LCs may be expressed in the same cell or in a different cell as the linked heavy chains. The untethered LC may be expressed on the same or different plasmid. Also depicted is an optional conjugated moiety, e.g., toxin, antibiotic, etc., and optional K222A mutation.
Figure 5B:
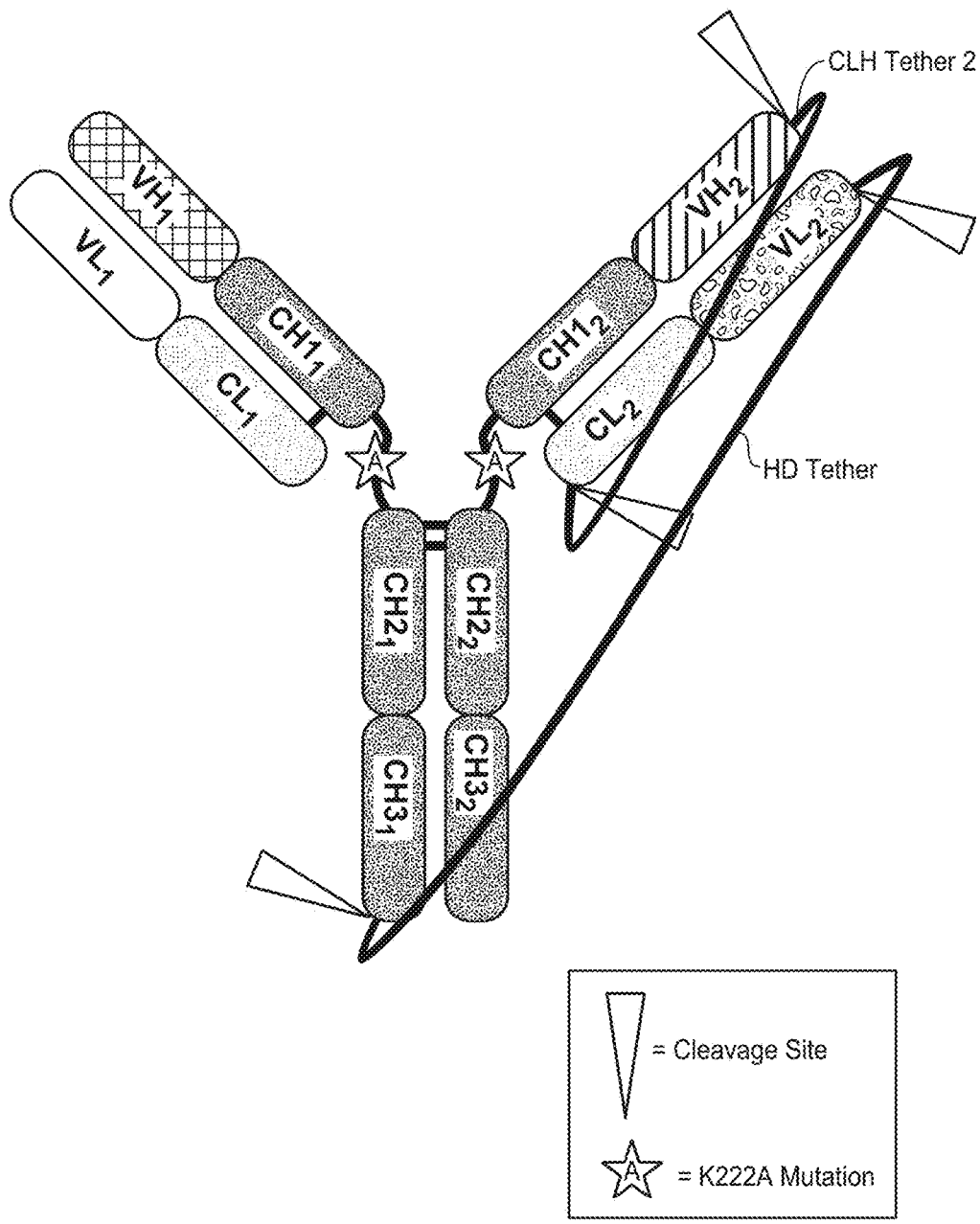
FIG. 5B is a schematic diagram showing the structure of an exemplary heteromultimeric multi-chain antibody containing two cleavable tethers. The HD tether links a first HC to a second HC indirectly by a tethered LC. The untethered LC may be expressed independently of the tether-containing polypeptide. The untethered LC may be expressed in the same cell or in a different cell as the linked heavy chains. The untethered LC may be expressed on the same or different plasmid. Also depicted is an optional K222A mutation.
Figure 5C:
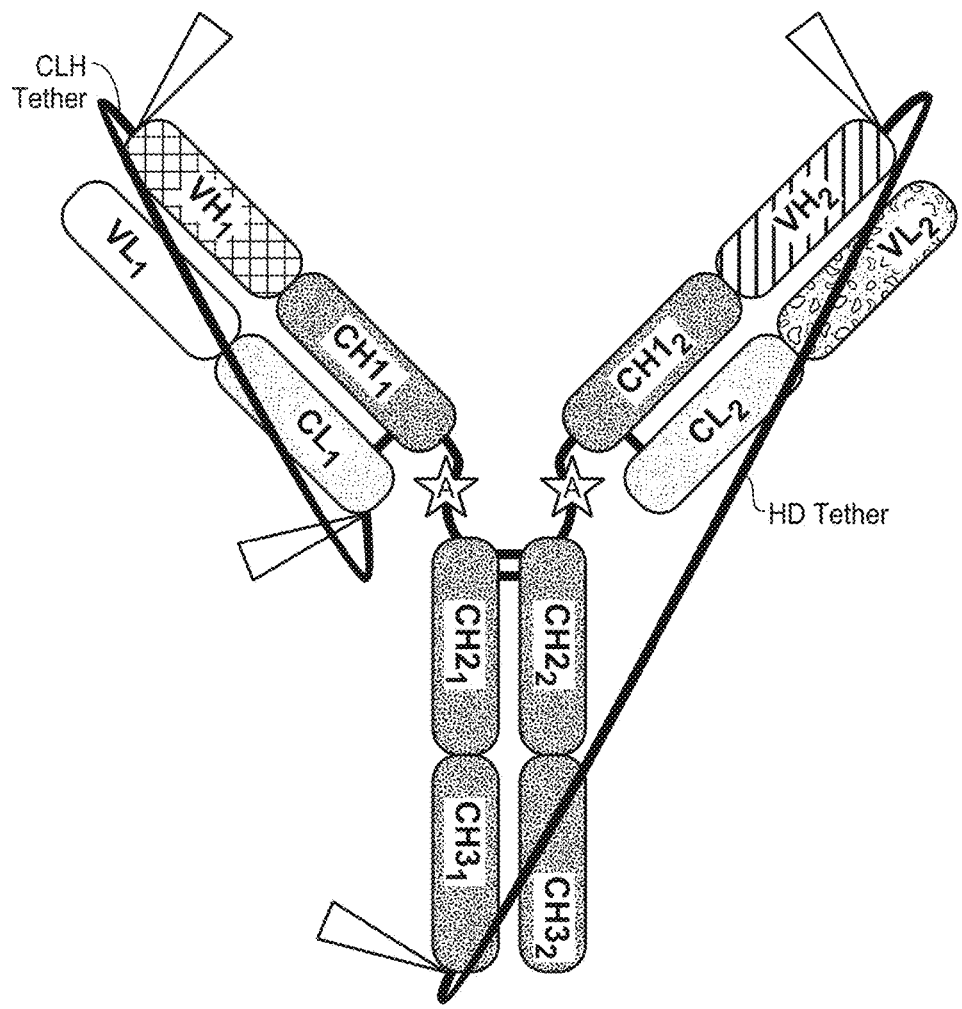
FIG. 5C is a schematic diagram showing the structure of an exemplary heteromultimeric multi-chain antibody containing two cleavable tethers. The HD tether links a first HC to a second HC directly. The untethered LC may be expressed independently of the tether-containing polypeptide. The untethered LC may be expressed in the same cell or in a different cell as the linked heavy chains. The untethered LC may be expressed on the same or different plasmid. Also depicted is an optional K222A mutation.
Figure 6A:
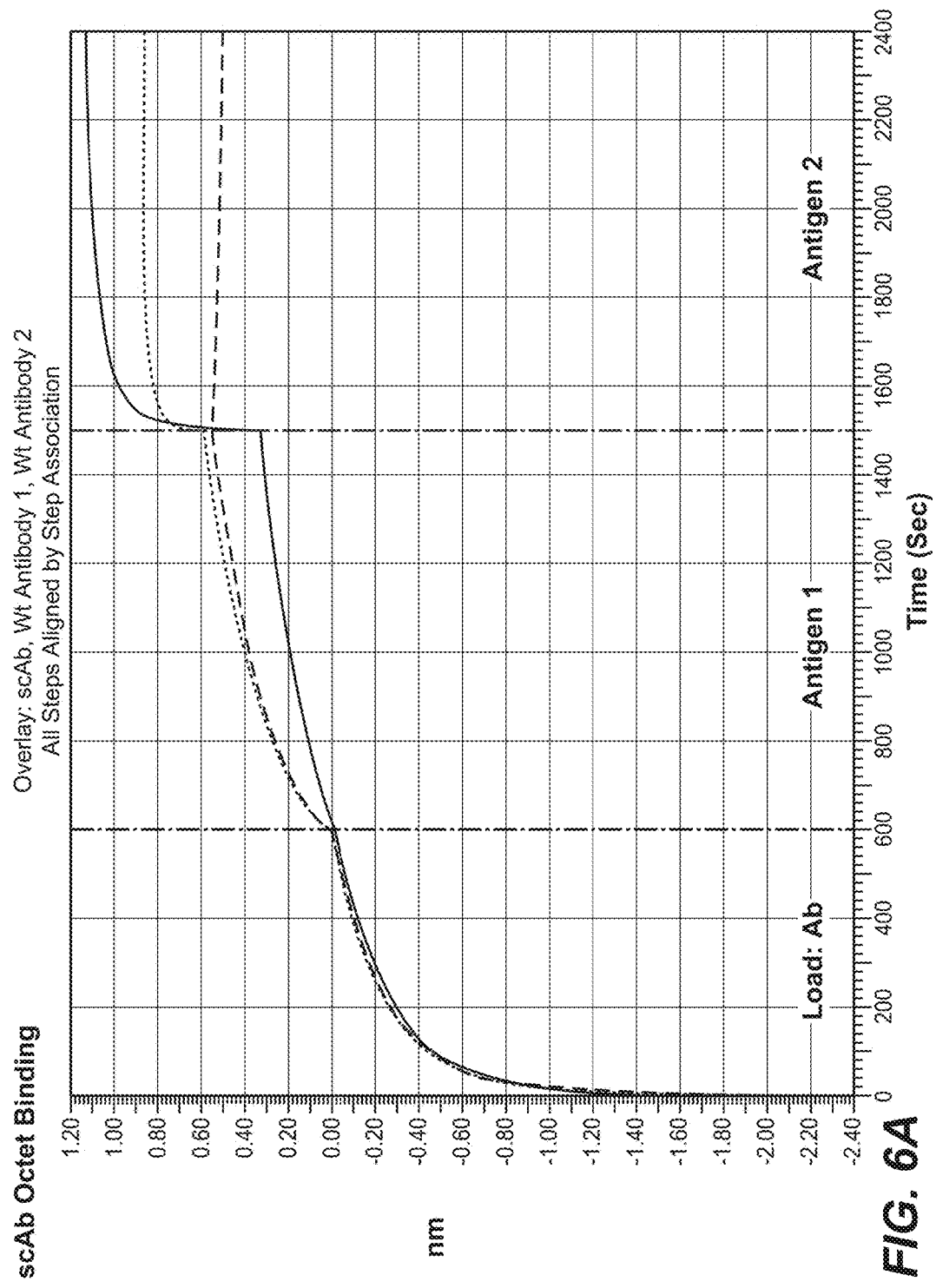
FIGS. 6A-6D are graphs showing the results from an Octet analysis. (A) A composite of the graphs shown in B-D. (B) The exemplary heteromultimeric single-chain antibody binds both antigen 1 and antigen 2 simultaneously. (C and D) Antibody 1 and antibody 2 do not cross react with each other's antigen, but do bind their respective antigen. The x-axis is time in seconds. The y-axis is a relative absorbance. Reference is made to Example 3.
Figure 6B:
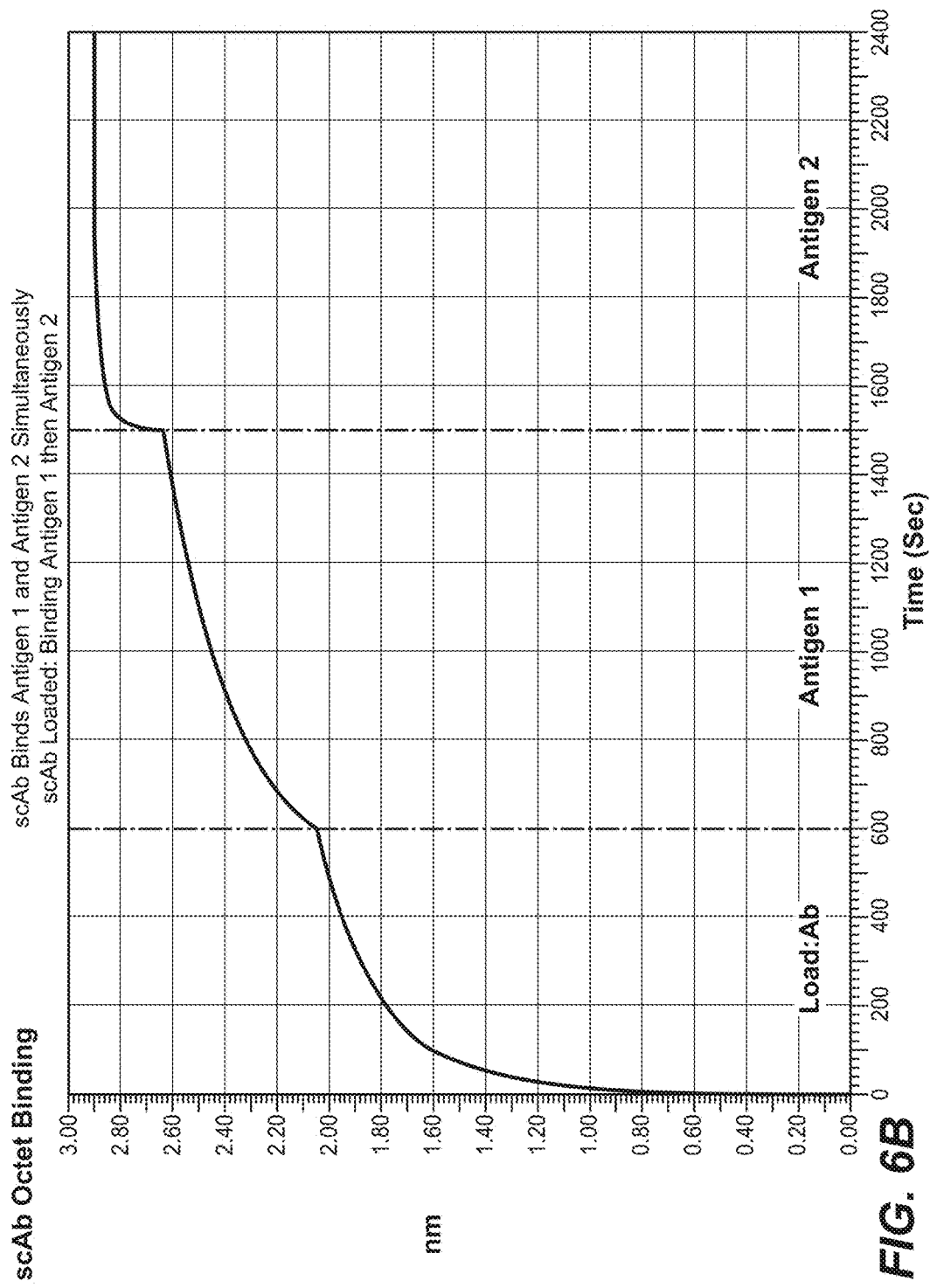
Figure 6C:
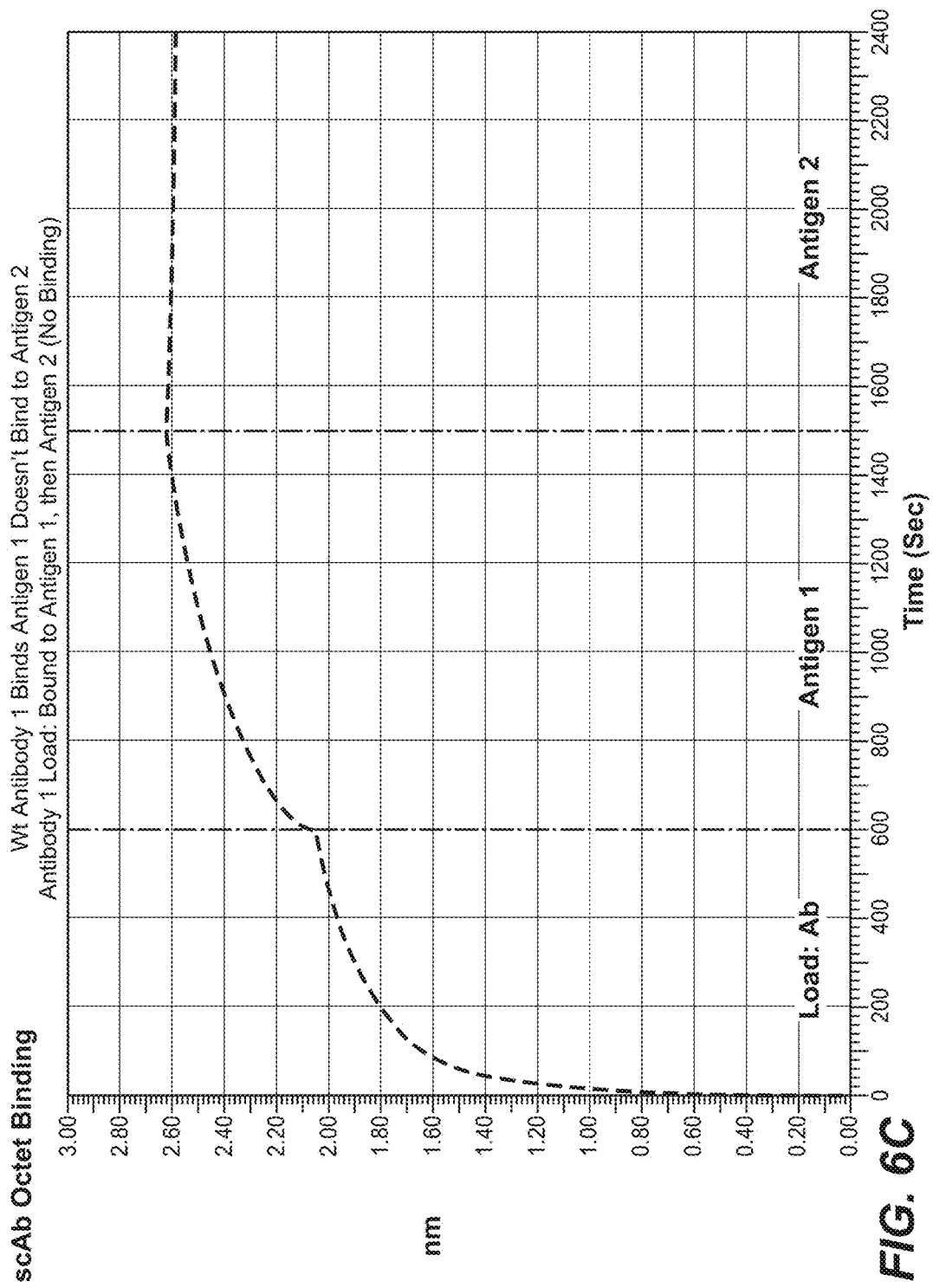
Figure 6D:
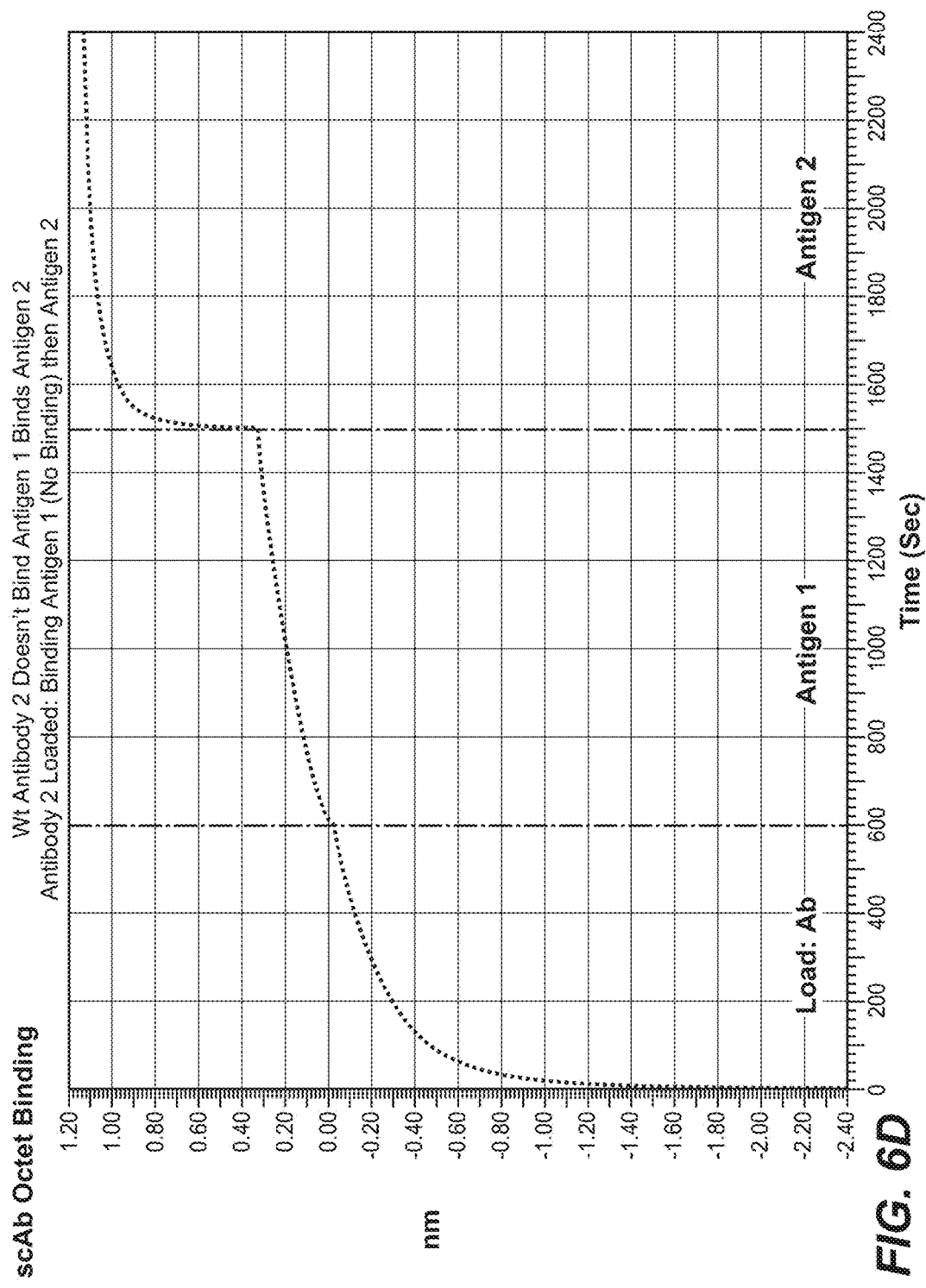

As described in detail below, the HD tether of the invention may also be used to generate protein complexes such heteromultimers (e.g., monospecific, bispecific, multispecific, single- or multi-chain antibodies) in which a constant region is modified by conjugation to a cytotoxic agent. For instance, the HD tether enables the construction of heteromultimers where one of the heavy chain constant regions (HC1 or HC2) contains a modification that allows for conjugation to a cytotoxic agent, while the other heavy chain constant region does not. In one example, HC1 is conjugated to a cytotoxic agent while HC2 is not. A schematic diagram illustrating an example of a conjugated heteromultimer of the invention is shown in FIG. 4. The exemplary heteromultimeric single-chain antibody includes two full-length heavy chains and cognate light chains, as well as the HD and CLH tethers described above. As indicated in FIG. 4, one of the heavy chains has been conjugated to a cytotoxic agent (e.g., a toxin or an antibiotic). Similarly, in an alternative heteromultimer construct, one of the light chain constant regions may be conjugated to a cytotoxic agent, while the other light chain constant region is not (e.g., LC1 is conjugated to a cytotoxic agent and LC2 is not). As depicted in FIG. 5A, the conjugated protein complex may be a multi-chain antibody of the invention. Conjugation of a cytotoxic agent is not limited to the specific multi-chain antibody depicted in FIG. 5A. Multi-chain antibodies, such as those depicted in FIG. 5B and FIG. 5C, as well as immunoadhesin-antibody heteromultimers may also be conjugated at a constant region.

In one particular example, a constant region of the heteromultimer may be modified to introduce electrophilic moieties which can react with nucleophilic substituents on a linker reagent used to conjugate the cytotoxic agent to the heteromultimer or on the cytotoxic agent itself. The sugars of glycosylated antibodies may be oxidized, e.g., with periodate oxidizing reagents, to form aldehyde or ketone groups which may react with the amine group of linker reagents or a cytotoxic agent. The resulting imine Schiff base groups may form a stable linkage, or may be reduced, e.g., by borohydride reagents, to form stable amine linkages. Nucleophilic groups on a cytotoxic agent include, but are not limited to, amine, thiol, hydroxyl, hydrazide, oxime, hydrazine, thiosemicarbazone, hydrazine carboxylate, and arylhydrazide groups capable of reacting to form covalent bonds with electrophilic groups on antibody regions and linker reagents including: (i) active esters such as NHS esters, HOBt esters, haloformates, and acid halides; (ii) alkyl and benzyl halides such as haloacetamides; and (iii) aldehydes, ketones, carboxyl, and maleimide groups.

G. Other Protein Features

Heteromultimers according to the invention can include sequences from any source, including human or murine sources, or combinations thereof. The sequences of certain portions of the proteins (e.g., the hypervariable regions) can also be artificial sequences, such as sequences identified by screening a library (e.g., a phage display library) including random sequences.

In the case of heteromultimers including sequences from different sources, the heteromultimers can be "chimeric" heteromultimers in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, provided that they exhibit the desired biological activity (U.S. Pat. No. 4,816,567; and Morrison et al., Proc. Natl. Acad. Sci. USA 81:6851-6855 (1984)). Such chimeric heteromultimers may, for example, include murine variable regions (or portions thereof) and human constant regions.

The chimeric single-chain heteromultimers can optionally also be "humanized" single-chain heteromultimers (e.g., single-chain antibodies), which contain minimal sequence derived from the non-human antibody. Humanized heteromultimers typically are derived from human antibodies (recipient antibody) in which residues from a hypervariable region of the recipient are replaced by residues from a hypervariable region of a non-human species (donor antibody) such as mouse, rat, rabbit or non-human primate having the desired specificity, affinity, and capability. In some instances, framework region (FR) residues of the human immunoglobulin are replaced by corresponding non-human residues. Furthermore, humanized heteromultimers can comprise residues that are not found in the recipient antibody or in the donor antibody. These modifications are made to further refine heteromultimer performance. In general, the humanized heteromultimer will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized heteromultimer optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

In more detail, a humanized heteromultimer can have one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al., Nature 321:522-525 (1986); Riechmann et al., Nature 332:323-327 (1988); Verhoeyen et al., Science 239:1534-1536 (1988)), by substituting rodent CDRs or CDR sequences for the corresponding sequences of a human antibody. Accordingly, such "humanized" heteromultimers are chimeric antibodies (U.S. Pat. No. 4,816,567) wherein substantially less than an intact human variable domain has been substituted by the corresponding sequence from a non-human species. In practice, humanized heteromultimers are typically human antibodies in which some CDR residues and possibly some FR residues are substituted by residues from analogous sites in rodent antibodies.

The choice of human variable domains, both light and heavy, to be used in making the humanized heteromultimers is very important to reduce antigenicity. According to the so-called "best-fit" method, the sequence of the variable domain of a rodent antibody is screened against the entire library of known human variable-domain sequences. The human sequence that is closest to that of the rodent is then accepted as the human framework (FR) for the humanized heteromultimer (Sims et al., J. Immunol. 151:2296 (1993); Chothia et al., J. Mol. Biol. 196:901 (1987)). Another method uses a particular framework derived from the consensus sequence of all human antibodies of a particular subgroup of light or heavy chains. The same framework may be used for several different humanized heteromultimers (Carter et al., Proc. Natl. Acad. Sci. USA 89:4285 (1992); Presta et al., J. Immnol. 151:2623 (1993)).

It is further important that heteromultimers be humanized with retention of high affinity for the one or more target antigens and other favorable biological properties. To achieve this goal, according to an exemplary method, humanized heteromultimers are prepared by a process of analysis of the parental sequences and various conceptual humanized products using three-dimensional models of the parental and humanized sequences. Three-dimensional immunoglobulin models are commonly available and are familiar to those skilled in the art. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired heteromultimer characteristic, such as increased affinity for the target antigen(s), is achieved. In general, the CDR residues are directly and most substantially involved in influencing antigen binding.

III. Vectors, Host Cells, and Recombinant Methods

For recombinant production of a heteromultimer of the invention, the nucleic acid encoding it is isolated and inserted into a replicable vector for further cloning (amplification of the DNA) or for expression. DNA encoding the heteromultimer is readily isolated and sequenced using conventional procedures (e.g., by using oligonucleotide probes that are capable of binding specifically to genes encoding the heavy and light chains of the heteromultimer). Many vectors are available. The choice of vector depends in part on the host cell to be used. Generally, preferred host cells are of either prokaryotic or eukaryotic (generally mammalian, but also including fungi (e.g., yeast), insect, plant, and nucleated cells from other multicellular organisms) origin. It will be appreciated that constant regions of any isotype can be used for this purpose, including IgG, IgM, IgA, IgD, and IgE constant regions, and that such constant regions can be obtained from any human or animal species.

A. Generating Heteromultimers Using Prokaryotic Host Cells i. Vector Construction Polynucleotide sequences encoding polypeptide components of the heteromultimer of the invention can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, $E.\ coli$ is typically transformed using pBR322, a plasmid derived from an $E.\ coli$ species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular heteromultimeric antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as λGEM-11™ may be utilized in making a recombinant vector which can be used to transform susceptible host cells such as $E.\ coli$ LE392.

The expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. An inducible promoter is a promoter that initiates increased levels of transcription of the cistron under its control in response to changes in the culture condition, e.g., the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker to ligate them to cistrons encoding the target light and heavy chains (Siebenlist et al., (1980) Cell 20:269) using linkers or adaptors to supply any required restriction sites.

In one aspect of the invention, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e., cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA, and MBP. In one embodiment of the invention, the signal sequences used in both cistrons of the expression system are STII signal sequences or variants thereof.

In another aspect, the production of the heteromultimers according to the invention can occur in the cytoplasm of the host cell, and therefore does not require the presence of secretion signal sequences within each cistron. In that regard, heteromultimer light and heavy chains are expressed, folded and assembled to form functional heteromultimers within the cytoplasm. Certain host strains (e.g., the $E.\ coli$ trxB-strains) provide cytoplasm conditions that are favorable for disulfide bond formation, thereby permitting proper folding and assembly of expressed protein subunits (Proba and Pluckthun, Gene, 159:203 (1995)).

Prokaryotic host cells suitable for expressing heteromultimers of the invention include Archaebacteria and Eubacteria, such as Gram-negative or Gram-positive organisms. Examples of useful bacteria include *Escherichia* (e.g., *E. coli*), *Bacilli* (e.g., *B. subtilis*), *Enterobacteria*, *Pseudomonas* species (e.g., *P. aeruginosa*), *Salmonella typhimurium*, *Serratia marcescans*, *Klebsiella*, *Proteus*, *Shigella*, *Rhizobia*, *Vitreoscilla*, or *Paracoccus*. In one embodiment, gram-negative cells are used. In one embodiment, *E. coli* cells are used as hosts for the invention. Examples of *E. coli* strains include strain W3110 (Bachmann, Cellular and Molecular Biology, vol. 2 (Washington, D.C.: American Society for Microbiology, 1987), pp. 1190-1219; ATCC Deposit No. 27,325) and derivatives thereof, including strain 33D3 having genotype W3110 ΔfhuA (ΔtonA) ptr3 lac Iq lacL8 ΔompTΔ(nmpc-fepE) degP41 kanR (U.S. Pat. No. 5,639,635). Other strains and derivatives thereof, such as *E. coli* 294 (ATCC 31,446), *E. coli* B, *E. coli* λ 1776 (ATCC 31,537) and *E. coli* RV308 (ATCC 31,608) are also suitable. These examples are illustrative rather than limiting. Methods for constructing derivatives of any of the above-mentioned bacteria having defined genotypes are known in the art and described in, for example, Bass et al., Proteins 8:309-314 (1990). It is generally necessary to select the appropriate bacteria taking into consideration replicability of the replicon in the cells of a bacterium. For example, *E. coli*, *Serratia*, or *Salmonella* species can be suitably used as the host when well-known plasmids such as pBR322, pBR325, pACYC 177, or pKN410 are used to supply the replicon. Typically the host cell should secrete minimal amounts of proteolytic enzymes, and additional protease inhibitors may desirably be incorporated in the cell culture.

ii. Heteromultimer Production

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extra-chromosomal element or as a chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the heteromultimers of the invention are grown in media known in the art and suitable for culture of the selected host cells. Examples of suitable media include Luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol, and dithiothreitol.

The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli*, the pH is preferably from about 6.8 to about 7.4, and more preferably about 7.0.

If an inducible promoter is used in the expression vector of the invention, protein expression is induced under conditions suitable for the activation of the promoter. In one aspect of the invention, PhoA promoters are used for controlling transcription of the polypeptides. Accordingly, the transformed host cells are cultured in a phosphate-limiting medium for induction. Preferably, the phosphate-limiting medium is the C.R.A.P medium (see, e.g., Simmons et al., J. Immunol. Methods (2002), 263:133-147). A variety of other inducers may be used, according to the vector construct employed, as is known in the art.

In one embodiment, the expressed heteromultimers of the present invention are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The heteromultimers may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In one aspect of the invention, heteromultimer production is conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (the preferred carbon/energy source). Small-scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an OD550 of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the heteromultimers of the invention, various fermentation conditions can be modified. For example, to improve the proper assembly and folding of the secreted heteromultimers, additional vectors overexpressing chaperone proteins, such as Dsb proteins (DsbA, DsbB, DsbC, DsbD, and/or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells (Chen et al., (1999) J. Biol. Chem. 274:19601-19605; Georgiou et al., U.S. Pat. No. 6,083,715; Georgiou et al., U.S. Pat. No. 6,027,888; Bothmann and Pluckthun (2000) J. Biol. Chem. 275:17100-17105; Ramm and Pluckthun, (2000) J. Biol. Chem. 275: 17106-17113; Arie et al., (2001) Mol. Microbiol. 39:199-210).

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI, and combinations thereof. Some *E. coli* protease-deficient strains are available and described in, for example, Joly et al., (1998), Proc. Natl. Acad. Sci. USA 95:2773-2777; Georgiou et al., U.S. Pat. No. 5,264,365; Georgiou et al., U.S. Pat. No. 5,508,192; Hara et al., Microbial Drug Resistance, 2:63-72 (1996).

In one embodiment, *E. coli* strains deficient for proteolytic enzymes and transformed with plasmids overexpressing one or more chaperone proteins are used as host cells in the expression system of the invention.

In another embodiment, the *E. coli* cell additionally expresses an endopeptidase (e.g., furin) to cleave the one or more tethers of the heteromultimer of interest prior to purification. In yet another embodiment, the eukaryotic host cell may express an endopeptidase (e.g., furin) and an exopeptidase (e.g., Carboxypeptidase B), where the endopeptidase cleaves the one or more tethers of the heteromultimer and the exopeptidase degrades the residual endopeptidase cleavage sites prior to purification.

iii. Heteromultimer Purification

Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, hydrophobic interaction columns (HIC), ammonium sulfate precipitation, and gel filtration using, for example, Sephadex G-75.

In one aspect, Protein A immobilized on a solid phase is used for immunoaffinity purification of the full-length heteromultimer products of the invention. Protein A is a 41-kD cell wall protein from *Staphylococcus aureus* which binds with a high affinity to the Fc region of antibodies. Lindmark et al., (1983) J. Immunol. Meth. 62:1-13. The solid phase to which Protein A is immobilized is preferably a column comprising a glass or silica surface, more preferably a controlled pore glass column or a silicic acid column. In some applications, the column has been coated with a reagent, such as glycerol, in an attempt to prevent nonspecific adherence of contaminants.

As the first step of purification, the preparation derived from the cell culture as described above is applied onto the Protein A immobilized solid phase to allow specific binding of the heteromultimer of interest to Protein A. The solid phase is then washed to remove contaminants non-specifically bound to the solid phase. The heteromultimer of interest may be recovered from the solid phase by elution into a solution containing a chaotropic agent or mild detergent. Exemplary chaotropic agents include, but are not limited to, urea, Guanidine-HCl, lithium perchlorate, Histidine, and Arginine. Exemplary mild detergents include, but are not limited to, Tween (e.g., Tween-20), Triton (e.g., Triton X-100), NP-40 (nonylphenoxylpolyethoxylethanol), Nonidet P-40 (octyl phenoxylpolyethoxylethanol), and Sodium Dodecyl Sulfate (SDS). Diluting the heteromultimer into a solution containing a chaotropic agent or mild detergent after elution from the column (e.g., mAbSure column) maintains the stability of the heteromultimer post-elution. In some embodiments, the one or more residual endopeptidase cleavage sites of the endopeptidase-treated heteromultimers of the invention can be processed and degraded post-purification by addition of exopeptidases (e.g., Carboxypeptidase B). In other embodiments, the one or more tethers of the heteromultimers of the invention can be cleaved and processed by endopeptidases (e.g., furin) and exopeptidases (e.g., Carboxypeptidase B) post-purification instead of pre-purification.

B. Generating Heteromultimers Using Eukaryotic Host Cells

The vector components generally include, but are not limited to, one or more of the following: a signal sequence, an origin of replication, one or more marker genes, an enhancer element, a promoter, and a transcription termination sequence.

i. Signal Sequence Component

A vector for use in a eukaryotic host cell may contain a signal sequence or other polypeptide having a specific cleavage site at the N-terminus of the mature protein or polypeptide of interest. The heterologous signal sequence selected can be one that is recognized and processed (i.e., cleaved by a signal peptidase) by the host cell. In mammalian cell expression, mammalian signal sequences as well as viral secretory leaders, for example, the herpes simplex gD signal, are available. The DNA for such precursor region is ligated in reading frame to DNA encoding the antibody.

ii. Origin of Replication

Generally, an origin of replication component is not needed for mammalian expression vectors. For example, the SV40 origin may typically be used, but only because it contains the early promoter.

iii. Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, where relevant, or (c) supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid, and hygromycin.

Another example of suitable selectable markers for mammalian cells are those that enable the identification of cells competent to take up the heteromultimer nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding an heteromultimer, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See, for example, U.S. Pat. No. 4,965,199.

iv. Promoter Component

Expression and cloning vectors usually contain a promoter that is recognized by the host organism and is operably linked to the nucleic acid sequence(s) encoding the heteromultimer. Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region (SEQ ID NO:12) where N may be any nucleotide. At the 3' end of most eukaryotic genes is an AATAAA sequence (SEQ ID NO:13) that may be the signal for addition of the poly A tail to the 3' end of the coding sequence. All of these sequences are suitably inserted into eukaryotic expression vectors.

Transcription from vectors encoding the heteromultimers in mammalian host cells is controlled, for example, by promoters obtained from the genomes of viruses such as, for example, polyoma virus, fowlpox virus, adenovirus (such as Adenovirus 2), bovine papilloma virus, avian sarcoma virus, cytomegalovirus, a retrovirus, hepatitis-B virus, and Simian Virus 40 (SV40), from heterologous mammalian promoters, e.g., the actin promoter or an immunoglobulin promoter, or from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papillomavirus as a vector is disclosed in U.S. Pat. No. 4,419,446. A modification of this system is described in U.S. Pat. No. 4,601,978. Alternatively, the Rous Sarcoma Virus long terminal repeat can be used as the promoter.

v. Enhancer Element Component

Transcription of DNA encoding heteromultimer polypeptide(s) by higher eukaryotes can be increased by inserting an enhancer sequence into the vector. Many enhancer sequences are now known from mammalian genes (e.g., globin, elastase, albumin, α-fetoprotein, and insulin genes). Also, one may use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) for a description of elements for enhancing activation of eukaryotic promoters. The enhancer may be spliced into the vector at a position 5' or 3' to the heteromultimer polypeptide-encoding sequence, provided that enhancement is achieved, but is generally located at a site 5' from the promoter.

vi. Transcription Termination Component

Expression vectors used in eukaryotic host cells will typically also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding a heteromultimer. One useful transcription termination component is the bovine growth hormone polyadenylation region. See WO 94/11026 and the expression vector disclosed therein.

vii. Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen. Virol. 36:59 (1977)); baby hamster kidney cells (BHK, ATCC CCL 10); Chinese hamster ovary cells/− DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for heteromultimer production and cultured in conventional nutrient media modified as appropriate for inducing promoters, selecting transformants, or amplifying the genes encoding the desired sequences.

viii. Culturing the Host Cells

The host cells used to produce a heteromultimer of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

ix. Purification of Heteromultimer

When using recombinant techniques, the heteromultimer can be produced intracellularly, or directly secreted into the medium. If the heteromultimer is produced intracellularly, as a first step, the particulate debris, either host cells or lysed fragments, are removed, for example, by centrifugation or ultrafiltration. Where the heteromultimer is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The heteromultimer composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the heteromultimer. Protein A can be used to purify heteromultimers that are based on human γ1, γ2, or γ4 heavy chains (Lindmark et al., J. Immunol. Meth. 62:1-13 (1983)). Protein G is recommended for all mouse isotypes and for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the heteromultimer comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

In one embodiment, the eukaryotic host cell additionally expresses an endopeptidase (e.g., furin) to cleave the one or more tethers of the heteromultimer of interest prior to purification (e.g., during trans-Golgi transport). In another embodiment, the eukaryotic host cell may express an endopeptidase (e.g., furin or Lys-C) and an exopeptidase (e.g., Carboxypeptidase B), where the endopeptidase cleaves the one or more tethers of the heteromultimer and the exopeptidase degrades the residual endopeptidase cleavage sites prior to purification.

The heteromultimer of interest is recovered from the solid phase of a column by elution into a solution containing a chaotropic agent or mild detergent. By a "chaotropic agent" is meant a water-soluble substance which disrupts the three-dimensional structure of a protein (e.g., an antibody) by interfering with stabilizing intramolecular interactions (e.g., hydrogen bonds, Van der Waals forces, or hydrophobic effects). Exemplary chaotropic agents include, but are not limited to, urea, Guanidine-HCl, lithium perchlorate, Histidine, and Arginine. By a "mild detergent" is meant a water-soluble substance which disrupts the three-dimensional structure of a protein or protein complex (e.g., a heteromultimer) by interfering with stabilizing intramolecular interactions (e.g., hydrogen bonds, Van der Waals forces, or hydrophobic effects), but which does not permanently disrupt the protein structure as to cause a loss of biological activity (i.e., does not denature the protein). Exemplary mild detergents include, but are not limited to, Tween (e.g., Tween-20), Triton (e.g., Triton X-100), NP-40 (nonylphenoxylpolyethoxyethanol), Nonidet P-40 (octyl phenoxylpolyethoxyethanol), and Sodium Dodecyl Sulfate (SDS).

Following any preliminary purification step(s), the mixture comprising the heteromultimer of interest and contaminants may be subjected to low pH hydrophobic interaction chromatography using an elution buffer at a pH between about 2.5-4.5, preferably performed at low salt concentrations (e.g., from about 0-0.25 M salt).

In some embodiments, the one or more residual endopeptidase cleavage sites of the endopeptidase-treated heteromultimers of the invention can be processed and degraded post-purification by exopeptidases (e.g., Carboxypeptidase B). In other embodiments, the one or more tethers of the heteromultimers of the invention can be cleaved and processed by endopeptidases (e.g., furin) and exopeptidases (e.g., Carboxypeptidase B) post-purification instead of pre-purification.

x. Heteromultimer Production Using Baculovirus

Recombinant baculovirus may be generated by co-transfecting a plasmid encoding heteromultimer or heteromultimer fragment and BaculoGold™ virus DNA (Pharmingen) into an insect cell such as a *Spodoptera frugiperda* cell (e.g., Sf9 cells; ATCC CRL 1711) or a *Drosophila melanogaster* S2 cell using, for example, lipofectin (commercially available from GIBCO-BRL). In a particular example, a heteromultimer sequence is fused upstream of an epitope tag contained within a baculovirus expression vector. Such epitope tags include poly-His tags. A variety of plasmids may be employed, including plasmids derived from commercially available plasmids such as pVL1393 (Novagen) or pAcGP67B (Pharmingen). Briefly, the sequence encoding antibody heteromultimer or a fragment thereof may be amplified by PCR with primers complementary to the 5' and 3' regions. The 5' primer may incorporate flanking (selected) restriction enzyme sites. The product may then be digested with the selected restriction enzymes and subcloned into the expression vector.

After tranfection with the expression vector, the host cells (e.g., Sf9 cells) are incubated for 4-5 days at 28° C. and the released virus is harvested and used for further amplifications. Viral infection and protein expression may be performed as described, for example, by O'Reilley et al. (Baculovirus expression vectors: A Laboratory Manual. Oxford: Oxford University Press (1994)).

Expressed poly-His tagged heteromultimer can then be purified, for example, by $Ni^{2+}$-chelate affinity chromatography as follows. Extracts can be prepared from recombinant virus-infected Sf9 cells as described by Rupert et al. (Nature 362:175-179 (1993)). Briefly, Sf9 cells are washed, resuspended in sonication buffer (25 mL HEPES pH 7.9; 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate; 300 mM NaCl; 10% glycerol pH 7.8) and filtered through a 0.45 µm filter. A $Ni^{2+}$-NTA agarose column (commercially available from Qiagen) is prepared with a bed volume of 5 mL, washed with 25 mL of water, and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl; 10% glycerol pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or Western blot with Ni$^{2+}$-NTA-conjugated to alkaline phosphatase (Qiagen). Fractions containing the eluted His$_{10}$-tagged (SEQ ID NO: 21) heteromultimer are pooled and dialyzed against loading buffer.

Purification of the heteromultimer can also be performed using known chromatography techniques, including for instance, Protein A or protein G column chromatography. The heteromultimer of interest may be recovered from the solid phase of the column by elution into a solution containing a chaotropic agent or mild detergent. Exemplary chaotropic agents and mild detergents include, but are not limited to, Guanidine-HCl, urea, lithium perchlorate, Arginine, Histidine, SDS (sodium dodecyl sulfate), Tween, Triton, and NP-40, all of which are commercially available. As described above, the one or more tethers of the heteromultimer may be cleaved and processed post-purification by addition of endopeptidase (e.g., furin or Lys-C) and exopeptidase (e.g., Carboxypeptidase B).

C. Purification Technique

One particular purification approach that may be used for HD tether-containing heteromultimers is shown below.

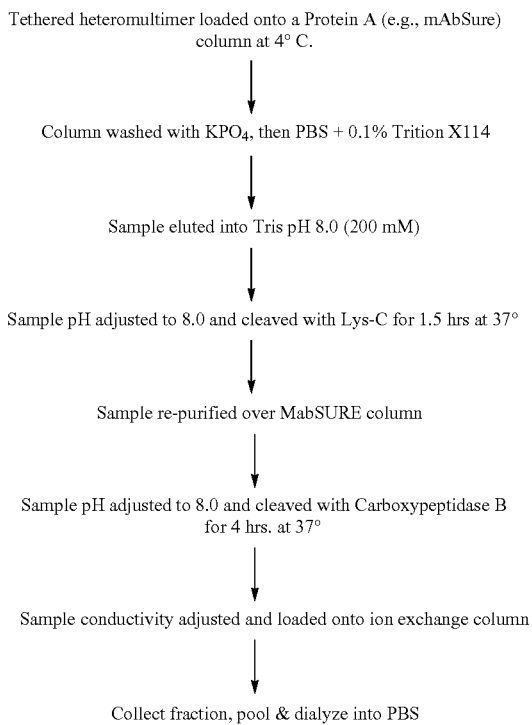

In addition to arginine, other chaotropic agents or mild detergents that can be used in the above purification protocol after the initial Protein A column step include, but are not limited to, Guanidine-HCl, urea, lithium perchlorate, histidine, SDS (sodium dodecyl sulfate), Tween, Triton, and NP-40, all of which are commercially available. In some embodiments, the one or more residual endopeptidase cleavage sites of the endopeptidase-treated heteromultimers of the invention can be processed and degraded post-purification by exopeptidases (e.g., Carboxypeptidase B). In other embodiments, the one or more tethers of the heteromultimers of the invention can be cleaved and processed by endopeptidases (e.g., furin or Lys-C) and exopeptidases (e.g., Carboxypeptidase B) post-purification instead of pre-purification.

IV. Conjugated Proteins

The invention also provides conjugated proteins such as conjugated heteromultimers or immunoconjugates (for example, "antibody-drug conjugates" or "ADC"), comprising any of the heteromultimers described herein (e.g., an HD tether-containing single-chain monospecific or multispecific antibody, an HD tether-containing multi-chain monospecific or multispecific heteromultimer) where one of the constant regions of the light chain or the heavy chain is conjugated to a chemical molecule such as a dye or cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate). In particular, as described herein, the use of an HD tether enables the construction of heteromultimers containing two different heavy chains (HC1 and HC2) as well as two different light chains (LC1 and LC2). An immunoconjugate constructed using the methods described herein may contain the cytotoxic agent conjugated to a constant region of only one of the heavy chains (HC1 or HC2) or only one of the light chains (LC1 or LC2). Also, because the immunoconjugate can have the cytotoxic agent attached to only one heavy or light chain, the amount of the cytotoxic agent being administered to a subject is reduced relative to administration of a heteromultimer having the cytotoxic agent attached to both heavy or light chains. Reducing the amount of cytotoxic agent being administered to a subject limits adverse side effects associated with the cytotoxic agent.

The use of antibody-drug conjugates for the local delivery of cytotoxic or cytostatic agents, i.e., drugs to kill or inhibit tumor cells in the treatment of cancer (Syrigos and Epenetos, Anticancer Research 19:605-614 (1999); Niculescu-Duvaz and Springer, Adv. Drg. Del. Rev. 26:151-172 (1997); U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., Lancet (Mar. 15, 1986):603-605 (1986); Thorpe, (1985) "Antibody Carriers Of Cytotoxic Agents In Cancer Therapy: A Review," in Monoclonal Antibodies'84: Biological And Clinical Applications, A. Pinchera et al. (ed.s), pp. 475-506). Maximal efficacy with minimal toxicity is sought thereby. Both polyclonal antibodies and monoclonal antibodies have been reported as useful in these strategies (Rowland et al., Cancer Immunol. Immunother. 21:183-187 (1986)). Drugs used in these methods include daunomycin, doxorubicin, methotrexate, and vindesine (Rowland et al., (1986) supra). Toxins used in heteromultimer-toxin conjugates include bacterial toxins such as diphtheria toxin, plant toxins such as ricin, small molecule toxins such as geldanamycin (Mandler et al., Jour. of the Nat. Cancer Inst. 92(19):1573-1581 (2000); Mandler et al., Bioorganic & Med. Chem. Letters 10:1025-1028 (2000); Mandler et al., Bioconjugate Chem. 13:786-791 (2002)), maytansinoids (EP 1391213; Liu et al., Proc. Natl. Acad. Sci. USA 93:8618-8623 (1996)), and calicheamicin (Lode et al., Cancer Res. 58:2928 (1998); Hinman et al., Cancer Res. 53:3336-3342 (1993)). The toxins may effect their cytotoxic and cytostatic effects by mechanisms including tubulin binding, DNA binding, or topoisomerase inhibition. Some cytotoxic drugs tend to be inactive or less active when conjugated to large heteromultimeric antibodies or protein receptor ligands.

Chemotherapeutic agents useful in the generation of immunoconjugates are described herein (e.g., above). Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. See, e.g., WO 93/21232 published Oct. 28, 1993. A variety of radionuclides are available for the production of radio-conjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See, e.g., WO94/11026.

Conjugates of a heteromultimer and one or more small molecule toxins, such as a calicheamicin, maytansinoids, dolastatins, aurostatins, a trichothecene, and CC 1065, and the derivatives of these toxins that have toxin activity, are also contemplated herein.

A. Maytansine and Maytansinoids

In some embodiments, the immunoconjugate comprises a heteromultimer of the invention conjugated to one or more maytansinoid molecules.

Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248, 870; 4,256,746; 4,260,608; 4,265,814; 4,294,757; 4,307, 016; 4,308,268; 4,308,269; 4,309,428; 4,313,946; 4,315, 929; 4,317,821; 4,322,348; 4,331,598; 4,361,650; 4,364, 866; 4,424,219; 4,450,254; 4,362,663; and 4,371,533.

Maytansinoid drug moieties are attractive drug moieties in heteromultimeric antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines.

Immunoconjugates containing maytansinoids, methods of making same, and their therapeutic use are disclosed, for example, in U.S. Pat. Nos. 5,208,020, 5,416,064 and European Patent EP 0 425 235 B1, the disclosures of which are hereby expressly incorporated by reference. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., Cancer Research 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansinoid conjugate was tested in vitro on the human breast cancer cell line SK-BR-3, which expresses $3 \times 10^5$ HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Maytansinoid conjugates are prepared by chemically linking a heteromultimer to a maytansinoid molecule without significantly diminishing the biological activity of either the heteromultimer, or the maytansinoid molecule. See, e.g., U.S. Pat. No. 5,208,020 (the disclosure of which is hereby expressly incorporated by reference). An average of 3-4 maytansinoid molecules conjugated per heteromultimeric antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making maytansinoid conjugates, including, for example, those disclosed in U.S. Pat. No. 5,208,020 or EP Patent 0 425 235 B1, Chari et al., Cancer Research 52:127-131 (1992), and U.S. Patent Application Publication No. 2005/ 0169933, the disclosures of which are hereby expressly incorporated by reference. Maytansinoid conjugates comprising the linker component SMCC may be prepared as disclosed in U.S. Patent Application Publication No. 2005/ 0169933. The linking groups include disulfide groups, thioether groups, acid labile groups, photolabile groups, peptidase labile groups, or esterase labile groups, as disclosed in the above-identified patents, disulfide and thioether groups being preferred. Additional linking groups are described and exemplified herein.

Conjugates of heteromultimer and maytansinoid may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5- difluoro-2,4-dinitrobenzene). Particularly preferred coupling agents include N-succinimidyl-3-(2-pyridyldithio) propionate (SPDP) (Carlsson et al., Biochem. J. 173:723-737 (1978)) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

B. Auristatins and Dolastatins

In some embodiments, the immunoconjugate comprises a heteromultimer of the invention conjugated to dolastatins or dolostatin peptidic analogs and derivatives, the auristatins (U.S. Pat. Nos. 5,635,483 and 5,780,588). Dolastatins and auristatins have been shown to interfere with microtubule dynamics, GTP hydrolysis, and nuclear and cellular division (Woyke et al., Antimicrob. Agents and Chemother. 45(12): 3580-3584 (2001)) and have anticancer (U.S. Pat. No. 5,663,149) and antifungal activity (Pettit et al., Antimicrob. Agents Chemother. 42:2961-2965 (1998)). The dolastatin or auristatin drug moiety may be attached to the heteromultimer through the N-(amino) terminus or the C-(carboxyl) terminus of the peptidic drug moiety (WO 02/088172).

Exemplary auristatin embodiments include the N-terminus linked monomethylauristatin drug moieties DE and DF, disclosed in "Monomethylvaline Compounds Capable of Conjugation to Ligands," U.S. Application Publication No. 2005/0238649, the disclosure of which is expressly incorporated by reference in its entirety.

Typically, peptide-based drug moieties can be prepared by forming a peptide bond between two or more amino acids and/or peptide fragments. Such peptide bonds can be prepared, for example, according to the liquid phase synthesis method (see E. Schröder and K. Lübke, "The Peptides," volume 1, pp. 76-136, 1965, Academic Press) that is well known in the field of peptide chemistry. The auristatin/dolastatin drug moieties may be prepared according to the methods of: U.S. Pat. Nos. 5,635,483 and 5,780,588; Pettit et al., J. Nat. Prod. 44:482-485 (1981); Pettit et al., Anti-Cancer Drug Design 13:47-66 (1998); Poncet, Curr. Pharm. Des. 5:139-162 (1999); and Pettit, Fortschr. Chem. Org. Naturst. 70:1-79 (1997). See also Doronina, Nat. Biotechnol. 21(7):778-784 (2003); and "Monomethylvaline Compounds Capable of Conjugation to Ligands," U.S. Application Publication No. 2005/0238649, hereby incorporated by reference in its entirety (disclosing, e.g., linkers and methods of preparing monomethylvaline compounds such as MMAE and MMAF conjugated to linkers).

C. Calicheamicin

In other embodiments, the immunoconjugate comprises a heteromultimer of the invention conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, and 5,877,296 (all to American Cyanamid Company). Structural analogues of calicheamicin which may be used include, but are not limited to, $\gamma_1^1$, $\alpha_2^1$, $\alpha_3^1$, N-acetyl-$\gamma_1^1$, PSAG and $\theta^1_1$ (Hinman et al., Cancer Research 53:3336-3342 (1993), Lode et al., Cancer Research 58:2925-2928 (1998) and the aforementioned U.S. patents to American Cyanamid). Another anti-tumor drug that the antibody can be conjugated is QFA, which is an antifolate. Both calicheamicin and QFA have intracellular sites of action and do not readily cross the plasma membrane. Therefore, cellular uptake of these agents through antibody-mediated internalization greatly enhances their cytotoxic effects.

D. Other Cytotoxic Agents

Other antitumor agents that can be conjugated to the heteromultimers of the invention or made according to the methods described herein include BCNU, streptozoicin, vincristine and 5-fluorouracil, the family of agents known collectively LL-E33288 complex described in U.S. Pat. Nos. 5,053,394 and 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes (see, for example, WO 93/21232, published Oct. 28, 1993).

The present invention further contemplates an immunoconjugate formed between a heteromultimer and a compound with nucleolytic activity (e.g., a ribonuclease or a DNA endonuclease such as a deoxyribonuclease; DNase).

For selective destruction of a tumor, the heteromultimer may comprise a highly radioactive atom. A variety of radioactive isotopes are available for the production of radioconjugated heteromultimers. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example $Tc^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al., Biochem. Biophys. Res. Commun. 80:49-57 (1978)) can be used to incorporate iodine-123. "Monoclonal Antibodies in Immunoscintigraphy" (Chatal, CRC Press 1989) describes other methods in detail.

Conjugates of the heteromultimer and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the heteromultimer. See, e.g., WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

The compounds of the invention expressly contemplate, but are not limited to, ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

E. Preparation of Conjugated Heteromultimers

In the conjugated heteromultimers of the invention, a heteromultimer is conjugated to one or more moieties (for example, drug moieties), e.g., about 1 to about 20 moieties per antibody, optionally through a linker. The conjugated heteromultimers may be prepared by several routes, employing organic chemistry reactions, conditions, and reagents known to those skilled in the art, including: (1) reaction of a nucleophilic group of antibody heteromultimer with a bivalent linker reagent via a covalent bond, followed by reaction with a moiety of interest; and (2) reaction of a nucleophilic group of a moiety with a bivalent linker reagent via a covalent bond, followed by reaction with the nucleophilic group of antibody heteromultimer. Additional methods for preparing conjugated heteromultimers are described herein.

The linker reagent may be composed of one or more linker components. Exemplary linker components include 6-maleimidocaproyl ("MC"), maleimidopropanoyl ("MP"), valine-citrulline ("val-cit"), alanine-phenylalanine ("ala-phe"), p-aminobenzyloxycarbonyl ("PAB"), N-Succinimidyl 4-(2-pyridylthio) pentanoate ("SPP"), N-Succinimidyl 4-(N-maleimidomethyl) cyclohexane-1 carboxylate ("SMCC"), and N-Succinimidyl (4-iodo-acetyl) aminobenzoate ("SIAB"). Additional linker components are known in the art and some are described herein. See also "Monomethylvaline Compounds Capable of Conjugation to Ligands," U.S. Application Publication No. 2005/0238649, the contents of which are hereby incorporated by reference in its entirety.

In some embodiments, the linker may comprise amino acid residues. Exemplary amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzymes, for example, a tumor-associated protease, cathepsin B, C and D, or a plasmin protease.

Nucleophilic groups on heteromultimers of the invention include, but are not limited to: (i) N-terminal amine groups, (ii) side chain amine groups, e.g. lysine, (iii) side chain thiol groups, e.g. cysteine, and (iv) sugar hydroxyl or amino groups where the heteromultimer is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain heteromultimers have reducible interchain disulfides, i.e., cysteine bridges. Heteromultimers of the invention may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the heteromultimer (or fragment thereof) by introducing one, two, three, four, or more cysteine residues (e.g., preparing mutant heteromultimers comprising one or more non-native cysteine amino acid residues).

Conjugated heteromultimers of the invention may also be produced by modification of the heteromultimer to introduce electrophilic moieties, which can react with nucleophilic substituents on the linker reagent or drug or other moiety. The sugars of glycosylated heteromultimers of the invention may be oxidized, e.g., with periodate oxidizing reagents, to form aldehyde or ketone groups which may react with the amine group of linker reagents or drug or other moieties. The resulting imine Schiff base groups may form a stable linkage, or may be reduced, e.g., by borohydride reagents to form stable amine linkages. In one embodiment, reaction of the carbohydrate portion of a glycosylated antibody with either glactose oxidase or sodium meta-periodate may yield carbonyl (aldehyde and ketone) groups in the protein that can react with appropriate groups on the drug or other moiety (Hermanson, Bioconjugate Techniques). In another embodiment, proteins containing N-terminal serine or threonine residues can react with sodium meta-periodate, resulting in production of an aldehyde in place of the first amino acid (Geoghegan and Stroh, Bioconjugate Chem. 3:138-146 (1992); U.S. Pat. No. 5,362,852). Such aldehyde can be reacted with a drug moiety or linker nucleophile.

Likewise, nucleophilic groups on a moiety (such as a drug moiety) include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; and (iii) aldehydes, ketones, carboxyl, and maleimide groups.

Alternatively, a fusion protein comprising the heteromultimer and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate. In yet another embodiment, the heteromultimer may be conjugated to a "receptor" (such streptavidin) for utilization in tumor pre-targeting wherein the heteromultimer-receptor conjugate is administered to the individual, followed by removal of unbound conjugate from the circulation using a clearing agent and then administration of a "ligand" (e.g., avidin) which is conjugated to a cytotoxic agent (e.g., a radionucleotide).

V. Therapeutic Uses

The heteromultimers described herein (e.g., an HD tether-containing single-chain monospecific or multispecific antibody, an HD tether-containing monospecific or multispecific antibody, an immunoadhesin-antibody complex) may be used for therapeutic applications. For example, such heteromultimers can be used for the treatment of any disease for which there is a suitable candidate target for heteromultimer generation, including proliferative diseases, cancer, angiogenic disorders, inflammatory disorders, autoimmune diseases, and immune disorders.

In addition to therapeutic uses, the heteromultimers of the invention can be used for other purposes, including diagnostic methods, such as diagnostic methods for any disease or condition for which there is a suitable candidate target for antibody generation, such as the above diseases or conditions.

VI. Dosages, Formulations, and Duration

The heteromultimers of this invention will be formulated, dosed, and administered in a fashion consistent with good medical practice. Factors for consideration in this context include the particular disorder being treated, the particular mammal being treated, the clinical condition of the individual subject, the cause of the disorder, the site of delivery of the agent, the method of administration, the scheduling of administration, and other factors known to medical practitioners. The "therapeutically effective amount" of the proteins to be administered will be governed by such considerations, and is the minimum amount necessary to prevent, ameliorate, or treat a particular disorder (e.g., a proliferative disease, cancer, an angiogenic disorder, an inflammatory disorder, an autoimmune disease, or an immune disorder). The proteins need not be, but are optionally, formulated with one or more agents currently used to prevent or treat the disorder. The effective amount of such other agents depends on the amount of proteins present in the formulation, the type of disorder or treatment, and other factors discussed above. These are generally used in the same dosages and with administration routes as used hereinbefore or about from 1 to 99% of the heretofore employed dosages.

In one embodiment, the present invention can be used for increasing the duration of survival of a human subject susceptible to or diagnosed with a particular disorder for which there is a suitable candidate target for heteromultimer generation. Duration of survival is defined as the time from first administration of the drug to death. Duration of survival can also be measured by stratified hazard ratio (HR) of the treatment group versus control group, which represents the risk of death for a subject during the treatment.

In yet another embodiment, the methods of the present invention significantly increases the response rate in a group of human subjects susceptible to or diagnosed with a disorder and whom are being treated with one or more therapies directed to the disorder. Response rate is defined as the percentage of treated subjects who responded to the treatment. In one aspect, the combination treatment of the invention using proteins of this invention and surgery or another form of therapy (e.g., radiation therapy or chemotherapeutic agents) significantly increases response rate in the treated subject group compared to the group treated with surgery or another form of therapy alone, the increase having a Chi-square p-value of less than 0.005. Additional measurements of therapeutic efficacy in the treatment of cancers are described in U.S. Patent Application Publication No. 20050186208.

Therapeutic formulations are prepared using standard methods known in the art by mixing the active ingredient having the desired degree of purity with optional physiologically acceptable carriers, excipients or stabilizers (Remington's Pharmaceutical Sciences ($20^{th}$ edition), ed. A. Gennaro, 2000, Lippincott, Williams & Wilkins, Philadelphia, Pa.). Acceptable carriers, include saline, or buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagines, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™, or PEG.

Optionally, but preferably, the formulation contains a pharmaceutically acceptable salt, preferably sodium chloride, and preferably at about physiological concentrations. Optionally, the formulations of the invention can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, and propylparaben are preferred preservatives. Optionally, the formulations of the invention can include a pharmaceutically acceptable surfactant at a concentration of 0.005 to 0.02%.

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, supra.

Sustained-release preparations may be prepared. Suitable examples of sustained-release preparations include semipermeable matrices of solid hydrophobic polymers containing the heteromultimer, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated heteromultimers of the invention remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The proteins described herein (e.g., an HD tether-containing single-chain monospecific or multispecific antibody, an HD tether-containing multi-chain monospecific or multispecific heteromultimer, an immunoadhesin-antibody complex) are administered to a human subject, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Local administration may be particularly desired if extensive side effects or toxicity is associated with antagonism to the target molecule recognized by the proteins. An ex vivo strategy can also be used for therapeutic applications. Ex vivo strategies involve transfecting or transducing cells obtained from the subject with a polynucleotide encoding a heteromultimer of this invention. The transfected or transduced cells are then returned to the subject. The cells can be any of a wide range of types including, without limitation, hemopoietic cells (e.g., bone marrow cells, macrophages, monocytes, dendritic cells, T cells, or B cells), fibroblasts, epithelial cells, endothelial cells, keratinocytes, or muscle cells.

In one example, the heteromultimer of the invention is administered locally, e.g., by direct injections, when the disorder or location of the tumor permits, and the injections can be repeated periodically. The protein complex can also be delivered systemically to the subject or directly to the tumor cells, e.g., to a tumor or a tumor bed following surgical excision of the tumor, in order to prevent or reduce local recurrence or metastasis.

VII. Articles of Manufacture

Another embodiment of the invention is an article of manufacture containing one or more heteromultimer described herein, and materials useful for the treatment or diagnosis of any disorder for which there is a suitable target for heteromultimer generation. The article of manufacture comprises a container and a label or package insert on or associated with the container. Suitable containers include, for example, bottles, vials, syringes, etc. The containers may be formed from a variety of materials such as glass or plastic. The container holds a composition that is effective for treating the condition and may have a sterile access port (for example the container may be an intravenous solution bag or a vial having a stopper pierceable by a hypodermic injection needle). At least one active agent in the composition is a heteromultimer of the invention. The label or package insert indicates that the composition is used for treating the particular condition. The label or package insert will further comprise instructions for administering the heteromultimer composition to the subject. Articles of manufacture and kits comprising combinatorial therapies described herein are also contemplated.

Package insert refers to instructions customarily included in commercial packages of therapeutic products that contain information about the indications, usage, dosage, administration, contraindications and/or warnings concerning the use of such therapeutic products.

Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials considered from a commercial and user standpoint, including other buffers, diluents, filters, needles, and syringes.

Kits are also provided that are useful for various purposes, e.g., for purification or immunoprecipitation of an antigen from cells. For isolation and purification of an antigen the kit can contain a heteromultimer coupled to beads (e.g., sepharose beads). Kits can be provided which contain the heteromultimers for detection and quantitation of the antigen in vitro, e.g., in an ELISA or a Western blot. As with the article of manufacture, the kit comprises a container and a label or package insert on or associated with the container. The container holds a composition comprising at least one heteromultimer of the invention. Additional containers may be included that contain, e.g., diluents and buffers or control heteromultimers. The label or package insert may provide a description of the composition as well as instructions for the intended in vitro or diagnostic use.

VIII. Target Molecules

Examples of molecules that may be targeted by a heteromultimer (e.g., a single-chain or multi-chain antibody, or an immunoadhesin-antibody complex) of this invention include, but are not limited to, soluble serum proteins, receptor proteins, membrane-bound proteins (e.g., adhesins), cytokines, chemokines, growth factors, and hormones.

Soluble antigens or fragments thereof, optionally conjugated to other molecules, can be used as immunogens for generating heteromultimers. For transmembrane molecules, such as receptors, fragments of these (e.g., the extracellular domain of a receptor) can be used as the immunogen. Alternatively, cells expressing the transmembrane molecule can be used as the immunogen. Such cells can be derived from a natural source (e.g., cancer cell lines) or may be cells which have been transformed by recombinant techniques to express the transmembrane molecule. Other antigens and forms thereof useful for preparing heteromultimers will be apparent to those in the art.

The foregoing written description is considered to be sufficient to enable one skilled in the art to practice the invention. The following Examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims. The description provided in the Examples is intended to be considered generally as a part of the invention.

EXAMPLES

Example 1. Construction of Vectors for the Expression of HD Tether-Containing Heteromultimers All HD tether-containing heteromultimeric single-chain antibody constructs were made from existing IgG1 monoclonal antibody constructs already available in-house. LCs were prepared using PCR wherein the 3' primer of the LC extended beyond the LC C-terminus, encoding for the N-terminal portion of the CLH-tether and terminating in a BamHI site. The 5' LC primer terminated in a ClaI site. The PCR fragment was then digested and cloned into a similarly digested and dephosphorylated pRK vector (Genentech Inc.; Eaton et al., Biochemistry 25:8343-8347 (1986)). The cognate HC was then prepared using PCR wherein the 5' primer extended beyond the HC N-terminus (minus the signal sequence), encoding for the C-terminal portion of the CLH-tether and terminating in a BamHI site. The 3' HC primer terminated in an XbaI site. The HC PCR fragment was digested and cloned into a similarly prepared plasmid containing the cognate LC described above and thus forming a tethered half-antibody. The BamHI site is positioned such that it encodes for the amino acid residues "GS" and maintains the integrity of the tether's GGS repeats. The lysine residue at position K222 (Kabat numbering scheme) was next mutated into an alanine residue using Stratagene's Quikchange II XL site-directed mutagenesis kit.

Two of the above-described CLH-tethered half-antibodies were then joined together via another round of PCR wherein the half-antibody destined for the N-terminus of the single-chain antibody was amplified using the same 5' LC primer used above and a 3' primer which extended beyond the C-terminus of the HC, encoding for the N-terminus of the HD tether and terminating in a BspEI site. The PCR fragment was digested and cloned into a similarly digested and dephosphorylated pRK vector. The half-antibody destined for the C-terminus of the heteromultimeric single-chain antibody was amplified using the same 3' HC primer used in constructing the half-antibodies and a 5' primer which extended beyond the LC N-terminus (minus the signal sequence), encoding for the C-terminal portion of the HD tether and terminating in a BspEI site. The PCR product was digested and cloned into a similarly digested and dephosphorylated N-terminal construct vector. As with BamHI, BspEI can be positioned such that it maintains the integrity of the tether's GGS repeats.

The construction of HD tether-containing heteromultimeric multi-chain antibodies was similar, differing only in that the N-terminal "half-antibody" began with the HC signal sequence and its cognate LC was expressed separately from a second pRK plasmid.

Example 2. Cleavage and Purification of HD Tether-Containing Heteromultimers An exemplary schema that can be used to purify heteromultimers of the invention is shown below.

Heteromultimers loaded onto a Protein A (e.g., mAbSure) column at 4° C.

↓

Column washed with KPO$_4$, then PBS + 0.1% Triton X114

↓

Sample eluted with 100 mM acetic acid (pH 2.9)

↓

-continued

Sample pH adjusted to pH 8.0 using 1M Tris and cleaved for 1.5 hr at 37° C., 1:500 (wt:wt) Lys-C

↓

Sample purified over mAbSure resin to remove Lys-C

↓

Sample eluted with 100 mM acetic acid (pH 2.9) and neutralized to pH 8 with using 1M Tris

↓

Sample cleaved with Carboxypeptidase B 1:5 (wt:wt) for 2.5 hr at 37° C.

↓

Sample pH adjusted and loaded onto cation exchange column in 20 mM NaAcetate pH 5.0 with gradient to 20 mM NaAcetate + 1M NaCl

↓

Collect fractions, pool & dialyze into PBS

In particular, heteromultimers were purified from conditioned media using mAbSure Select resin from GE Healthcare (Sweden) overnight at 4° C. The column was washed with two column volumes (CV) of PBS (phosphate buffered saline), followed by 10 CV of PBS+0.1% Triton X114 detergent, followed by 10 CV potassium phosphate buffer. The columns were eluted with 100 mM Acetic Acid (pH 2.9) and immediately adjusted to pH 8.0 with Tris (200 mM final concentration), pH 8.0. HD tethers were removed from heteromultimers upon treatment with a 1:500 (wt:wt) ratio of Lys-C endopeptidase (Wako Pure Chemical Laboratories) at 37° C. for 1-5 hours. Sample then loaded onto column to remove enzyme. Residual furin recognition sites are subsequently removed using 1:5 (wt:wt) porcine Carboxypeptidase B (Roche Applied Sciences, Cat #10103233001) for 1-5 hours. Cleaved samples were loaded onto a cation exchange column to remove enzyme. Peak fractions were pooled and dialyzed against PBS overnight prior to mass spectrum analysis to ensure identity and purity.

Example 3. Characterization of Engineered Heteromultimers

To determine whether the exemplary heteromultimers constructed using HD tether heterodimerization technology of the invention retained the binding properties of the antibodies or adhesins from which their sequences were derived, binding assays were conducted (FIGS. 6A-6D). These binding assays were run using the kinetics wizard program on the ForteBio Octet system. All samples tested were at a concentration of 25 µg/ml, a concentration that indicates saturation of the anti-human IgG probes in repeat experiments and among varying samples. The probes were loaded with the first sample for 10 minutes and washed for 30 seconds in PBS. All associations for the second and third samples were carried out for 15 minutes with 30-second PBS washes between associations.

Other Embodiments

All patents, patent applications, patent application publications, and other publications cited or referred to in this specification are herein incorporated by reference to the same extent as if each independent patent, patent application, patent application publication or publication was specifically and individually indicated to be incorporated by reference.

What is claimed is:

1. A single-chain antibody comprising a single polypeptide, wherein said a single polypeptide comprises the following domains positioned relative to each other in an N-terminal to C-terminal direction: $VL_1$-$CL_1$-CLH tether$_1$-$VH_1$-$CH1_1$-hinge$_1$-$CH2_1$-$CH3_1$-HD tether-$VL_2$-$CL_2$-CLH tether$_2$-$VH_2$-$CH1_2$-hinge$_2$-$CH2_2$-$CH3_2$.

2. The single-chain antibody of claim 1, wherein said HD tether is between 15-100 amino acids in length.

3. The single-chain antibody of claim 2, wherein said HD tether is between 30-39 amino acids in length.

4. The single-chain antibody of claim 2, wherein said HD tether comprises glycine (G) and serine (S) residues.

5. The single-chain antibody of claim 4, wherein said HD tether comprises GGS repeats.

6. The single-chain antibody of claim 5, wherein said HD tether comprises 8 to 9 GGS repeats (SEQ ID NO: 19).

7. The single-chain antibody of claim 1, wherein said HD tether comprises an amino acid sequence cleavable by an endopeptidase.

8. The single-chain antibody of claim 7, wherein said amino acid sequence is cleaved in situ by said endopeptidase.

9. The single-chain antibody of claim 7, wherein said amino acid sequence is cleaved upon addition of said endopeptidase following purification.

10. The single-chain antibody of claim 7, wherein said HD tether comprises two amino acid sequences cleavable by an endopeptidase located at the N- and C-termini of said HD tether.

11. The single-chain antibody of claim 7, wherein said endopeptidase is selected from the group consisting of furin, urokinase, thrombin, tissue plasminogen activator (tPa), genenase, Lys-C, Arg-C, Asp-N, Glu-C, Factor Xa, tobacco etch virus protease (TEV), enterokinase, human rhinovirus C3 protease (HRV C3), and kininogenase.

12. The single-chain antibody of claim 11, wherein said endopeptidase is furin.

13. The single-chain antibody of claim 12, wherein said HD tether comprises two endopeptidase cleavage sites located at the N- and C-termini of said HD tether, wherein one of said endopeptidase cleavage sites is a furin cleavage site.

14. The single-chain antibody of claim 12, wherein the amino acid sequence cleavable by furin comprises the amino acid sequence RKRKRR (SEQ ID NO:9).

15. The single-chain antibody of claim 12, wherein the amino acid sequence cleavable by furin comprises the amino acid sequence RHRQPR (SEQ ID NO:10).

16. The single-chain antibody of claim 13, wherein one of said endopeptidase cleavage sites is a Lys-C cleavage site.

17. The single-chain antibody of claim 1, wherein said CLH tether$_1$ or said CLH tether$_2$ comprises glycine (G) and serine (S) residues.

18. The single-chain antibody of claim 17, wherein said CLH tether$_1$ or said CLH tether$_2$ comprises GGS repeats.

19. The single-chain antibody of claim 17, wherein said CLH tether$_1$ and said CLH tether$_2$ are each between 10-80 amino acids in length.

20. The single-chain antibody of claim 19, wherein said CLH tether$_1$ and said CLH tether$_2$ are each between 20-40 amino acids in length.

21. The single-chain antibody of claim 1, wherein said CLH tether$_1$ or said CLH tether$_2$ comprises an amino acid sequence cleavable by an endopeptidase.

22. The single-chain antibody of claim 21, wherein said amino acid sequence is cleaved in situ by said endopeptidase.

23. The single-chain antibody of claim 21, wherein said amino acid sequence is cleaved upon addition of said endopeptidase following purification.

24. The single-chain antibody of claim 21, wherein said endopeptidase is selected from the group consisting of furin, urokinase, thrombin, tissue plasminogen activator (tPa), genenase, Lys-C, Arg-C, Asp-N, Glu-C, Factor Xa, tobacco etch virus protease (TEV), enterokinase, human rhinovirus C3 protease (HRV C3), and kininogenase.

25. The single-chain antibody of claim 24, wherein said endopeptidase is furin.

26. The single-chain antibody of claim 25, wherein said CLH tether$_1$ or said CLH tether$_2$ comprises two endopeptidase cleavage sites located at the N- and C-termini of said CLH tether$_1$ or said CLH tether$_2$, wherein said endopeptidase cleavage sites are both furin cleavage sites.

27. The single-chain antibody of claim 25, wherein the amino acid sequence cleavable by furin comprises the amino acid sequence RKRKRR (SEQ ID NO:9).

28. The single-chain antibody of claim 25, wherein the amino acid sequence cleavable by furin comprises the amino acid sequence RHRQPR (SEQ ID NO:10).

29. The single-chain antibody of claim 1, wherein said first hinge domain or said second hinge domain comprises Glu216 to Pro230 of human IgG1.

30. The single-chain antibody of claim 29, wherein said first hinge domain or said second hinge domain comprises a Lys-C endopeptidase cleavage site.

31. The single-chain antibody of claim 30, wherein said Lys-C endopeptidase cleavage site comprises an inactivating mutation.

32. The single-chain antibody of claim 31, wherein said inactivating mutation is a K222A substitution (EU numbering system).

33. The single-chain antibody of claim 1, wherein said single-chain antibody is a bispecific or a multispecific single-chain antibody.

34. The single-chain antibody of claim 33, wherein said single-chain antibody is capable of binding at least two antigens.

35. The single-chain antibody of claim 33, wherein said single-chain antibody is capable of binding at least two epitopes on the same antigen.

36. The single-chain antibody of claim 1, wherein said single-chain antibody comprises a constant region conjugated to a functional moiety on at least one Fc component.

37. The single-chain antibody of claim 1, wherein said single-chain antibody comprises one or more cleavage sites for an exopeptidase following cleavage of one or more of said HD or CLH tethers.

38. The single-chain antibody of claim 37, wherein said one or more cleavage sites are cleaved in situ by said exopeptidase.

39. The single-chain antibody of claim 37, wherein said one or more cleavage sites are cleaved upon addition of said exopeptidase following purification.

40. The single-chain antibody of claim 37, wherein said exopeptidase is selected from the group consisting of Carboxypeptidase A, Carboxypeptidase B, plasma Carboxypeptidase B, Carboxypeptidase D, Carboxypeptidase E, Carboxypeptidase M, Carboxypeptidase N, and Carboxypeptidase Z.

41. The single-chain antibody of claim 40, wherein said exopeptidase cleaves at a basic residue.

42. The single-chain antibody of claim 41, wherein said exopeptidase is a Carboxypeptidase B.

43. The single-chain antibody of claim 1, wherein said $CH3_1$ and $CH3_2$ domains each comprise a protuberance or cavity, and wherein said protuberance or cavity in said $CH3_1$ domain is positionable in said cavity or protuberance, respectively, in said $CH3_2$ domain.

44. The single-chain antibody of claim 43, wherein said $CH3_1$ and $CH3_2$ domains meet at an interface between said protuberance and cavity.

45. The single-chain antibody of claim 1, wherein said polypeptide further comprises:
   (a) a protuberance or cavity in said $CH1_1$ domain or said $CH1_2$ domain or both, and
   (b) a protuberance or cavity in said $CL_1$ domain or said $CL_2$ domain or both; and wherein:
   (c) said protuberance or cavity in said $CH1_1$ domain is positionable in said cavity or protuberance, respectively, in said $CL_1$ domain,
   (d) said protuberance or cavity in said $CH1_2$ domain is positionable in said cavity or protuberance, respectively, in said $CL_2$ domain; or
   (e) both (c) and (d).

46. The single-chain antibody of claim 45, wherein said $CH1_1$ and $CL_1$ domains, said $CH1_2$ and $CL_2$ domains, or all four of said domains meet at an interface between said protuberance and cavity.

47. The single-chain antibody of claim 1, wherein one or more of said $CH2_1$ or $CH2_2$ domains comprises a CH2 domain mutation that affects antibody effector function.

48. The single-chain antibody of claim 47, wherein said CH2 domain mutation that affects antibody effector function is an N297 mutation.

49. The single-chain antibody of claim 24, wherein said $CLH\ tether_1$ or said $CLH\ tether_2$ comprises two endopeptidase cleavage sites located at the N- and C-termini of said $CLH\ tether_1$ or said $CLH\ tether_2$, wherein one of said endopeptidase sites is a furin cleavage site and one of said endopeptidase sites is a Lys-C cleavage site.

50. The single-chain antibody of claim 12, wherein the amino acid sequence cleavable by furin comprises the amino acid sequence of RXRXRR (SEQ ID NO:8), wherein X is any amino acid residue.

51. The single-chain antibody of claim 25, wherein the amino acid sequence cleavable by furin comprises the amino acid sequence of RXRXRR (SEQ ID NO:8), wherein X is any amino acid residue.

52. The single chain antibody of claim 12, wherein the amino acid sequence cleavable by furin comprises the amino acid sequence of RXRXYR (SEQ ID NO: 7), wherein Y is K or R and X is any amino acid residue.

53. The single chain antibody of claim 25, wherein the amino acid sequence cleavable by furin comprises the amino acid sequence of RXRXYR (SEQ ID NO: 7), wherein Y is K or R and X is any amino acid residue.

* * * * *